US009221864B2

(12) United States Patent
Seth et al.

(10) Patent No.: US 9,221,864 B2
(45) Date of Patent: Dec. 29, 2015

(54) TRICYCLIC NUCLEIC ACID ANALOGS

(71) Applicant: Isis Pharmaceuticals, Inc., Carlsbad (CA)

(72) Inventors: Punit P. Seth, Carlsbad, CA (US); Eric E. Swayze, Encinitas, CA (US); Stephen Hanessian, Beaconsfield (CA); Benjamin R. Schroeder, Green Brook, NJ (US); Robert D. Giacometti, Montreal (CA); Bradley L. Merner, Laval (CA)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/391,264

(22) PCT Filed: Mar. 20, 2013

(86) PCT No.: PCT/US2013/033149
§ 371 (c)(1),
(2) Date: Oct. 8, 2014

(87) PCT Pub. No.: WO2013/154798
PCT Pub. Date: Oct. 17, 2013

(65) Prior Publication Data
US 2015/0112055 A1 Apr. 23, 2015

Related U.S. Application Data

(60) Provisional application No. 61/621,851, filed on Apr. 9, 2012.

(51) Int. Cl.
*C07H 21/00* (2006.01)
*C07H 19/04* (2006.01)
*C07H 19/06* (2006.01)

(52) U.S. Cl.
CPC ............... *C07H 19/06* (2013.01); *C07H 19/04* (2013.01); *C07H 21/00* (2013.01)

(58) Field of Classification Search
None
See application file for complete search history.

(56) References Cited

U.S. PATENT DOCUMENTS

| 3,687,808 | A | 8/1972 | Merigan et al. |
| 4,415,732 | A | 11/1983 | Caruthers et al. |
| 4,458,066 | A | 7/1984 | Caruthers et al. |
| 4,469,863 | A | 9/1984 | Ts'o et al. |
| 4,476,301 | A | 10/1984 | Imbach et al. |
| 4,500,707 | A | 2/1985 | Caruthers et al. |
| 4,668,777 | A | 5/1987 | Caruthers et al. |
| 4,725,677 | A | 2/1988 | Koster et al. |
| 4,845,205 | A | 7/1989 | Huynh Dinh et al. |
| 4,973,679 | A | 11/1990 | Caruthers et al. |
| 4,981,957 | A | 1/1991 | Lebleu et al. |
| 5,013,830 | A | 5/1991 | Ohutsuka et al. |
| 5,023,243 | A | 6/1991 | Tullis |
| 5,034,506 | A | 7/1991 | Summerton et al. |
| 5,118,800 | A | 6/1992 | Smith et al. |
| 5,130,302 | A | 7/1992 | Spielvogel et al. |
| 5,132,418 | A | 7/1992 | Caruthers et al. |
| 5,134,066 | A | 7/1992 | Rogers et al. |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,177,198 | A | 1/1993 | Spielvogel et al. |
| 5,185,444 | A | 2/1993 | Summerton et al. |
| 5,188,897 | A | 2/1993 | Suhadolnik et al. |
| 5,194,599 | A | 3/1993 | Froehler |
| 5,214,134 | A | 5/1993 | Weis et al. |
| 5,216,141 | A | 6/1993 | Benner |
| 5,220,007 | A | 6/1993 | Pederson et al. |
| 5,223,618 | A | 6/1993 | Cook et al. |
| 5,235,033 | A | 8/1993 | Summerton et al. |
| 5,256,775 | A | 10/1993 | Froehler |
| 5,264,423 | A | 11/1993 | Cohen et al. |
| 5,264,564 | A | 11/1993 | Matteucci |
| 5,276,019 | A | 1/1994 | Cohen et al. |
| 5,278,302 | A | 1/1994 | Caruthers et al. |
| 5,286,717 | A | 2/1994 | Cohen et al. |
| 5,319,080 | A | 6/1994 | Leumann |
| 5,321,131 | A | 6/1994 | Agrawal et al. |
| 5,359,044 | A | 10/1994 | Cook et al. |
| 5,366,878 | A | 11/1994 | Pederson et al. |

(Continued)

FOREIGN PATENT DOCUMENTS

| WO | WO 94/02499 | 2/1994 |
| WO | WO 94/17093 | 8/1994 |

(Continued)

OTHER PUBLICATIONS

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Altmann et al., "Second Generation Antisense Oligonucleotides—Inhibitionof PKC-α and c-raf Kinase Expression by Chimeric Oligonucleotides Incorporating 6"-Substituted Carbocyclic Nucleosides and 2"-O- Ethylene Glycol Substituted Ribonucleosides" Nuclewsodies Nucleotides. (1997) 16:917-926.

Altmann et al., "Second Generation of Antisense Oligonucleotides: From Nuclease Resistance to Biological Efficacy in Animals " Chimia. (1996) 50(4):168-176.

(Continued)

*Primary Examiner* — Traviss C McIntosh, III
(74) *Attorney, Agent, or Firm* — McNeill Baur PLLC

(57) ABSTRACT

The present disclosure provides tricyclic nucleosides and oligomeric compounds prepared therefrom. The tricyclic nucleosides each have a tricyclic ribosyl sugar moiety wherein a bridge between the 2' and 4' ribosyl ring carbon atoms further comprises a fused carbocyclic or heterocyclic ring. The tricyclic nucleosides are expected to be useful for enhancing properties of oligomeric compounds including for example binding affinity and nuclease resistance.

21 Claims, No Drawings

(56) References Cited

U.S. PATENT DOCUMENTS

| | | | |
|---|---|---|---|
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Buhr et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,426,220 B1 | 7/2002 | Bennett et al. |
| 6,525,191 B1 | 2/2003 | Ramasamy |
| 6,600,032 B1 | 7/2003 | Manoharan et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,399,845 B2 | 7/2008 | Seth et al. |
| 7,427,672 B2 | 9/2008 | Imanishi et al. |
| 7,741,457 B2 | 6/2010 | Seth et al. |
| 8,846,637 B2 * | 9/2014 | Seth et al. .................. 514/45 |
| 8,957,200 B2 * | 2/2015 | Seth et al. .................. 536/26.1 |
| 8,993,528 B2 * | 3/2015 | Swayze et al. .................. 514/43 |
| 2003/0082807 A1 | 5/2003 | Wengel |
| 2003/0158403 A1 | 8/2003 | Manoharan et al. |
| 2003/0207841 A1 | 11/2003 | Kaneko et al. |
| 2003/0224377 A1 | 12/2003 | Wengel et al. |
| 2004/0014959 A1 | 1/2004 | Sorensen et al. |
| 2004/0143114 A1 | 7/2004 | Imanishi et al. |
| 2004/0171570 A1 | 9/2004 | Allerson et al. |
| 2004/0192918 A1 | 9/2004 | Imanishi et al. |
| 2004/0219565 A1 | 11/2004 | Kauppinen et al. |
| 2005/0130923 A1 | 6/2005 | Bhat et al. |
| 2007/0287831 A1 | 12/2007 | Seth et al. |
| 2008/0039618 A1 | 2/2008 | Allerson et al. |

FOREIGN PATENT DOCUMENTS

| | | |
|---|---|---|
| WO | WO 98/39352 | 9/1998 |
| WO | WO 99/14226 | 3/1999 |
| WO | WO 00/66604 | 11/2000 |
| WO | WO 01/49687 | 7/2001 |
| WO | WO 02/36743 | 5/2002 |
| WO | WO 2004/106356 | 12/2004 |
| WO | WO 2005/021570 | 3/2005 |
| WO | WO 2005/121371 | 12/2005 |
| WO | WO 2005/121372 | 12/2005 |
| WO | WO 2006/047842 | 5/2006 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/036696 | 4/2010 |
| WO | WO 2010/036698 | 4/2010 |
| WO | WO 2011/017521 | 2/2011 |

OTHER PUBLICATIONS

Altmann et al., "Second-generation antisense oligonucleotides: structure—activity relationships and the design of improved signal-transduction inhibitors" Biochem. Soc. Trans. (1996) 24:630-637.

Altschul et al., "Basic Local Alignment Search Tool" J. Mol. Biol. (1990) 215:403-410.

Baker et al., "2'-O-(2 Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.

Barany et al., "A New Amino Protecting Group Removable by Reduction. Chemistry of the Dithiasuccinoyl (Dts) Function" J. Am. Chem. Soc. (1977) 99:7363-7365.

Barany et al., "Kinetics and Mechanisms of the Thiolytic Removal of the Dithiasuccinoyl (Dts) Amino Protecting Group" J. Am. Chem. Soc. (1980) 102:3084-3095.

Bass, "Double-stranded RNA as a template for gene silencing" Cell (2000) 101:235-238.

Beaucage et al., "Advances in the Synthesis of Oligonucleotides by the Phosphoramidite Approach" Tetrahedron (1992) 48(12):2223-2311.

(56) References Cited

OTHER PUBLICATIONS

Beaucage et al., "The Functionalization of Oligonucleotides Via Phosphoramidite Derivatives" Tetrahedron (1993) 49(10):1925-1963.
Beaucage et al., "The Synthesis of Specific Ribonucleotides and Unrelated Phosphorylated Biomolecules by the Phosphoramidite Method" Tetrahedron (1993) 49(46):10441-10488.
Braasch et al., "Locked nucleic acid (LNA): fine-tuning the recognition of DNA and RNA" Chem. Biol. (2001) 8:1-7.
Brazma et al., "Gene expression data analysis" FEBS Letters (2000) 480:17-24.
Carulli et al., "High Throughput Analysis of Differential Gene Expression" J. Cell. Biochem. Suppl. (1998) 30:286-296.
Celis et al., "Gene expression profiling: monitoring transcription and translation products using DNA microarrays and proteomics" FEBS Lett (2000) 480:2-16.
Chiang et al., "Antisense Oligonucleotides Inhibit Intercellular Adhesion Molecule 1 Expression by Two Distinct Mechanisms" J. Biol. Chem. (1991) 266:18162-18171.
Conte et al., "Conformational properties and thermodynamics of the RNA duplex r(CGCAAAUUUGCG)2: comparison with the DNA analogue d(CGCAAATTTGCG)2" Nucl. Acids Res. (1997) 25(13):2627-2634.
Egli et al., "RNA hydration: a detailed look" Biochemistry (1996) 35:8489-8494.
Elayadi et al., "Application of PNA and LNA oligomers to chemotherapy" Curr. Opinion Invens. Drugs (2001) 2:558-561.
Elbashir, "Duplexes of 21-nucleotide RNAs mediate RNA interference in cultured mammalian cells" Nature (2001) 411:494-498.
Elbashir, "RNA interference is mediated by 21- and 22-nucleotide RNAs" Genes & Devel. (2001) 15:188-200.
Englisch et al., "Chemically Modified Oligonucleotides as Probes and Inhibitors" Agnew Chem. Int. Ed. Engl. (1991) 30:613-629.
Fire et al., "Potent and Specific Genetic Interference by Double-Stranded RNA in Caenorhabditis Elegans" Nature (1998) 391:806-811.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Fuchs et al., "Identification of Differentially Expressed Genes by Mutually Subtracted RNA Fingerprinting" Anal. Biochem. (2000) 286:91-98.
Gait et al., "Application of chemically synthesized RNA" RNA: Protein Interactions (1998) 1-36.
Gallo et al., "2'-C-Methyluridine Phosphoramidite: A New Building Block for the Preparation of RNA Analogues Carrying the 2'-Dydroxyl Group" Tetrahedron (2001) 57: 5707-5713.
Going et al., "Molecular Pathology and Future Developments" Eur. J. Cancer (1999) 35:1895-1904.
Gu et al., "Base pairing properties of D- and L-cyclohexene nucleic acids (CeNA)" Oligonucleotides (2003) 13(6):479-489.
Gu et al., "Enzymatic resolution and base pairing properties of D- and L-cyclohexenyl nucleic acids (CeNA)" Nucleosides Nucleotides Nucleic Acids (2005) 24(5-7):993-998.
Gu et al., "Synthesis of enantiomeric-pure cyclohexenyl nucleoside building blocks for oligonucleotide synthesis" Tetrahedron (2004) 60(9):2111-2123.
Hanessian et al., "Structure-Based Design of a Highly Constrained Nucleic Acid Analogue: Improved Duplex Stabilization by Restriction Sugar Pucker and Torsin Angle γ" Angew. Chem, Int. Ed. (2012) 51:11242-11245.
Horvath et al., "Stereoselective synthesis of (—)-ara-cyclohexenyl-adenine" Tetrahedron Letters (2007) 48:3621-3623.
Ittig et al., "Nuclear antisense effects in cyclophilin A pre-mRNA splicing by oligonucleotides: a comparison of tricyclo-DNA with LNA" Nucl. Acids Res. (2004) 32(1):346-353.
Jones et al., "RNA quantitation by fluorescence-based solution assay: RiboGreen reagent characterization" Analytical Biochemistry (1998) 265(2):368-374.
Jungblut et al., "Proteomics in human disease: Cancer, heart and infections diseases" Electrophoresis (1999) 20:2100-2110.
Jurecic et al., "Long-distance DD-PCR and cDNA microarrays" Curr. Opin. Microbiol. (2000) 3:316-321.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kumar et al., "The first analogues of LNA (locked nucleic acids): phosphorothioate-LNA and 2'-thio-LNA" Bioorg Med Chem Lett. (1998) 8:2219-2222.
Larson et al., "Rapid DNA Fingerprinting of Pathogens by Flow Cytometry" Cytometry (2000) 41:203-208.
Larsson et al., "High-throughput protein expression of cDNA products as a tool in functional genomics" J. Biotech. (2000) 80:143-157.
Lesnik et al., "Relative thermodynamic stability of DNA, RNA, and DNA:RNA hybrid duplexes: relationship with base composition and structure" Biochemistry (1995) 34(34):10807-10815.
Leumann et al., "DNA Analogues: From Supramolecular Principles to Biological Properties" Bioorganic & Medicinal Chemistry (2002) 10:841-854.
Madden et al., "Serial analysis of gene expression: from gene discovery to target identification" DDT (2000) 5:415-425.
March, J., Advanced Organic Chemistry, 3rd Edition, John Wiley & Sons, New York, 1985.
Martin, "New acces to 2'-O-alkylated ribonucleosides and properties of 2'-O-alkylated oligoribonucleotides" Hely. Chim. Acta. (1995) 78:486-504.
Miura et al., "Fluorometric determination of total mRNA with oligo(dT) immobilized on microtiter plates" Clin. Chem. (1996) 42:1758-1764.
Montgomery et al., "RNA as a target of double-stranded RNA-mediated genetic interference in Caenorhabditis elegans" Proc Natl. Acad. Sci. (1998) 95:15502-7.
Nauwelaerts et al., "Cyclohexenyl nucleic acids: conformationally flexible oligonucleotides" Nucleic Acids Res. (2005) 33(8):2452-2463.
Nauwelaerts et al., "Structural characterization and biological evaluation of small interfering RNAs containing cyclohexenyl nucleosides" J. Am. Chem. Soc. (2007) 129(30):9340-9348.
Nishikura et al., "A Short Primer on RNAi: RNA-Directed RNA Polymerase Acts as a Key Catalyst" Cell (2001) 107:415-418.
Orum et al., "Locked nucleic acids: A promising molecular family for gene-function analysis and antisense drug development" Curr. Opinion Mol. Ther. (2001) 3:239-243.
Prashar et al., "READS: A Method for Display of 3'-End Fragment of Restriction Enzyme-Digested cDNAs for Analysis of Differential Gene Expression" Methods Enzymol. (1999) 303:258-272.
Quaedflieg et al., "Conformation of the phosphate-methylated DNA dinucleotides d(CpC) and d(TpC). Formation of a parallel miniduplex exclusively for the S configuration at phosphorus" J. Org. Chem. (1990) 55(1):122-127.
Robeyns et al., "Oligonucleotides with cyclohexene-nucleoside building blocks: crystallization and preliminary X-ray studies of a left-handed sequence GTGTACAC" Acta. Crystallogr. Sect. F. Struct. Biol. Cryst. Commun. (2005) 61(Pt 6):585-586.
Robeyns et al., "Structure of the fully modified left-handed cyclohexene nucleic acid sequence GTGTACAC" J. Am. Chem. Soc. (2008) 130(6):1979-1984.
Sanghvi, "Heterocyclic base modifications in nucleic acids and their applications in antisense oligonucleotides" Antisense Research and Applications, Crooke and Lebleu ed., CRC Press (1993) 273-302.
Searle et al., "On the stability of nucleic acid structures in solution: enthalpy-entropy compensations, internal rotations and reversibility" Nucl. Acids Res. (1993) 21(9):2051-2056.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.

(56) References Cited

OTHER PUBLICATIONS

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

Sutcliffe et al., "TOGA: An automated parsing technology for analyzing expression of nearly all genes" Pnas (2000) 97:1976-1981.

Swayze et al., The Medicinal Chemistry of Oligonucleotides in Antisense a Drug Technology, Chapter 6, pp. 143-182, Crooke, S.T., ed., 2008.

Swayze et al., "Antisense oligonucleotides containing locked nucleic acid improve potency but cause significant hepatotoxicity in animals" Nucl. Acids Res. (2007) 35(2):687-700.

Tabara et al., "RNAi in C. elegans: Soaking in the Genome Sequence" Science (1998) 282:430-431.

The Concise Encyclopedia of Polymer Science and Engineering, Kroschwitz, J.I., Ed., John Wiley & Sons, 1990, 858-859.

Tusterman et al., "RNA helicase MUT-14-dependent gene silencing triggered in C. elegans by short antisense RNAs" Science (2002) 295:694-7.

Timmons et al., "Ingestion of bacterially expressed dsRNAs can produce specific and potent genetic interference in Caenorhabditis Elegans" Gene (2001) 263:103-112.

Timmons et al., "Specific Interference by Ingested dsRNA" Nature (1998) 395:854.

To, "Identification of Differential Gene Expression by High Throughput Analysis" Comb. Chem. High Throughput Screen (2000) 3:235-241.

Tijschl et al., "Targeted mRNA degradation by double-stranded RNA in vitro" Genes Dev. (1999) 13:3191-7.

Verbeure et al., "RNase H mediated cleavage of RNA by cyclohexene nucleic acid (CeNA)" Nucleic Acids Res. (2001) 29(24):4941-4947.

Wahlestedt et al., "Potent and nontoxic antisense oligonucleotide containing locked nucleic acids" Proc. Natl. Acad. Sci. USA (2000) 97: 5633-5638.

Wang et al., "A straightforward stereoselective synthesis of D- and L-5-hydroxy-4-hydroxymethyl-2- cyclohexenylguanine" J. Org. Chem. (2001) 66(25):8478-8482.

Wang et al., "Cyclohexene nucleic acids (CeNA) form stable duplexes with RNA and induce RNase H activity" Nucleosides Nucleotides Nucleic Acids (2001) 20(4-7):785-788.

Wang et al., "Cyclohexene Nucleic Acids (CeNA): Serum Stable Oligonucleotides that Activate RNase H and Increase Duplex Stability with Complementary RNA" J. Am. Chem. Soc. (2000) 122(36):8595-8602.

Wang et al., "Stereocontrolled synthesis of ara-type cyclohexenyl nucleosides" J. Org. Chem. (2003) 68(11):4499-4505.

Youssefyeh et al., "T-Substituted nucleosides. 4. Synthesis of some 4'-hydroxymethyl nucleosides" J. Org. Chem. (1979) 44(8):1301-1309.

Zhang et al., "PowerBLAST: A New Network Blast Application for Interactive or Automated Sequence Analysis and Annotation" Genome Res. (1997) 7:649-656.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

* cited by examiner

TRICYCLIC NUCLEIC ACID ANALOGS

CROSS REFERENCED TO RELATED APPLICATIONS

This application is a U.S. National Phase filing under 35 U.S.C. §371 claiming priority to International Serial No. PCT/US2013/033149 filed Mar. 20, 2013, which claims priority to U.S. Provisional Application 61/621,851, filed Apr. 9, 2012, each of which is incorporated herein by reference in its entirety.

SEQUENCE LISTING

The present application is being filed along with a Sequence Listing in electronic format. The Sequence Listing is provided as a file entitled CHEM0081USAEQ_ST25.txt created Jul. 8, 2014, which is 8 Kb in size. The information in the electronic format of the sequence listing is incorporated herein by reference in its entirety.

FIELD OF THE INVENTION

The present disclosure provides tricyclic nucleic acid analogs and oligomeric compounds and compositions prepared therefrom. More particularly, tricyclic nucleosides are provided herein comprising a bridge between the 4' and 2' ring carbon atoms, wherein the bridge comprises a fused carbocyclic ring. In certain embodiments, the oligomeric compounds and compositions of the present disclosure are expected to hybridize to a portion of a target RNA resulting in loss of normal function of the target RNA.

BACKGROUND OF THE INVENTION

Antisense technology is an effective means for reducing the expression of one or more specific gene products and can therefore prove to be uniquely useful in a number of therapeutic, diagnostic, and research applications. Chemically modified nucleosides are routinely used for incorporation into antisense sequences to enhance one or more properties such as for example nuclease resistance. One such group of chemical modifications includes bicyclic nucleosides wherein the furanose portion of the nucleoside includes a bridge connecting two atoms on the furanose ring thereby forming a bicyclic ring system. Such bicyclic nucleosides have various names including BNA's and LNA's for bicyclic nucleic acids or locked nucleic acids respectively. Various BNA's have been prepared and reported in the patent literature as well as in scientific literature, see for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Wengel et al., PCT International Application WO 98-DK393 19980914; Singh et al., J. Org. Chem., 1998, 63, 10035-10039, the text of each is incorporated by reference herein, in their entirety. Examples of issued US patents and published applications include for example: U.S. Pat. Nos. 7,053,207, 6,770,748, 6,268,490 and 6,794,499 and published U.S. applications 20040219565, 20040014959, 20030207841, 20040192918, 20030224377, 20040143114 and 20030082807; the text of each is incorporated by reference herein, in their entirety.

In one in vivo study with LNA in mice, hepatotoxicity was reported. See, e.g., Swayze et al., Antisense oligonucleotides containing locked nucleic acid improve potency but cause significant hepatotoxicity in animals, Nucl. Acids Res., 2007, 35(2), 687-700.

In another study the induction of exon skipping in cyclophilin A pre-mRNA in HeLa cells compared tricyclo-DNA with LNA (Ittig et al., Nucl. Acids Res., 2004, 32(1), 346-353). In this study the tricyclo-DNA was several fold more effective than the LNA apparently because of its better intracellular distribution even though it had a lower Tm than the LNA. Such data encourage further research into DNA and or LNA analogs.

BRIEF SUMMARY OF THE INVENTION

Disclosed herein are tricyclic nucleic acid analogs (also referred to herein as tricyclic nucleosides) and antisense compounds prepared therefrom which are expected to be useful for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

Provided herein are novel tricyclic nucleosides and oligomeric compounds prepared therefrom. More particularly, novel tricyclic nucleosides are provided wherein each furanose ring comprises one 4'-CH—O-2' bridge between the 4' and 2' ring atoms and an additional fused ring resulting from a group connecting the 5'-atom to the methylene group of the 4'-CH—O-2' bridge. The variables are defined individually in further detail herein. It is to be understood that the tricyclic nucleosides provided herein and the oligomeric compounds prepared therefrom include all combinations of the embodiments disclosed and variables defined herein.

In certain embodiments, tricyclic nucleosides are provided having Formula I:

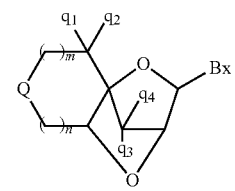

wherein:
Bx is a heterocyclic base moiety;
Q is $CH_2$—$CH_2$, CH=CH, O, S, or $NR_1$;
$R_1$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or a protecting group;
wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$, N(H)C(=S)$NJ_1J_2$ and a protecting group;
one of $q_1$ and $q_2$ is hydroxyl or a protected hydroxyl and the other of $q_1$ and $q_2$ is H;
one of $q_3$ and $q_4$ is hydroxyl, a protected hydroxyl or a reactive phosphorus group and the other of $q_3$ and $q_4$ is H;
n is 1 or 2; and
m is 0 when Q is $CH_2$—$CH_2$ or CH=CH and m is 1 when Q is O, S, or $NR_1$.

In certain embodiments, Bx is a pyrimidine, substituted pyrimidine, purine or substituted purine. In certain embodiments, Bx is uracil, thymine, cytosine, 5-methylcytosine, adenine or guanine.

In certain embodiments, the reactive phosphorus group is a phosphoramidite, H-phosphonate or phosphate triester.

In certain embodiments, n is 1.

In certain embodiments, Q is CH=CH. In certain embodiments, Q is $CH_2$—$CH_2$. In certain embodiments, Q is O. In certain embodiments, Q is S. In certain embodiments, Q is $NR_1$. In certain embodiments, $R_1$ is H, $C_1$-$C_3$ alkyl or substituted $C_1$-$C_3$ alkyl. In certain embodiments, $R_1$ is methyl.

In certain embodiments, each protected hydroxyl group comprises a protecting group, independently, selected from acetyl, benzyl, t-butyldimethylsilyl, t-butyldiphenylsilyl or 4,4'-dimethoxytrityl.

In certain embodiments, tricyclic nucleosides are provided having the configuration of Formula Ia:

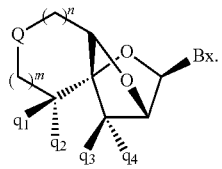

Ia

In certain embodiments, tricyclic nucleosides are provided having the configuration of Formula Ib:

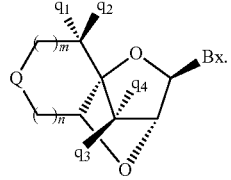

Ib

In certain embodiments, $q_1$ and $q_3$ are each H. In certain embodiments, $q_1$ and $q_4$ are each H. In certain embodiments, $q_2$ and $q_3$ are each H. In certain embodiments, $q_2$ and $q_4$ are each H. In certain embodiments, one of $q_1$ and $q_2$ is a 4,4'-dimethoxytrityl protected hydroxyl group and one of $q_3$ and $q_4$ is diisopropylcyanoethoxy phosphoramidite.

In certain embodiments, oligomeric compounds are provided comprising at least one tricyclic nucleoside having Formula II:

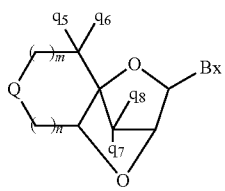

II wherein independently for each tricyclic nucleoside having Formula II:
  Bx is a heterocyclic base moiety;
  Q is $CH_2$—$CH_2$, CH=CH, O, S, or $NR_1$;

$R_1$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or a protecting group;

wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$, N(H)C(=S)$NJ_1J_2$ and a protecting group;

one of $q_5$ and $q_6$ is an internucleoside linking group linking the tricyclic nucleoside to the oligomeric compound, an optionally protected hydroxyl group or an oligomeric compound terminal group and the other of $q_5$ and $q_6$ is H;

one of $q_7$ and $q_8$ is an internucleoside linking group linking the tricyclic nucleoside to the oligomeric compound, an optionally protected hydroxyl group or an oligomeric compound terminal group and the other of $q_7$ and $q_8$ is H;

wherein at least one of $q_5$, $q_6$, $q_7$ and $q_8$ is an internucleoside linking group linking the tricyclic nucleoside to the oligomeric compound;

n is 1 or 2; and m is 0 when Q is $CH_2$—$CH_2$ or CH=CH and m is 1 when Q is O, S, or $NR_1$.

In certain embodiments, Bx is, independently, a pyrimidine, substituted pyrimidine, purine or substituted purine for each tricyclic nucleoside having Formula II. In certain embodiments, Bx is, independently, uracil, thymine, cytosine, 5-methylcytosine, adenine or guanine for each tricyclic nucleoside having Formula II.

In certain embodiments, n is 1 for each tricyclic nucleoside having Formula II.

In certain embodiments, Q is CH=CH for each tricyclic nucleoside having Formula II. In certain embodiments, Q is $CH_2$—$CH_2$ for each tricyclic nucleoside having Formula II. In certain embodiments, Q is O for each tricyclic nucleoside having Formula II. In certain embodiments, Q is S for each tricyclic nucleoside having Formula II. In certain embodiments, Q is $NR_1$ for each tricyclic nucleoside having Formula II. In certain embodiments, $R_1$ is H, $C_1$-$C_3$ alkyl or substituted $C_1$-$C_3$ alkyl for each tricyclic nucleoside having Formula II. In certain embodiments, $R_1$ is methyl for each tricyclic nucleoside having Formula II.

In certain embodiments, oligomeric compounds are provided comprising at least one tricyclic nucleoside of Formula II wherein each tricyclic nucleoside has the configuration of Formula IIa:

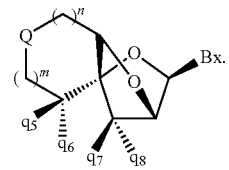

IIa

In certain embodiments, oligomeric compounds are provided comprising at least one tricyclic nucleoside of Formula II wherein each tricyclic nucleoside has the configuration of Formula IIb:

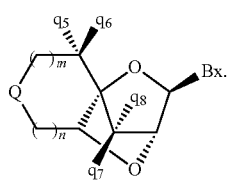

IIb

In certain embodiments, $q_5$ and $q_7$ are each H for each tricyclic nucleoside having Formula II, IIa or IIb. In certain embodiments, $q_5$ and $q_8$ are each H for each tricyclic nucleoside having Formula II, IIa or IIb. In certain embodiments, $q_6$ and $q_7$ are each H for each tricyclic nucleoside having Formula II, IIa or IIb. In certain embodiments, $q_6$ and $q_8$ are each H for each tricyclic nucleoside having Formula II, IIa or IIb.

In certain embodiments, oligomeric compounds are provided wherein each internucleoside linking group between adjacent monomeric subunits is, independently, a phosphodiester internucleoside linking group or a phosphorothioate internucleoside linking group. In certain embodiments, essentially each internucleoside linking group between adjacent monomeric subunits is a phosphorothioate internucleoside linking group.

In certain embodiments, oligomeric compounds are provided comprising a first region having at least two contiguous tricyclic nucleosides having Formula II, IIa or IIb. In certain embodiments, oligomeric compounds are provided comprising a first region having at least two contiguous tricyclic nucleosides having Formula II, IIa or IIb and a second region having at least two contiguous monomeric subunits wherein each monomeric subunit in the second region is a modified nucleoside different from the tricyclic nucleosides of said first region. In certain embodiments, oligomeric compounds are provided comprising a first region having at least two contiguous tricyclic nucleosides having Formula II, IIa or IIb, a second region having at least two contiguous monomeric subunits wherein each monomeric subunit in the second region is a modified nucleoside different from the tricyclic nucleosides of said first region and a third region located between said first and second regions wherein each monomer subunit in the third region is independently, a nucleoside or a modified nucleoside that is different from each tricyclic nucleoside of said first region and each monomer subunit the second region.

In certain embodiments, oligomeric compound are provided comprising a gapped oligomeric compound having an internal region of from 6 to 14 contiguous monomer subunits flanked on each side by an external region of from 1 to 5 contiguous monomer subunits wherein each monomer subunit in each external region is tricyclic nucleoside of formula II, IIa or IIb and each monomer subunit in the internal region is, independently, a nucleoside or modified nucleoside. In certain embodiments, the internal region comprises from about 8 to about 14 contiguous β-D-2'-deoxyribonucleosides. In certain embodiments, the internal region comprises from about 9 to about 12 contiguous β-D-2'-deoxyribonucleosides.

In certain embodiments, tricyclic nucleosides are provided having the configuration of Formula III:

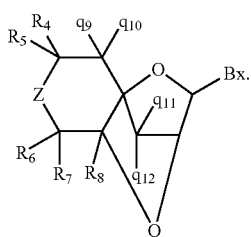

III wherein:
Bx is a heterocyclic base moiety;
Z is $CH_2$—$CH_2$, $CH$=$CH$, $CR_{15}R_{16}$, O, S, or $NR_{14}$;
each $R_4$, $R_5$, $R_6$, $R_7$ and $R_8$ are independently selected from the group consisting of H, hydroxyl, protected hydroxyl, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, $C_1$-$C_6$ substituted alkoxy, an alkyl ester, and a protecting group;
$R_{14}$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or a protecting group;
each $R_{15}$ and $R_{16}$ are independently selected from the group consisting of H, hydroxyl, protected hydroxyl, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl and a protecting group;
wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$, N(H)C(=S)$NJ_1J_2$ and a protecting group;
each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group;
one of $q_{11}$ and $q_{12}$ is hydroxyl or a protected hydroxyl and the other of $q_{11}$ and $q_{12}$ is H; and
one of $q_9$ and $q_{10}$ is hydroxyl, a protected hydroxyl or a reactive phosphorus group and the other of $q_9$ and $q_{10}$ is H.

In certain embodiments, oligomeric compounds are provided comprising at least one tricyclic nucleoside having Formula IV:

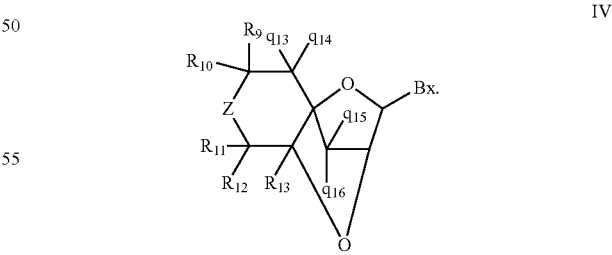

IV wherein independently for each tricyclic nucleoside having Formula II:
Bx is a heterocyclic base moiety;
Z is $CH_2$—$CH_2$, $CH$=$CH$, $CR_{18}R_{19}$, O, S, or $NR_{17}$;
each $R_9$, $R_{10}$, $R_{11}$, $R_{12}$ and $R_{13}$ are independently selected from the group consisting of H, hydroxyl, protected hydroxyl, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, $C_1$-$C_6$ substituted alkoxy, an alkyl ester, and a protecting group;

$R_{17}$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or a protecting group;

each $R_{18}$ and $R_{19}$ are independently selected from the group consisting of H, hydroxyl, protected hydroxyl, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl and a protecting group;

wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$, N(H)C(=S)$NJ_1J_2$ and a protecting group;

each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group;

one of $q_{15}$ and $q_{16}$ is an internucleoside linking group linking the tricyclic nucleoside to the oligomeric compound, an optionally protected hydroxyl group or an oligomeric compound terminal group and the other of $q_{15}$ and $q_{16}$ is H;

one of $q_{13}$ and $q_{14}$ is an internucleoside linking group linking the tricyclic nucleoside to the oligomeric compound, an optionally protected hydroxyl group or an oligomeric compound terminal group and the other of $q_{13}$ and $q_{14}$ is H; and wherein at least one of $q_{13}$, $q_{14}$, $q_{15}$ and $q_{16}$ is an internucleoside linking group linking the tricyclic nucleoside to the oligomeric compound.

In certain embodiments, methods of preparing tricyclic nucleosides are provided, said method comprising: reacting a first reactant and a second reactant in the presence of a solvent; wherein the first reactant comprises a compound represented by formula V:

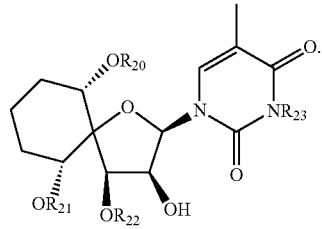

wherein each $R_{20}$, $R_{21}$, $R_{22}$, and $R_{23}$ are independently selected from the group consisting of H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl and a protecting group; and wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$, N(H)C(=S)$NJ_1J_2$ and a protecting group;

each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, the protecting group is selected from the group consisting of benzyl, phenyl, naphthyl, triflate, trimethylsilyl, tert-butyldiphenylsilyl, tert-butyldimethylsilyl, and benzyl chloromethyl ether.

In certain embodiments, the second reactant is a base. In certain embodiments, the base is selected from the group consisting of $NaNH_2$ and NaH. In certain embodiments, the solvent is selected from among a polar solvent, a polar aprotic solvent, a polar protic solvent, an apolar solvent, an apolar aprotic solvent, and an apolar protic solvent. In certain embodiments, the solvent is DMF.

In certain embodiments, the tricyclic nucleoside comprises a compound having Formula VI:

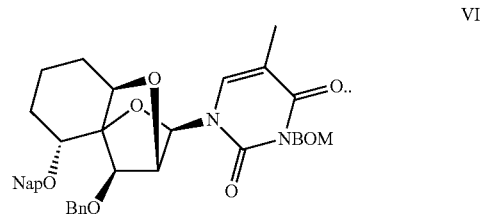

In certain embodiments, pharmaceutical compositions are provided comprising a compound of any of Formulas I-VI and a pharmaceutically acceptable carrier or diluent.

In certain embodiments methods of modulating target mRNA in a cell are provided, said method comprising contacting the cell with an oligomeric compound according to any of Formulas I-VI or a pharmaceutical composition thereof. In certain embodiments, the cell is in vitro. In certain embodiments, the cell is in an animal. In certain embodiments, the animal is a human.

DETAILED DESCRIPTION OF THE INVENTION

Provided herein are novel tricyclic nucleosides and oligomeric compounds prepared therefrom. The tricyclic nucleosides are expected to be useful for enhancing one or more properties of the oligomeric compounds they are incorporated into such as for example nuclease resistance. In certain embodiments, the oligomeric compounds provided herein are expected to hybridize to a portion of a target RNA resulting in loss of normal function of the target RNA.

In certain embodiments, tricyclic nucleosides are provided that can be incorporated into antisense oligomeric compounds to reduce target RNA, such as messenger RNA, in vitro and in vivo. In one aspect the reduction of target RNA is useful for inhibition of gene expression via numerous pathways. Such pathways include for example the steric blocking of transcription or translation and cleavage of mRNA via single or double stranded oligomeric compounds. The oligomeric compounds provided herein are also expected to be useful as primers and probes in diagnostic applications. In certain embodiments, oligomeric compounds comprising at least one of the tricyclic nucleosides provided herein are expected to be useful as aptamers which are oligomeric compounds capable of binding to aberrant proteins in an in vivo setting.

In certain embodiments, tricyclic nucleosides are provided having Formula I:

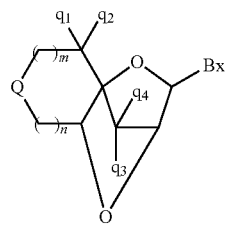

wherein:

Bx is a heterocyclic base moiety;

Q is $CH_2$—$CH_2$, $CH$=$CH$, O, S, or $NR_1$;

$R_1$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or a protecting group;

wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, $C(=O)OJ_1$, $C(=O)NJ_1J_2$, $C(=O)J_1$, O—$C(=O)NJ_1J_2$, $N(H)C(=O)NJ_1J_2$, $N(H)C(=S)NJ_1J_2$ and a protecting group;

one of $q_1$ and $q_2$ is hydroxyl or a protected hydroxyl and the other of $q_1$ and $q_2$ is H;

one of $q_3$ and $q_4$ is hydroxyl, a protected hydroxyl or a reactive phosphorus group and the other of $q_3$ and $q_4$ is H;

n is 1 or 2; and m is 0 when Q is $CH_2$—$CH_2$ or $CH$=$CH$ and m is 1 when Q is O, S, or $NR_1$.

In certain embodiments, Bx is a pyrimidine, substituted pyrimidine, purine or substituted purine. In certain embodiments, Bx is uracil, thymine, cytosine, 5-methylcytosine, adenine or guanine.

In certain embodiments, the reactive phosphorus group is a phosphoramidite, H-phosphonate or phosphate triester.

In certain embodiments, n is 1.

In certain embodiments, Q is $CH$=$CH$. In certain embodiments, Q is $CH_2$—$CH_2$. In certain embodiments, Q is O. In certain embodiments, Q is S. In certain embodiments, Q is $NR_1$. In certain embodiments, $R_1$ is H, $C_1$-$C_3$ alkyl or substituted $C_1$-$C_3$ alkyl. In certain embodiments, $R_1$ is methyl.

In certain embodiments, each protected hydroxyl group comprises a protecting group, independently, selected from acetyl, benzyl, t-butyldimethylsilyl, t-butyldiphenylsilyl or 4,4'-dimethoxytrityl.

In certain embodiments, tricyclic nucleosides are provided having the configuration of Formula Ia:

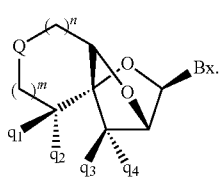

In certain embodiments, tricyclic nucleosides are provided having the configuration of Formula Ib:

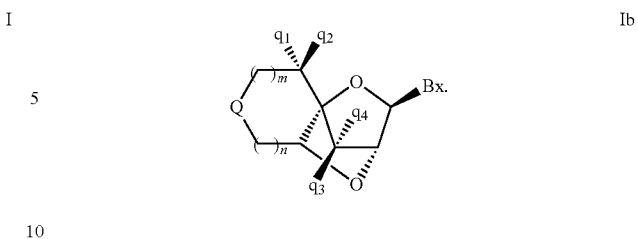

In certain embodiments, $q_1$ and $q_3$ are each H. In certain embodiments, $q_1$ and $q_4$ are each H. In certain embodiments, $q_2$ and $q_3$ are each H. In certain embodiments, $q_2$ and $q_4$ are each H. In certain embodiments, one of $q_1$ and $q_2$ is a 4,4'-dimethoxytrityl protected hydroxyl group and one of $q_3$ and $q_4$ is diisopropylcyanoethoxy phosphoramidite.

In certain embodiments, oligomeric compounds are provided comprising at least one tricyclic nucleoside having Formula II:

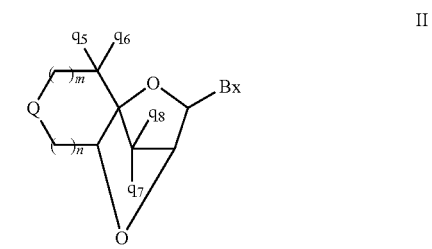

wherein independently for each tricyclic nucleoside having Formula II:

Bx is a heterocyclic base moiety;

Q is $CH_2$—$CH_2$, $CH$=$CH$, O, S, or $NR_1$;

$R_1$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or a protecting group;

wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, $C(=O)OJ_1$, $C(=O)NJ_1J_2$, $C(=O)J_1$, O—$C(=O)NJ_1J_2$, $N(H)C(=O)NJ_1J_2$, $N(H)C(=S)NJ_1J_2$ and a protecting group;

one of $q_5$ and $q_6$ is an internucleoside linking group linking the tricyclic nucleoside to the oligomeric compound, an optionally protected hydroxyl group or an oligomeric compound terminal group and the other of $q_5$ and $q_6$ is H;

one of $q_7$ and $q_8$ is an internucleoside linking group linking the tricyclic nucleoside to the oligomeric compound, an optionally protected hydroxyl group or an oligomeric compound terminal group and the other of $q_7$ and $q_8$ is H;

wherein at least one of $q_5$, $q_6$, $q_7$ and $q_8$ is an internucleoside linking group linking the tricyclic nucleoside to the oligomeric compound;

n is 1 or 2; and m is 0 when Q is $CH_2$—$CH_2$ or $CH$=$CH$ and m is 1 when Q is O, S, or $NR_1$.

In certain embodiments, Bx is, independently, a pyrimidine, substituted pyrimidine, purine or substituted purine for each tricyclic nucleoside having Formula II. In certain embodiments, Bx is, independently, uracil, thymine, cytosine, 5-methylcytosine, adenine or guanine for each tricyclic nucleoside having Formula II.

In certain embodiments, n is 1 for each tricyclic nucleoside having Formula II.

In certain embodiments, Q is CH=CH for each tricyclic nucleoside having Formula II. In certain embodiments, Q is CH$_2$—CH$_2$ for each tricyclic nucleoside having Formula II. In certain embodiments, Q is O for each tricyclic nucleoside having Formula II. In certain embodiments, Q is S for each tricyclic nucleoside having Formula II. In certain embodiments, Q is NR$_1$ for each tricyclic nucleoside having Formula II. In certain embodiments, R$_1$ is H, C$_1$-C$_3$ alkyl or substituted C$_1$-C$_3$ alkyl for each tricyclic nucleoside having Formula II. In certain embodiments, R$_1$ is methyl for each tricyclic nucleoside having Formula II.

In certain embodiments, oligomeric compounds are provided comprising at least one tricyclic nucleoside of Formula II wherein each tricyclic nucleoside has the configuration of Formula IIa:

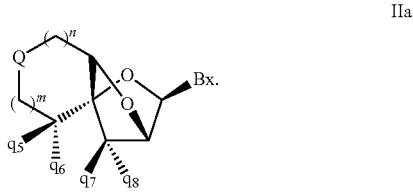

IIa

In certain embodiments, oligomeric compounds are provided comprising at least one tricyclic nucleoside of Formula II wherein each tricyclic nucleoside has the configuration of Formula IIb:

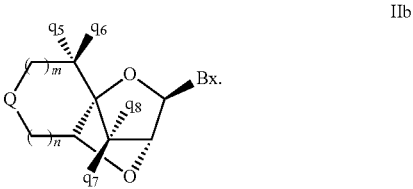

IIb

In certain embodiments, q$_5$ and q$_7$ are each H for each tricyclic nucleoside having Formula II, IIa or IIb. In certain embodiments, q$_5$ and q$_8$ are each H for each tricyclic nucleoside having Formula II, IIa or IIb. In certain embodiments, q$_6$ and q$_7$ are each H for each tricyclic nucleoside having Formula II, IIa or IIb. In certain embodiments, q$_6$ and q$_8$ are each H for each tricyclic nucleoside having Formula II, IIa or IIb.

In certain embodiments, oligomeric compounds are provided wherein each internucleoside linking group between adjacent monomeric subunits is, independently, a phosphodiester internucleoside linking group or a phosphorothioate internucleoside linking group. In certain embodiments, essentially each internucleoside linking group between adjacent monomeric subunits is a phosphorothioate internucleoside linking group.

In certain embodiments, oligomeric compounds are provided comprising a first region having at least two contiguous tricyclic nucleosides having Formula II, IIa or IIb. In certain embodiments, oligomeric compounds are provided comprising a first region having at least two contiguous tricyclic nucleosides having Formula II, IIa or IIb and a second region having at least two contiguous monomeric subunits wherein each monomeric subunit in the second region is a modified nucleoside different from the tricyclic nucleosides of said first region. In certain embodiments, oligomeric compounds are provided comprising a first region having at least two contiguous tricyclic nucleosides having Formula II, IIa or IIb, a second region having at least two contiguous monomeric subunits wherein each monomeric subunit in the second region is a modified nucleoside different from the tricyclic nucleosides of said first region and a third region located between said first and second regions wherein each monomer subunit in the third region is independently, a nucleoside or a modified nucleoside that is different from each tricyclic nucleoside of said first region and each monomer subunit the second region.

In certain embodiments, oligomeric compound are provided comprising a gapped oligomeric compound having an internal region of from 6 to 14 contiguous monomer subunits flanked on each side by an external region of from 1 to 5 contiguous monomer subunits wherein each monomer subunit in each external region is tricyclic nucleoside of formula II, IIa or IIb and each monomer subunit in the internal region is, independently, a nucleoside or modified nucleoside. In certain embodiments, the internal region comprises from about 8 to about 14 contiguous β-D-2'-deoxyribonucleosides. In certain embodiments, the internal region comprises from about 9 to about 12 contiguous β-D-2'-deoxyribonucleosides.

In certain embodiments, tricyclic nucleosides are provided having the configuration of Formula III:

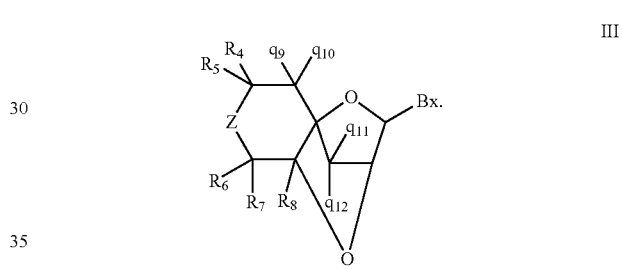

III wherein:
Bx is a heterocyclic base moiety;
Z is CH$_2$—CH$_2$, CH=CH, CR$_{15}$R$_{16}$, O, S, or NR$_{14}$;
each R$_4$, R$_5$, R$_6$, R$_7$ and R$_8$ are independently selected from the group consisting of H, hydroxyl, protected hydroxyl, halogen, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, C$_1$-C$_6$ alkoxy, C$_1$-C$_6$ substituted alkoxy, an alkyl ester, and a protecting group;
R$_{14}$ is H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl or a protecting group;
each R$_{15}$ and R$_{16}$ are independently selected from the group consisting of H, hydroxyl, protected hydroxyl, halogen, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl and a protecting group;
wherein each substituted group is, independently, mono or poly substituted with substituent groups independently selected from halogen, C$_1$-C$_6$ alkyl, C$_2$-C$_6$ alkenyl, C$_2$-C$_6$ alkynyl, OJ$_1$, SJ$_1$, NJ$_1$J$_2$, N$_3$, CN, C(=O)OJ$_1$, C(=O)NJ$_1$J$_2$, C(=O)J$_1$, O—C(=O)NJ$_1$J$_2$, N(H)C(=O)NJ$_1$J$_2$, N(H)C(=S)NJ$_1$J$_2$ and a protecting group;
each J$_1$ and J$_2$ is, independently, H, C$_1$-C$_6$ alkyl, C$_2$-C$_6$ alkenyl, C$_2$-C$_6$ alkynyl, C$_1$-C$_6$ aminoalkyl or a protecting group;
one of q$_{11}$ and q$_{12}$ is hydroxyl or a protected hydroxyl and the other of q$_{11}$ and q$_{12}$ is H; and
one of q$_9$ and q$_{10}$ is hydroxyl, a protected hydroxyl or a reactive phosphorus group and the other of q$_9$ and q$_{10}$ is H.

In certain embodiments, oligomeric compounds are provided comprising at least one tricyclic nucleoside having Formula IV:

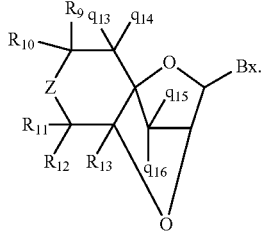

IV wherein independently for each tricyclic nucleoside having Formula II:

Bx is a heterocyclic base moiety;

Z is $CH_2$—$CH_2$, $CH$=$CH$, $CR_{18}R_{19}$, O, S, or $NR_{17}$;

each $R_9$, $R_{10}$, $R_{11}$, $R_{12}$ and $R_{13}$ are independently selected from the group consisting of H, hydroxyl, protected hydroxyl, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, $C_1$-$C_6$ substituted alkoxy, an alkyl ester, and a protecting group;

$R_{17}$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or a protecting group;

each $R_{18}$ and $R_{19}$ are independently selected from the group consisting of H, hydroxyl, protected hydroxyl, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl and a protecting group;

wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$, N(H)C(=S)$NJ_1J_2$ and a protecting group;

each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group;

one of $q_{15}$ and $q_{16}$ is an internucleoside linking group linking the tricyclic nucleoside to the oligomeric compound, an optionally protected hydroxyl group or an oligomeric compound terminal group and the other of $q_{15}$ and $q_{16}$ is H;

one of $q_{13}$ and $q_{14}$ is an internucleoside linking group linking the tricyclic nucleoside to the oligomeric compound, an optionally protected hydroxyl group or an oligomeric compound terminal group and the other of $q_{13}$ and $q_{14}$ is H; and wherein at least one of $q_{13}$, $q_{14}$, $q_{15}$ and $q_{16}$ is an internucleoside linking group linking the tricyclic nucleoside to the oligomeric compound.

In certain embodiments, methods of preparing tricyclic nucleosides are provided, said method comprising: reacting a first reactant and a second reactant in the presence of a solvent; wherein the first reactant comprises a compound represented by formula V:

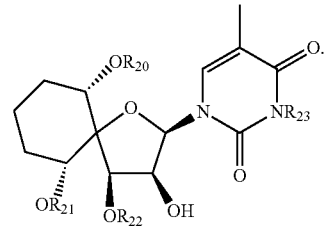

V wherein each $R_{20}$, $R_{21}$, $R_{22}$, and $R_{23}$ are independently selected from the group consisting of H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl and a protecting group; and wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$, N(H)C(=S)$NJ_1J_2$ and a protecting group;

each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, the protecting group is selected from the group consisting of benzyl, phenyl, naphthyl, triflate, trimethylsilyl, tert-butyldiphenylsilyl, tert-butyldimethylsilyl, and benzyl chloromethyl ether.

In certain embodiments, the second reactant is a base. In certain embodiments, the base is selected from the group consisting of $NaNH_2$ and NaH. In certain embodiments, the solvent is selected from among a polar solvent, a polar aprotic solvent, a polar protic solvent, an apolar solvent, an apolar aprotic solvent, and an apolar protic solvent. In certain embodiments, the solvent is DMF.

In certain embodiments, the tricyclic nucleoside comprises a compound having Formula VI:

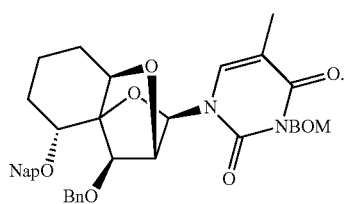

VI

In certain embodiments, pharmaceutical compositions are provided comprising a compound of any of Formulas I-VI and a pharmaceutically acceptable carrier or diluent.

In certain embodiments methods of modulating target mRNA in a cell are provided, said method comprising contacting the cell with an oligomeric compound according to any of Formulas I-VI or a pharmaceutical composition thereof. In certain embodiments, the cell is in vitro. In certain embodiments, the cell is in an animal. In certain embodiments, the animal is a human.

Incorporation of one or more of the tricyclic nucleosides, as provided herein, into an oligomeric compound is expected to enhance one or more desired properties of the resulting oligomeric compound. Such properties include without limitation stability, nuclease resistance, binding affinity, specificity, absorption, cellular distribution, cellular uptake, charge, pharmacodynamics and pharmacokinetics.

In certain embodiments, the tricyclic nucleosides provided herein are incorporated into oligomeric compounds such that a motif results. The placement of tricyclic nucleosides into oligomeric compounds to provide particular motifs can enhance the desired properties of the resulting oligomeric compounds for activity using a particular mechanism such as RNaseH or RNAi. Such motifs include without limitation, gapmer motifs, hemimer motifs, blockmer motifs, uniformly fully modified motifs, positionally modified motifs and alternating motifs. In conjunction with these motifs a wide variety of internucleoside linkages can also be used including but not limited to phosphodiester and phosphorothioate internucleoside linkages which can be incorporated uniformly or in various combinations. The oligomeric compounds can further include a 5' and or 3' terminal group such as a conjugate or reporter group. The positioning of the tricyclic nucleosides provided herein, the use of linkage strategies and 5' and or 3' terminal groups can be easily optimized to enhance a desired activity for a selected target.

As used herein the term "motif" refers to the pattern created by the relative positioning of monomer subunits within an oligomeric compound wherein the pattern is determined by comparing the sugar moieties of the linked monomer subunits. The only determinant for the motif of an oligomeric compound is the differences or lack of differences between the sugar moieties. The internucleoside linkages, heterocyclic bases and further groups such as terminal groups are not considered when determining the motif of an oligomeric compound.

Representative U.S. patents that teach the preparation of motifs include without limitation, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety. Motifs are also disclosed in International Applications PCT/US2005/019219, filed Jun. 2, 2005 and published as WO 2005/121371 on Dec. 22, 2005 and PCT/US2005/019220, filed Jun. 2, 2005 and published as WO 2005/121372 on Dec. 22, 2005; each of which is incorporated by reference herein in its entirety.

As used herein the term "alternating motif" refers to an oligomeric compound comprising a contiguous sequence of linked monomer subunits wherein the monomer subunits have two different types of sugar moieties that alternate for essentially the entire sequence of the oligomeric compound. Oligomeric compounds having an alternating motif can be described by the formula: 5'-A(-L-B-L-A)$_n$(-L-B)$_{nn}$-3' where A and B are monomer subunits that have different sugar moieties, each L is, independently, an internucleoside linking group, n is from about 4 to about 12 and nn is 0 or 1. The heterocyclic base and internucleoside linkage is independently variable at each position. The motif further optionally includes the use of one or more other groups including but not limited to capping groups, conjugate groups and other 5' and or 3'-terminal groups. This permits alternating oligomeric compounds from about 9 to about 26 monomer subunits in length. This length range is not meant to be limiting as longer and shorter oligomeric compounds are also amenable to oligomeric compounds provided herein. In certain embodiments, each A or each B comprise tricyclic nucleosides as provided herein.

As used herein the term "uniformly fully modified motif" refers to an oligomeric compound comprising a contiguous sequence of linked monomer subunits that each have the same type of sugar moiety. The heterocyclic base and internucleoside linkage is independently variable at each position. The motif further optionally includes the use of one or more other groups including but not limited to capping groups, conjugate groups and other 5' and or 3'-terminal groups. In certain embodiments, the uniformly fully modified motif includes a contiguous sequence of tricyclic nucleosides. In certain embodiments, one or both of the 5' and 3'-ends of the contiguous sequence of tricyclic nucleosides, comprise 5' and or 3'-terminal groups such as one or more unmodified nucleosides.

As used herein the term "hemimer motif" refers to an oligomeric compound comprising a contiguous sequence of monomer subunits that each have the same type of sugar moiety with a further short contiguous sequence of monomer subunits located at the 5' or the 3' end that have a different type of sugar moiety. The heterocyclic base and internucleoside linkage is independently variable at each position. The motif further optionally includes the use of one or more other groups including but not limited to capping groups, conjugate groups and other 5' and or 3'-terminal groups. In general, a hemimer is an oligomeric compound of uniform sugar moieties further comprising a short region (1, 2, 3, 4 or about 5 monomer subunits) having uniform but different sugar moieties located on either the 3' or the 5' end of the oligomeric compound.

In certain embodiments, the hemimer motif comprises a contiguous sequence of from about 10 to about 28 monomer subunits having one type of sugar moiety with from 1 to 5 or from 2 to about 5 monomer subunits having a second type of sugar moiety located at one of the termini. In certain embodiments, the hemimer is a contiguous sequence of from about 8 to about 20 β-D-2'-deoxyribonucleosides having from 1-12 contiguous tricyclic nucleosides located at one of the termini. In certain embodiments, the hemimer is a contiguous sequence of from about 8 to about 20 β-D-2'-deoxyribonucleosides having from 1-5 contiguous tricyclic nucleosides located at one of the termini. In certain embodiments, the hemimer is a contiguous sequence of from about 12 to about 18 β-D-2'-deoxyribonucleosides having from 1-3 contiguous tricyclic nucleosides located at one of the termini. In certain embodiments, the hemimer is a contiguous sequence of from about 10 to about 14 β-D-2'-deoxyribonucleosides having from 1-3 contiguous tricyclic nucleosides located at one of the termini.

As used herein the terms "blockmer motif" and "blockmer" refer to an oligomeric compound comprising an otherwise contiguous sequence of monomer subunits wherein the sugar moieties of each monomer subunit is the same except for an interrupting internal block of contiguous monomer subunits having a different type of sugar moiety. The heterocyclic base and internucleoside linkage is independently variable at each position of a blockmer. The motif further optionally includes the use of one or more other groups including but not limited to capping groups, conjugate groups and other 5' or 3'-terminal groups. A blockmer overlaps somewhat with a gapmer in the definition but typically only the monomer subunits in the block have non-naturally occurring sugar moieties in a blockmer and only the monomer subunits in the external regions have non-naturally occurring sugar moieties in a gapmer with the remainder of monomer subunits in the blockmer or gapmer being β-D-2'-deoxyribonucleosides or β-D-ribonucleosides. In certain embodiments, blockmers are provided herein wherein all of the monomer subunits comprise non-naturally occurring sugar moieties.

As used herein the term "positionally modified motif" is meant to include an otherwise contiguous sequence of monomer subunits having one type of sugar moiety that is interrupted with two or more regions of from 1 to about 5 contiguous monomer subunits having another type of sugar moiety. Each of the two or more regions of from 1 to about 5 contiguous monomer subunits are independently uniformly modified with respect to the type of sugar moiety. In certain embodiments, each of the two or more regions have the same type of sugar moiety. In certain embodiments, each of the two or more regions have a different type of sugar moiety. In certain embodiments, each of the two or more regions, independently, have the same or a different type of sugar moiety. The heterocyclic base and internucleoside linkage is independently variable at each position of a positionally modified oligomeric compound. The motif further optionally includes the use of one or more other groups including but not limited to capping groups, conjugate groups and other 5' or 3'-terminal groups. In certain embodiments, positionally modified oligomeric compounds are provided comprising a sequence of from 8 to 20 β-D-2'-deoxyribonucleosides that further includes two or three regions of from 2 to about 5 contiguous tricyclic nucleosides each. Positionally modified oligomeric compounds are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar moieties of the external regions being different than the sugar moieties of the internal region and wherein the sugar moiety of each monomer subunit within a particular region is essentially the same. In certain embodiments, each monomer subunit within a particular region has the same sugar moiety. When the sugar moieties of the external regions are the same the gapmer is a symmetric gapmer and when the sugar moiety used in the 5'-external region is different from the sugar moiety used in the 3'-external region, the gapmer is an asymmetric gapmer. In certain embodiments, the external regions are small (each independently 1, 2, 3, 4 or about 5 monomer subunits) and the monomer subunits comprise non-naturally occurring sugar moieties with the internal region comprising β-D-2'-deoxyribonucleosides. In certain embodiments, the external regions each, independently, comprise from 1 to about 5 monomer subunits having non-naturally occurring sugar moieties and the internal region comprises from 6 to 18 unmodified nucleosides. The internal region or the gap generally comprises β-D-2'-deoxyribonucleosides but can comprise non-naturally occurring sugar moieties. The heterocyclic base and internucleoside linkage is independently variable at each position of a gapped oligomeric compound. The motif further optionally includes the use of one or more other groups including but not limited to capping groups, conjugate groups and other 5' or 3'-terminal groups.

In certain embodiments, the gapped oligomeric compounds comprise an internal region of β-D-2'-deoxyribonucleosides with one of the external regions comprising tricyclic nucleosides as disclosed herein. In certain embodiments, the gapped oligomeric compounds comprise an internal region of β-D-2'-deoxyribonucleosides with both of the external regions comprising tricyclic nucleosides as provided herein. In certain embodiments, gapped oligomeric compounds are provided herein wherein all of the monomer subunits comprise non-naturally occurring sugar moieties.

In certain embodiments, gapped oligomeric compounds are provided comprising one or two tricyclic nucleosides at the 5'-end, two or three tricyclic nucleosides at the 3'-end and an internal region of from 10 to 16 β-D-2'-deoxyribonucleosides. In certain embodiments, gapped oligomeric compounds are provided comprising one tricyclic nucleoside at the 5'-end, two tricyclic nucleosides at the 3'-end and an internal region of from 10 to 16 β-D-2'-deoxyribonucleosides. In certain embodiments, gapped oligomeric compounds are provided comprising one tricyclic nucleosides at the 5'-end, two tricyclic nucleosides at the 3'-end and an internal region of from 10 to 14 β-D-2'-deoxyribonucleosides.

In certain embodiments, gapped oligomeric compounds are provided that are from about 10 to about 21 monomer subunits in length. In certain embodiments, gapped oligomeric compounds are provided that are from about 12 to about 16 monomer subunits in length. In certain embodiments, gapped oligomeric compounds are provided that are from about 12 to about 14 monomer subunits in length. In certain embodiments, gapped oligomeric compounds are provided that are from about 14 to about 16 monomer subunits in length.

As used herein the term "alkyl," refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein the term "alkenyl," refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein the term "alkynyl," refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein the term "acyl," refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein the term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein the term "aliphatic," refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein the term "alkoxy," refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein the term "aminoalkyl" refers to an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein the terms "aralkyl" and "arylalkyl," refer to an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein the terms "aryl" and "aromatic," refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein the terms "halo" and "halogen," refer to an atom selected from fluorine, chlorine, bromine and iodine.

As used herein the terms "heteroaryl," and "heteroaromatic," refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein the term "heteroarylalkyl," refers to a heteroaryl group as previously defined that further includes a covalently attached $C_1$-$C_{12}$ alkyl radical. The alkyl radical portion of the resulting heteroarylalkyl group is capable of forming a covalent bond with a parent molecule. Examples include without limitation, pyridinylmethyl, pyrimidinylethyl, napthyridinylpropyl and the like. Heteroarylalkyl groups as used herein may optionally include further substituent groups on one or both of the heteroaryl or alkyl portions.

As used herein the term "heterocyclic radical" refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic radical typically includes at least one atom selected from sulfur, nitrogen or oxygen. Examples of heterocyclic radicals include, [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

As used herein the term "hydrocarbyl" includes radical groups that comprise C, O and H. Included are straight, branched and cyclic groups having any degree of saturation. Such hydrocarbyl groups can include one or more heteroatoms selected from N, O and S and can be further mono or poly substituted with one or more substituent groups.

As used herein the term "mono or poly cyclic structure" is meant to include all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. Mono or poly cyclic structures can be attached to parent molecules using various strategies such as directly through a ring atom, fused through multiple ring atoms, through a substituent group or through a bifunctional linking moiety.

As used herein the term "oxo" refers to the group (=O).

As used herein the term "protecting group," refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene's Protective Groups in Organic Synthesis, 4th edition, John Wiley & Sons, New York, 2007.

Groups can be selectively incorporated into oligomeric compounds as provided herein as precursors. For example an amino group can be placed into a compound as provided herein as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal et al., *Protocols for Oligonucleotide Conjugates*, Humana Press; New Jersey, 1994, 26, 1-72.

The term "orthogonally protected" refers to functional groups which are protected with different classes of protecting groups, wherein each class of protecting group can be removed in any order and in the presence of all other classes (see, Barany et al., *J. Am. Chem. Soc.*, 1977, 99, 7363-7365; Barany et al., *J. Am. Chem. Soc.*, 1980, 102, 3084-3095). Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

Examples of hydroxyl protecting groups include without limitation, acetyl, t-butyl, t-butoxymethyl, methoxymethyl, tetrahydropyranyl, 1-ethoxyethyl, 1-(2-chloroethoxyl)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl(trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Wherein more commonly used hydroxyl protecting groups include without limitation, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include without limitation, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyl-oxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include without limitation, triphenylmethyl (trityl), benzyl (Bn), and the like.

The compounds described herein contain one or more asymmetric centers and thus give rise to enantiomers, diastereomers, and other stereoisomeric forms that may be defined, in terms of absolute stereochemistry, as (R)— or (S)—, α or β, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions*, John Wiley & Sons, 1981. When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to limit a particular configuration unless the text so states.

The terms "substituent" and "substituent group," as used herein, are meant to include groups that are typically added to other groups or parent compounds to enhance desired properties or provide other desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound.

Substituent groups amenable herein include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=$NR_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)—($R_{cc}$), guanidinyl (—N($R_{bb}$)C(=N($R_{bb}$))N($R_{bb}$)($R_{cc}$)), amidinyl (—C(=$NR_{bb}$)N($R_{bb}$)($R_{cc}$) or —N($R_{bb}$)C(=$NR_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S—(O)$_2$$R_{bb}$). Wherein each $R_{aa}$, $R_{bb}$ and $R_{cc}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The terms "stable compound" and "stable structure" as used herein are meant to indicate a compound that is sufficiently robust to survive isolation to a useful degree of purity from a reaction mixture, and formulation into an efficacious therapeutic agent. Only stable compounds are contemplated herein.

As used herein, the term "nucleobase" refers to unmodified or naturally occurring nucleobases which include, but are not limited to, the purine bases adenine (A) and guanine (G), and the pyrimidine bases thymine (T), cytosine (C) and uracil (U).

As used herein the term "heterocyclic base moiety" refers to unmodified or naturally occurring nucleobases as well as modified or non-naturally occurring nucleobases and synthetic mimetics thereof (such as for example phenoxazines). In one embodiment, a heterocyclic base moiety is any heterocyclic system that contains one or more atoms or groups of atoms capable of hydrogen bonding to a heterocyclic base of a nucleic acid.

In certain embodiments, heterocyclic base moieties include without limitation modified nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein.

In certain embodiments, heterocyclic base moieties include without limitation tricyclic pyrimidines such as 1,3-diazaphenoxazine-2-one, 1,3-diazaphenothiazine-2-one and 9-(2-aminoethoxy)-1,3-diazaphenoxazine-2-one (G-clamp). Heterocyclic base moieties also include those in which the purine or pyrimidine base is replaced with other heterocycles, for example 7-deaza-adenine, 7-deazaguanosine, 2-aminopyridine and 2-pyridone. Further heterocyclic base moieties include without limitation those known to the art skilled (see for example: U.S. Pat. No. 3,687,808; Swayze et al., *The Medicinal Chemistry of Oligonucleotides* in Antisense a Drug Technology, Chapter 6, pages 143-182, Crooke, S. T., ed., 2008); *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-302). Modified polycyclic heterocyclic compounds useful as heterocyclic base moieties are disclosed in the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,681,941; 5,750,692; 5,763,588; 5,830,653; 6,005,096; and U.S. Patent Application Publication 20030158403, each of which is incorporated herein by reference in its entirety.

As used herein the term "sugar moiety" refers to naturally occurring sugars having a furanose ring, synthetic or non-naturally occurring sugars having a modified furanose ring and sugar surrogates wherein the furanose ring has been replaced with a cyclic ring system such as for example a morpholino or hexitol ring system or a non-cyclic sugar surrogate such as that used in peptide nucleic acids. Illustrative examples of sugar moieties useful in the preparation of oligomeric compounds include without limitation, (β-D-ribose, (β-D-2'-deoxyribose, substituted sugars (such as 2', 5' and bis substituted sugars), 4'-S-sugars (such as 4'-5-ribose, 4'-S-2'-deoxyribose and 4'-S-2'-substituted ribose), bicyclic modified sugars (such as the 2'-O—CH$_2$-4' or 2'-O—(CH$_2$)$_2$-4' bridged ribose derived bicyclic sugars) and sugar surrogates (such as for example when the ribose ring has been replaced with a morpholino, a hexitol ring system or an open non-cyclic system).

As used herein the term "sugar substituent group" refers to groups that are covalently attached to sugar moieties. In certain embodiments, examples of sugar substituent groups include without limitation 2'-F, 2'-allyl, 2'-amino, 2'-azido, 2'-OCF$_3$, 2'-O—C$_1$-C$_{10}$ alkyl, 2'-OCH$_3$, 2'-O(CH$_2$)—CH$_3$, 2'-OCH$_2$CH$_3$, 2'-O—(CH$_2$)$_2$CH$_3$, 2'-O—(CH$_2$)$_2$—O—CH$_3$ (MOE), 2'-O[(CH$_2$)$_n$O]$_m$CH$_3$, 2'-O(CH$_2$)$_2$ S CH$_3$, 2'-O—(CH$_2$)$_3$—N(R$_p$)(R$_q$), 2'-O(CH$_2$)$_n$NH$_2$, 2'-O—(CH$_2$)$_2$—O—N(R$_p$)(R$_q$), O(CH$_2$)$_n$ON[(CH$_2$)$_n$CH$_3$], 2'-O(CH$_2$)$_n$ONH$_2$, 2'-O—(CH$_2$)$_2$—O—(CH$_2$)$_2$—N(R$_p$)(R$_q$), 2'-O—CH$_2$C(=O)—N(R$_p$)(R$_q$), 2'-OCH$_2$C(=O)N(H)CH$_3$, 2'-O—CH$_2$C(=O)—N(H)—(CH$_2$)$_2$—N(R$_p$)(R$_q$) and 2'-O—CH$_2$—N(H)—C(=NR$_r$)[N(R$_p$)(R$_q$)], 5'-vinyl, 5'-methyl (R or S) and 4'-S wherein each R$_p$, R$_q$ and R$_r$ is, independently, H, substituted or unsubstituted C$_1$-C$_{10}$ alkyl or a protecting group and where n and m are from 1 to about 10. Further examples of modified sugar moieties include without limitation bicyclic sugars used in bicyclic nucleosides.

In certain embodiments, examples of sugar substituent groups include without limitation substituted silyl, an RNA cleaving group, a reporter group, an intercalator, a group for improving pharmacokinetic properties, or a group for improving the pharmacodynamic properties of an oligomeric compound, and other substituents having similar properties. In certain embodiments, oligomeric compounds include modifed nucleosides comprising 2'-MOE substituent groups (Baker et al., J. Biol. Chem., 1997, 272, 11944-12000). Such 2'-MOE substitution has been described as having improved binding affinity compared to unmodified nucleosides and to other modified nucleosides, such as 2'-O-methyl, 2'-O-propyl, and 2'-O-aminopropyl. Oligonucleotides having the 2'-MOE substituent also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

Sugar moieties can be substituted with combinations of sugar substituent groups including without limitation 2'-F-5'-methyl substituted nucleosides (see PCT International Application WO 2008/101157, published on Aug. 21, 2008 for other disclosed 5',2'-bis substituted nucleosides). Other combinations are also possible, including without limitation, replacement of the ribosyl ring oxygen atom with S and further substitution at the 2'-position (see published U.S. Patent Application US2005-0130923, published on Jun. 16, 2005) and 5'-substitution of a bicyclic nucleoside (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group).

As used herein, the term "nucleoside" refers to a nucleobase-sugar combination. The two most common classes of such nucleobases are purines and pyrimidines.

As used herein, the term nucleotide refers to a nucleoside further comprising a modified or unmodified phosphate internucleoside linking group or a non-phosphate internucleoside linking group. For nucleotides that include a pentofuranosyl sugar, the internucleoside linking group can be linked to either the 2', 3' or 5' hydroxyl moiety of the sugar. The phosphate and or a non-phosphate internucleoside linking groups are routinely used to covalently link adjacent nucleosides to one another to form a linear polymeric compound.

The term "nucleotide mimetic" as used herein is meant to include monomers that incorporate into oligomeric compounds with sugar and linkage surrogate groups, such as for example peptide nucleic acids (PNA) or morpholinos (linked by —N(H)—C(=O)—O—). In general, the heterocyclic base at each position is maintained for hybridization to a nucleic acid target but the sugar and linkage is replaced with surrogate groups that are expected to function similar to native groups but have one or more enhanced properties.

As used herein the term "nucleoside mimetic" is intended to include those structures used to replace the sugar and the base at one or more positions of an oligomeric compound. Examples of nucleoside mimetics include without limitation nucleosides wherein the heterocyclic base moiety is replaced with a phenoxazine moiety (for example the 9-(2-aminoethoxy)-1,3-diazaphenoxazine-2-one group, also referred to as a G-clamp which forms four hydrogen bonds when hybridized with a guanosine base) and further replacement of the sugar moiety with a group such as for example a morpholino, a cyclohexenyl or a bicyclo[3.1.0]hexyl.

As used herein the term "modified nucleoside" is meant to include all manner of modified nucleosides that can be incorporated into an oligomeric compound using oligomer synthesis. The term is intended to include modifications made to a nucleoside such as modified stereochemical configurations, one or more substitutions, and deletion of groups as opposed to the use of surrogate groups which are described elsewhere herein. The term includes nucleosides having a furanose sugar (or 4'-S analog) portion and can include a heterocyclic base or can be an abasic nucleoside. One group of representative modified nucleosides includes without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-S-2'-substituted ribonucleosides), bicyclic modified nucleosides (such as for example, bicyclic nucleosides wherein the sugar moiety has a 2'-O—CHR$_a$-4' bridging group, wherein R$_a$ is H, alkyl or substituted alkyl) and base modified nucleosides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as base and sugar modified nucleosides. These modifications are meant to be illustrative and not exhaustive as other modifications are known in the art and are also envisioned as possible modifications for the modified nucleosides described herein.

As used herein the term "monomer subunit" is meant to include all manner of monomer units that are amenable to oligomer synthesis with one preferred list including monomer subunits such as β-D-ribonucleosides, β-D-2'-deoxyribnucleosides, modified nucleosides, including substituted nucleosides (such as 2', 5' and bis substituted nucleosides), 4'-S-modified nucleosides, (such as 4'-S-ribonucleosides, 4'-S-2'-deoxyribonucleosides and 4'-S-2'-substituted ribonucleosides), bicyclic modified nucleosides (such as bicyclic nucleosides wherein the sugar moiety has a 2'-O—CHR$_a$-4' bridging group, wherein R$_a$ is H, alkyl or substituted alkyl), other modified nucleosides, nucleoside mimetics, nucleosides having sugar surrogates and the tricyclic nucleosides as provided herein.

As used herein the term "bicyclic nucleoside" refers to a nucleoside comprising at least a bicyclic sugar moiety. Examples of bicyclic nucleosides include without limitation nucleosides having a furanosyl sugar that comprises a bridge between two of the non-geminal carbons, preferably the 4' and the 2' carbon atoms. In certain embodiments, oligomeric compounds provided herein include one or more 4' to 2' bridged bicyclic nucleosides. Examples of such 4' to 2' bridged bicyclic nucleosides, include but are not limited to one of formulae: 4'-(CH$_2$)—O-2' (LNA); 4'-(CH$_2$)—S-2; 4'-(CH$_2$)$_2$—O-2' (ENA); 4'-CH(CH$_3$)—O-2' and 4'-C—H (CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N (OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N (R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya, et al., *J. Org. Chem.*, 2009, 74, 118-134); and 4'-CH$_2$—C(=CH$_2$)-2' (and analogs thereof see published International Application WO 2008/154401, published on Dec. 8, 2008). Further bicyclic nucleosides have been reported in published literature (see for example: Srivastava et al., *J. Am. Chem. Soc.*, 2007, 129(26) 8362-8379; Frieden et al., *Nucleic Acids Research*, 2003, 21, 6365-6372; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wahlestedt et al., *Proc. Natl. Acad. Sci. U.S.A.*, 2000, 97, 5633-5638; Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; U.S. Pat. Nos. 7,399,845; 7,053,207; 7,034,133; 6,794,499; 6,770,748; 6,670,461; 6,525,191; 6,268,490; U.S. Patent Publication Nos. US2008-0039618; US2007-0287831; US2004-0171570; U.S. patent applications, Ser. Nos. 12/129,154; 61/099,844; 61/097,787; 61/086,231; 61/056,564; 61/026,998; 61/026,995; 60/989, 574; International applications WO 2007/134181; WO 2005/021570; WO 2004/106356; WO 94/14226; and PCT International Applications Nos. PCT/US2008/068922; PCT/US2008/066154; and PCT/US2008/064591). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic nucleosides comprise a bridge between the 4' and the 2' carbon atoms of the pentofuranosyl sugar moiety including without limitation, bridges comprising 1 or from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—; wherein: x is 0, 1, or 2; n is 1, 2, 3, or 4; each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-J$_1$), or sulfoxyl (S(=O)-J$_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is, —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-(CH$_2$)—O-2' bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include those having a 4' to 2' bridge wherein such bridges include without limitation, α-L-4'-(CH$_2$)—O-2', β-D-4'-CH$_2$—O-2', 4'-(CH$_2$)$_2$—O-2', 4'-CH$_2$—O—N(R)-2', 4'-CH$_2$—N(R)—O-2', 4'-CH(CH$_3$)—O-2', 4'-CH$_2$—S-2', 4'-CH$_2$—N(R)-2', 4'-CH$_2$—CH(CH$_3$)-2', and 4'-(CH$_2$)$_3$-2', wherein R is H, a protecting group or $C_1$-$C_{12}$ alkyl.

In certain embodiments, bicyclic nucleosides have the formula:

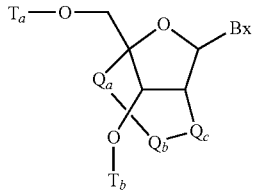

wherein:
Bx is a heterocyclic base moiety;
-Q$_a$-Q$_b$-Q$_c$- is —CH$_2$—N(R$_c$)—CH$_2$—, —C(=O)—N(R$_c$)—CH$_2$—, —CH$_2$—O—N(R$_c$)—, —CH$_2$—N(R$_c$)—O— or —N(R$_c$)—O—CH$_2$;
R$_c$ is $C_1$-$C_{12}$ alkyl or an amino protecting group; and
T$_a$ and T$_b$ are each, independently H, a hydroxyl protecting group, a conjugate group, a reactive phosphorus group, a phosphorus moiety or a covalent attachment to a support medium.

In certain embodiments, bicyclic nucleosides have the formula:

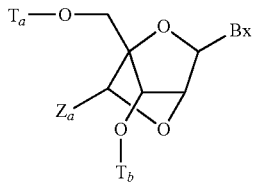

wherein:
Bx is a heterocyclic base moiety;
T$_a$ and T$_b$ are each, independently H, a hydroxyl protecting group, a conjugate group, a reactive phosphorus group, a phosphorus moiety or a covalent attachment to a support medium;
Z$_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, OJ$_c$, NJ$_c$J$_d$, SJ$_c$, N$_3$, OC(=X)J$_c$, and NJ$_e$C(=X)NJ$_c$J$_d$, wherein each J$_c$, J$_d$ and J$_e$ is, independently, H, $C_1$-$C_6$ alkyl, or substituted $C_1$-$C_6$ alkyl and X is O or NJ$_c$.

In certain embodiments, bicyclic nucleosides have the formula:

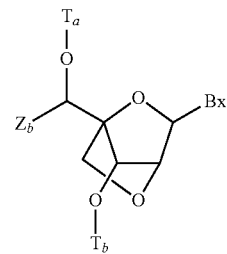

wherein:
Bx is a heterocyclic base moiety;
T$_a$ and T$_b$ are each, independently H, a hydroxyl protecting group, a conjugate group, a reactive phosphorus group, a phosphorus moiety or a covalent attachment to a support medium;
Z$_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides have the formula:

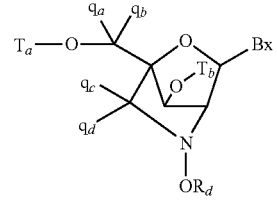

wherein:
Bx is a heterocyclic base moiety;
T$_a$ and T$_b$ are each, independently H, a hydroxyl protecting group, a conjugate group, a reactive phosphorus group, a phosphorus moiety or a covalent attachment to a support medium;
R$_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
each q$_a$, q$_b$, q$_c$ and q$_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

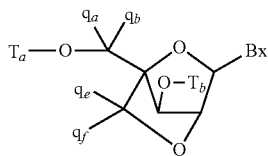

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-$CH_2$—O-2' bridge, along with their oligomerization, and nucleic acid recognition properties have been described (Koshkin et al., *Tetrahedron*, 1998, 54, 3607-3630). The synthesis of bicyclic nucleosides has also been described in WO 98/39352 and WO 99/14226.

Analogs of various bicyclic nucleosides that have 4' to 2' bridging groups such as 4'-$CH_2$—O-2' and 4'-$CH_2$—S-2', have also been prepared (Kumar et al., *Bioorg. Med. Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides have the formula:

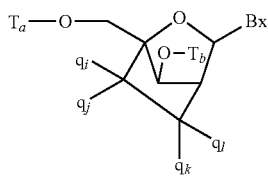

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-($CH_2$)$_3$-2' bridge and the alkenyl analog bridge 4'-CH=CH—$CH_2$-2' have been described (Frier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

In certain embodiments, bicyclic nucleosides include, but are not limited to, (A) α-L-methyleneoxy (4'-$CH_2$—O-2') BNA, (B)β-D-methyleneoxy (4'-$CH_2$—O-2') BNA, (C) ethyleneoxy (4'-($CH_2$)$_2$—O-2') BNA, (D) aminooxy (4'-$CH_2$—O—N(R)-2') BNA, (E) oxyamino (4'-$CH_2$—N(R)—O-2') BNA, (F) methyl(methyleneoxy) (4'-CH($CH_3$)—O-2') BNA (also referred to as constrained ethyl or cEt), (G) methylenethio (4'-$CH_2$—S-2') BNA, (H) methylene-amino (4'-$CH_2$—N(R)-2') BNA, (I) methyl carbocyclic (4'-$CH_2$—CH($CH_3$)-2') BNA, (J) propylene carbocyclic (4'-($CH_2$)$_3$-2') BNA, and (K) vinyl BNA as depicted below.

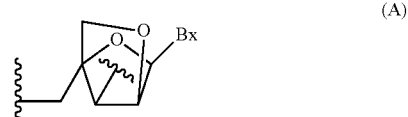

(A)

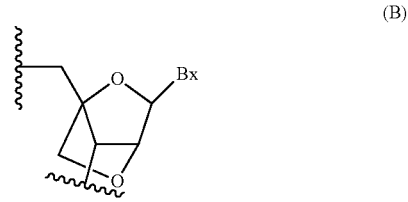

(B)

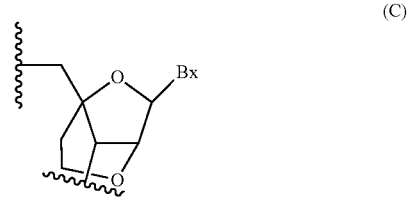

(C)

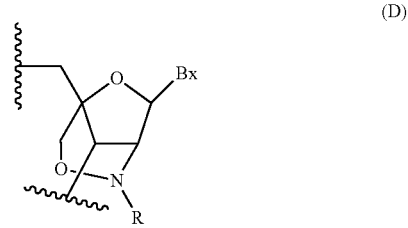

(D)

-continued (E) 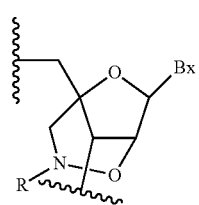

(F) 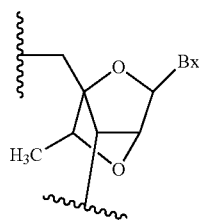

(G) 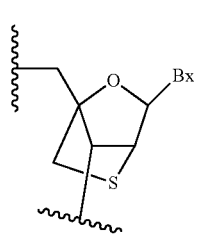

(H) 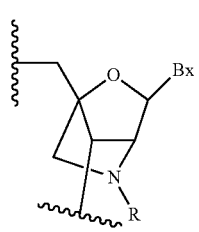

(I) 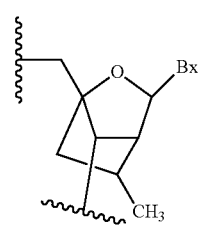

(J) 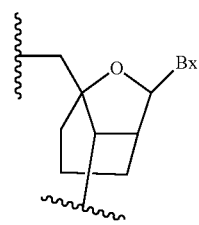

(K) 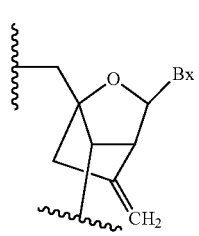

wherein Bx is the base moiety and R is, independently, H, a protecting group, $C_1$-$C_6$ alkyl or $C_1$-$C_6$ alkoxy.

As used herein the term "sugar surrogate" refers to replacement of the nucleoside furanose ring with a non-furanose (or 4'-substituted furanose) group with another structure such as another ring system or open system. Such structures can be as simple as a six membered ring as opposed to the five membered furanose ring or can be more complicated such as a bicyclic or tricyclic ring system or a non-ring system used in peptide nucleic acid. In certain embodiments, sugar surrogates include without limitation sugar surrogate groups such as morpholinos, cyclohexenyls and cyclohexitols. In general the heterocyclic base is maintained even when the sugar moiety is a sugar surrogate so that the resulting monomer subunit will be able to hybridize.

In certain embodiments, nucleosides having sugar surrogate groups include without limitation, replacement of the ribosyl ring with a sugar surrogate such as a tetrahydropyranyl ring system (also referred to as hexitol) as illustrated below:

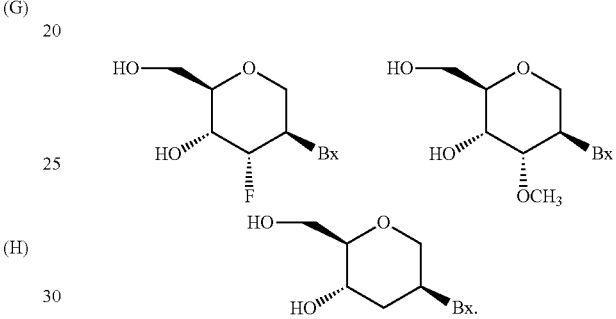

In certain embodiments, sugar surrogates are selected having the formula:

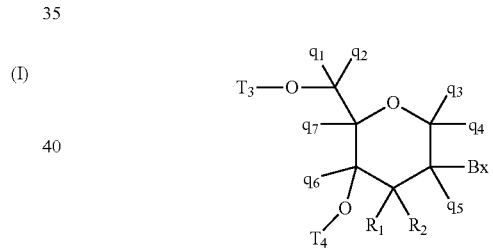

wherein:
Bx is a heterocyclic base moiety;
$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to an oligomeric compound or oligonucleotide and the other of $T_3$ and $T_4$ is H, a hydroxyl protecting group, a linked conjugate group or a 5' or 3'-terminal group; $q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and
one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F.

In certain embodiments, $R_1$ is fluoro and $R_2$ is H; $R_1$ is methoxy and $R_2$ is H, and $R_1$ is methoxyethoxy and $R_2$ is H.

Such sugar surrogates can be referred to as a "modified tetrahydropyran nucleoside" or "modified THP nucleoside". Modified THP nucleosides include, but are not limited to, what is referred to in the art as hexitol nucleic acid (HNA), altritol nucleic acid (ANA), and mannitol nucleic acid (MNA) (see Leumann, C. J., Bioorg. & Med. Chem., 2002, 10, 841-854).

In certain embodiments, oligomeric compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horvath et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., Acta Crystallographica, Section F: Structural Biology and Crystallization Communications, 2005, F61(6), 585-586; Gu et al., Tetrahedron, 2004, 60(9), 2111-2123; Gu et al., Oligonucleotides, 2003, 13(6), 479-489; Wang et al., *J. Org. Chem.*, 2003, 68, 4499-4505; Verbeure et al., Nucleic Acids Research, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

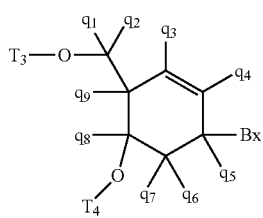

wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J. *Bioorg. & Med. Chem.*, 2002, 10, 841-854). Such ring systems can undergo various additional substitutions to further enhance their activity.

Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety.

The tricyclic nucleosides provided herein can be prepared by any of the applicable techniques of organic synthesis, as, for example, illustrated in the examples below. Many such techniques are well known in the art. However, many of the known techniques are elaborated in *Compendium of Organic Synthetic Methods*, John Wiley & Sons, New York: Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade Jr., 1980; Vol. 5, Leroy G. Wade Jr., 1984; and Vol. 6, Michael B. Smith; as well as March, J., *Advanced Organic Chemistry*, 3rd Edition, John Wiley & Sons, New York, 1985; *Comprehensive Organic Synthesis. Selectivity, Strategy & Efficiency in Modern Organic Chemistry*, in 9 Volumes, Barry M. Trost, Editor-in-Chief, Pergamon Press, New York, 1993; *Advanced Organic Chemistry, Part B: Reactions and Synthesis*, 4th Edition; Carey and Sundberg, Kluwer Academic/Plenum Publishers, New York, 2001; *Advanced Organic Chemistry, Reactions, Mechanisms, and Structure*, 2nd Edition, March, McGraw Hill, 1977; Greene, T. W., and Wutz, P. G. M., *Protecting Groups in Organic Synthesis*, 4th Edition, John Wiley & Sons, New York, 1991; and Larock, R. C., *Comprehensive Organic Transformations*, 2nd Edition, John Wiley & Sons, New York, 1999.

As used herein the term "reactive phosphorus" is meant to include groups that are covalently linked to a monomer subunit that can be further attached to an oligomeric compound that are useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. In certain embodiments, reactive phosphorus groups are selected from diisopropylcyanoethoxy phosphoramidite (—O—P[N[CH(CH$_3$)$_2$]$_2$]O(CH$_2$)$_2$CN) and H-phosphonate (—O—P(=O)(H)OH), wherein the O* is provided from the Markush group for the monomer. A preferred synthetic solid phase synthesis utilizes phosphoramidites ($P^{III}$ chemistry) as reactive phosphites. The intermediate phosphite compounds are subsequently oxidized to the phosphate or thiophosphate ($P^V$ chemistry) using known methods to yield, phosphodiester or phosphorothioate internucleoside linkages. Additional reactive phosphates and phosphites are disclosed in Tetrahedron Report Number 309 (Beaucage and Iyer, *Tetrahedron*, 1992, 48, 2223-2311).

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

The term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include without limitation, siloxane, sulfide, sulfoxide, sulfone, acetyl, formacetyl, thioformacetyl, methylene formacetyl, thioformacetyl, alkeneyl, sulfamate, methyleneimino, methylenehydrazino, sulfonate, sulfonamide, amide and others having mixed N, O, S and $CH_2$ component parts.

As used herein, the term "oligomeric compound" refers to a contiguous sequence of linked monomer subunits. Each linked monomer subunit normally includes a heterocyclic base moiety but monomer subunits also includes those without a heterocyclic base moiety such as abasic monomer subunits. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having one or a plurality of nucleoside mimetics and or nucleosides having sugar surrogate groups.

In certain embodiments, oligomeric compounds comprise a plurality of monomer subunits independently selected from naturally occurring nucleosides, non-naturally occurring nucleosides, modified nucleosides, nucleoside mimetics, and nucleosides having sugar surrogate groups. In certain embodiments, oligomeric compounds are single stranded. In certain embodiments, oligomeric compounds are double stranded comprising a double-stranded duplex. In certain embodiments, oligomeric compounds comprise one or more conjugate groups and/or terminal groups.

When preparing oligomeric compounds having specific motifs as disclosed herein it can be advantageous to mix non-naturally occurring monomer subunits such as the tricyclic nucleosides as provided herein with other non-naturally occurring monomer subunits, naturally occurring monomer subunits (nucleosides) or mixtures thereof. In certain embodiments, oligomeric compounds are provided herein comprising a contiguous sequence of linked monomer subunits wherein at least one monomer subunit is a tricyclic nucleoside as provided herein. In certain embodiments, oligomeric compounds are provided comprising a plurality of tricyclic nucleosides as provided herein.

Oligomeric compounds are routinely prepared linearly but can also be joined or otherwise prepared to be circular and/or can be prepared to include branching. Oligomeric compounds can form double stranded constructs such as for example two strands hybridized to form a double stranded composition. Double stranded compositions can be linked or separate and can include various other groups such as conjugates and/or overhangs on the ends.

As used herein, "antisense compound" refers to an oligomeric compound, at least a portion of which is at least partially complementary to a target nucleic acid to which it hybridizes. In certain embodiments, an antisense compound modulates (increases or decreases) expression or amount of a target nucleic acid. In certain embodiments, an antisense compound alters splicing of a target pre-mRNA resulting in a different splice variant. In certain embodiments, an antisense compound modulates expression of one or more different target proteins. Antisense mechanisms contemplated herein include, but are not limited to an RNase H mechanism, RNAi mechanisms, splicing modulation, translational arrest, altering RNA processing, inhibiting microRNA function, or mimicking microRNA function.

As used herein, "antisense activity" refers to any detectable and/or measurable activity attributable to the hybridization of an antisense compound to its target nucleic acid. In certain embodiments, such activity may be an increase or decrease in an amount of a nucleic acid or protein. In certain embodiments, such activity may be a change in the ratio of splice variants of a nucleic acid or protein. Detection and/or measuring of antisense activity may be direct or indirect. For example, in certain embodiments, antisense activity is assessed by detecting and/or measuring the amount of target protein or the relative amounts of splice variants of a target protein. In certain embodiments, antisense activity is assessed by detecting and/or measuring the amount of target nucleic acids and/or cleaved target nucleic acids and/or alternatively spliced target nucleic acids. In certain embodiments, antisense activity is assessed by observing a phenotypic change in a cell or animal.

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, and non-phosphorus containing internucleoside linking groups such as formacetyl and methyleneimino. Internucleoside linkages also includes neutral non-ionic internucleoside linkages such as amide-3 (3'-$CH_2$—C(=O)—N(H)-5'), amide-4 (3'-$CH_2$—N(H)—C(=O)-5') and methylphosphonate wherein a phosphorus atom is not always present.

In certain embodiments, oligomeric compounds as provided herein can be prepared having one or more internucleoside linkages containing modified e.g. non-naturally occurring internucleoside linkages. The two main classes of internucleoside linkages are defined by the presence or absence of a phosphorus atom. Modified internucleoside linkages having a phosphorus atom include without limitation, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus containing linkages include without limitation, U.S. Pat. Nos. 3,687,808; 4,469,863; 4,476,301; 5,023,243; 5,177,196; 5,188,897; 5,194,599; 5,264,423; 5,276,019; 5,278,302; 5,286,717; 5,321,131; 5,399,676; 5,405,939; 5,453,496; 5,455,233; 5,466,677; 5,476,925; 5,519,126; 5,527,899; 5,536,821; 5,541,306; 5,550,111; 5,563,253; 5,565,555; 5,571,799; 5,587,361; 5,625,050; 5,672,697 and 5,721,218, certain of which are commonly owned with this application, and each of which is herein incorporated by reference.

In certain embodiments, oligomeric compounds as provided herein can be prepared having one or more non-phosphorus containing internucleoside linkages. Such oligomeric compounds include without limitation, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include without limitation, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439; 5,646,269 and 5,792,608, certain of which are commonly owned with this application, and each of which is herein incorporated by reference.

As used herein "neutral internucleoside linkage" is intended to include internucleoside linkages that are nonionic. Neutral internucleoside linkages include without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

In certain embodiments, oligomeric compounds as provided herein can be prepared having one or more optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. No. 4,725,677 and Re. 34,069 (β-cyanoethyl); Beaucage et al., *Tetrahedron*, 1993, 49(10), 1925-1963; Beaucage et al., *Tetrahedron*, 1993, 49(46), 10441-10488; Beaucage et al., *Tetrahedron*, 1992, 48(12), 2223-2311.

As used herein the terms "linking groups" and "bifunctional linking moieties" are meant to include groups known in the art that are useful for attachment of chemical functional groups, conjugate groups, reporter groups and other groups to selective sites in a parent compound such as for example an oligomeric compound. In general, a bifunctional linking moiety comprises a hydrocarbyl moiety having two functional groups. One of the functional groups is selected to bind to a parent molecule or compound of interest and the other is selected to bind to essentially any selected group such as a chemical functional group or a conjugate group. In some embodiments, the linker comprises a chain structure or a polymer of repeating units such as ethylene glycols or amino acid units. Examples of functional groups that are routinely used in a bifunctional linking moieties include without limitation, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include without limitation, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, the oligomeric compounds as provided herein can be modified by covalent attachment of one or more conjugate groups. In general, conjugate groups modify one or more properties of the oligomeric compounds they are attached to. Such oligonucleotide properties include without limitation, pharmacodynamics, pharmacokinetics, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

In certain embodiments, the oligomeric compounds as provided herein can be modified by covalent attachment of one or more terminal groups to the 5' or 3'-terminal groups. A terminal group can also be attached at any other position at one of the terminal ends of the oligomeric compound. As used herein the terms "5'-terminal group", "3'-terminal group", "terminal group" and combinations thereof are meant to include useful groups known to the art skilled that can be placed on one or both of the terminal ends, including but not limited to the 5' and 3'-ends of an oligomeric compound respectively, for various purposes such as enabling the tracking of the oligomeric compound (a fluorescent label or other reporter group), improving the pharmacokinetics or pharmacodynamics of the oligomeric compound (such as for example: uptake and/or delivery) or enhancing one or more other desirable properties of the oligomeric compound (a group for improving nuclease stability or binding affinity). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups.

As used herein the term "phosphate moiety" refers to a terminal phosphate group that includes phosphates as well as modified phosphates. The phosphate moiety can be located at either terminus but is preferred at the 5'-terminal nucleoside. In one aspect, the terminal phosphate is unmodified having the formula —O—P(=O)(OH)OH. In another aspect, the terminal phosphate is modified such that one or more of the O and OH groups are replaced with H, O, S, N(R) or alkyl where R is H, an amino protecting group or unsubstituted or substituted alkyl. In certain embodiments, the 5' and or 3' terminal group can comprise from 1 to 3 phosphate moieties that are each, independently, unmodified (di or tri-phosphates) or modified.

As used herein, the term "phosphorus moiety" refers to a group having the formula:

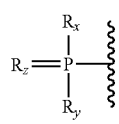

wherein:

$R_x$ and $R_y$ are each, independently, hydroxyl, protected hydroxyl group, thiol, protected thiol group, $C_1$-$C_6$ alkyl, substituted $C_1$-$C_6$ alkyl, $C_1$-$C_6$ alkoxy, substituted $C_1$-$C_6$ alkoxy, a protected amino or substituted amino; and $R_z$ is O or S.

As a monomer such as a phosphoramidite or H-phosphonate the protected phosphorus moiety is preferred to maintain stability during oligomer synthesis. After incorporation into an oligomeric compound the phosphorus moiety can include deprotected groups.

Phosphorus moieties included herein can be attached to a monomer, which can be used in the preparation of oligomeric compounds, wherein the monomer may be attached using O, S, $NR_d$ or $CR_eR_f$, wherein $R_d$ includes without limitation H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl, and $R_e$ and $R_f$ each, independently, include without limitation H, halogen, $C_1$-$C_6$ alkyl, substituted $C_1$-$C_6$ alkyl, $C_1$-$C_6$ alkoxy or substituted $C_1$-$C_6$ alkoxy. Such linked phosphorus moieties include without limitation, phosphates, modified phosphates, thiophosphates, modified thiophosphates, phosphonates, modified phosphonates, phosphoramidates and modified phosphoramidates.

RNA duplexes exist in what has been termed "A Form" geometry while DNA duplexes exist in "B Form" geometry. In general, RNA:RNA duplexes are more stable, or have higher melting temperatures ($T_m$) than DNA:DNA duplexes (Sanger et al., *Principles of Nucleic Acid Structure*, 1984, Springer-Verlag; New York, N.Y.; Lesnik et al., *Biochemistry*, 1995, 34, 10807-10815; Conte et al., *Nucleic Acids Res.*, 1997, 25, 2627-2634). The increased stability of RNA has been attributed to several structural features, most notably the improved base stacking interactions that result from an A-form geometry (Searle et al., *Nucleic Acids Res.*, 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., *Biochemistry*, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.).

The relative ability of a chemically-modified oligomeric compound to bind to complementary nucleic acid strands, as compared to natural oligonucleotides, is measured by obtaining the melting temperature of a hybridization complex of said chemically-modified oligomeric compound with its complementary unmodified target nucleic acid. The melting temperature ($T_m$), a characteristic physical property of double helices, denotes the temperature in degrees centigrade at which 50% helical versus coiled (unhybridized) forms are present. $T_m$ (also commonly referred to as binding affinity) is measured by using the UV spectrum to determine the formation and breakdown (melting) of hybridization. Base stacking, which occurs during hybridization, is accompanied by a reduction in UV absorption (hypochromicity). Consequently a reduction in UV absorption indicates a higher $T_m$.

It is known in the art that the relative duplex stability of an antisense compound:RNA target duplex can be modulated through incorporation of chemically-modified nucleosides into the antisense compound. Sugar-modified nucleosides have provided the most efficient means of modulating the $T_m$ of an antisense compound with its target RNA. Sugar-modified nucleosides that increase the population of or lock the sugar in the C3'-endo (Northern, RNA-like sugar pucker) configuration have predominantly provided a per modification $T_m$ increase for antisense compounds toward a complementary RNA target. Sugar-modified nucleosides that increase the population of or lock the sugar in the C2'-endo (Southern, DNA-like sugar pucker) configuration predominantly provide a per modification Tm decrease for antisense compounds toward a complementary RNA target. The sugar pucker of a given sugar-modified nucleoside is not the only factor that dictates the ability of the nucleoside to increase or decrease an antisense compound's $T_m$ toward complementary RNA. For example, the sugar-modified nucleoside tricycloDNA is predominantly in the C2'-endo conformation, however it imparts a 1.9 to 3° C. per modification increase in $T_m$ toward a complementary RNA. Another example of a sugar-modified high-affinity nucleoside that does not adopt the C3'-endo conformation is α-L-LNA (described in more detail herein).

As used herein, "$T_m$" means melting temperature which is the temperature at which the two strands of a duplex nucleic acid separate. $T_m$ is often used as a measure of duplex stability or the binding affinity of an antisense compound toward a complementary RNA molecule.

As used herein, "complementarity" in reference to nucleobases refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases or more broadly, heterocyclic base moieties, comprising certain modifications may maintain the ability to pair with a counterpart nucleobase and thus, are still capable of complementarity.

As used herein, "non-complementary" in reference to nucleobases refers to a pair of nucleobases that do not form hydrogen bonds with one another or otherwise support hybridization.

As used herein, "complementary" in reference to linked nucleosides, oligonucleotides, oligomeric compounds, or nucleic acids, refers to the capacity of an oligomeric compound to hybridize to another oligomeric compound or nucleic acid through nucleobase or more broadly, heterocyclic base, complementarity. In certain embodiments, an antisense compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are antisense compounds that may comprise up to about 20% nucleotides that are mismatched (i.e., are not nucleobase complementary to the corresponding nucleotides of the target). Preferably the antisense compounds contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid.

It is understood in the art that the sequence of an oligomeric compound need not be 100% complementary to that of its target nucleic acid to be specifically hybridizable. Moreover, an oligomeric compound may hybridize over one or more segments such that intervening or adjacent segments are not involved in the hybridization event (e.g., a loop structure or hairpin structure). In certain embodiments, oligomeric compounds can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within this scope. Percent complementarity of an oligomeric compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

As used herein, "hybridization" refers to the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, "target nucleic acid" refers to any nucleic acid molecule the expression, amount, or activity of which is capable of being modulated by an antisense compound. In certain embodiments, the target nucleic acid is DNA or RNA. In certain embodiments, the target RNA is mRNA, pre-mRNA, non-coding RNA, pri-microRNA, pre-microRNA, mature microRNA, promoter-directed RNA, or natural antisense transcripts. For example, the target nucleic acid can be a cellular gene (or mRNA transcribed from the gene) whose expression is associated with a particular disorder or disease state, or a nucleic acid molecule from an infectious agent. In certain embodiments, target nucleic acid is a viral or bacterial nucleic acid.

Further included herein are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds provided herein may elicit the action of one or more enzymes or structural proteins to effect modification of the target nucleic acid. Alternatively, the oligomeric compound may inhibit the activity the target nucleic acid through an occupancy-based method, thus interfering with the activity of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

As used herein, "modulation" refers to a perturbation of amount or quality of a function or activity when compared to the function or activity prior to modulation. For example, modulation includes the change, either an increase (stimulation or induction) or a decrease (inhibition or reduction) in gene expression. As a further example, modulation of expression can include perturbing splice site selection of pre-mRNA processing, resulting in a change in the amount of a particular splice-variant present compared to conditions that were not perturbed. As a further example, modulation includes perturbing translation of a protein.

As used herein, the term "pharmaceutically acceptable salts" refers to salts that retain the desired activity of the compound and do not impart undesired toxicological effects thereto. The term "pharmaceutically acceptable salt" includes a salt prepared from pharmaceutically acceptable non-toxic acids or bases, including inorganic or organic acids and bases.

Pharmaceutically acceptable salts of the oligomeric compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the oligomeric compounds described herein are in the form of a sodium salt.

In certain embodiments, oligomeric compounds provided herein comprise from about 8 to about 80 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 monomer subunits in length, or any range therewithin.

In certain embodiments, oligomeric compounds provided herein comprise from about 8 to 40 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monomer subunits in length, or any range therewithin.

In certain embodiments, oligomeric compounds provided herein comprise from about 8 to 20 monomer subunits in length. One having ordinary skill in the art will appreciate that this embodies oligomeric compounds of 8, 9, 10, 11, 12, 13, 14, 15, 16, 17, 18, 19 or 20 monomer subunits in length, or any range therewithin.

In certain embodiments, oligomeric compounds provided herein comprise from about 8 to 16 monomer subunits in length. One having ordinary skill in the art will appreciate that this embodies oligomeric compounds of 8, 9, 10, 11, 12, 13, 14, 15 or 16 monomer subunits in length, or any range therewithin.

In certain embodiments, oligomeric compounds provided herein comprise from about 10 to 14 monomer subunits in length. One having ordinary skill in the art will appreciate that this embodies oligomeric compounds of 10, 11, 12, 13 or 14 monomer subunits in length, or any range therewithin.

In certain embodiments, oligomeric compounds provided herein comprise from about 10 to 18 monomer subunits in length. One having ordinary skill in the art will appreciate that this embodies oligomeric compounds of 10, 11, 12, 13, 14, 15, 16, 17 or 18 monomer subunits in length, or any range therewithin.

In certain embodiments, oligomeric compounds provided herein comprise from about 10 to 21 monomer subunits in length. One having ordinary skill in the art will appreciate that this embodies oligomeric compounds of 10, 11, 12, 13, 14, 15, 16, 17, 18, 19, 20 or 21 monomer subunits in length, or any range therewithin.

In certain embodiments, oligomeric compounds provided herein comprise from about 12 to 14 monomer subunits in length. One having ordinary skill in the art will appreciate that this embodies oligomeric compounds of 12, 13 or 14 monomer subunits in length, or any range therewithin.

In certain embodiments, oligomeric compounds provided herein comprise from about 12 to 18 monomer subunits in length. One having ordinary skill in the art will appreciate that this embodies oligomeric compounds of 12, 13, 14, 15, 16, 17 or 18 monomer subunits in length, or any range therewithin.

In certain embodiments, oligomeric compounds provided herein comprise from about 12 to 21 monomer subunits in length. One having ordinary skill in the art will appreciate that this embodies oligomeric compounds of 12, 13, 14, 15, 16, 17, 18, 19, 20 or 21 monomer subunits in length, or any range therewithin.

In certain embodiments, oligomeric compounds provided herein comprise from about 14 to 18 monomer subunits in length. One having ordinary skill in the art will appreciate that this embodies oligomeric compounds of 14, 15, 16, 17 or 18 monomer subunits in length, or any range therewithin.

In certain embodiments, oligomeric compounds of any of a variety of ranges of lengths of linked monomer subunits are provided. In certain embodiments, oligomeric compounds are provided consisting of X-Y linked monomer subunits, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, this provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-27, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomer subunits.

In certain embodiments, the ranges for the oligomeric compounds listed herein are meant to limit the number of monomer subunits in the oligomeric compounds, however such oligomeric compounds may further include 5' and/or 3'-terminal groups including but not limited to protecting groups such as hydroxyl protecting groups, optionally linked conjugate groups and/or other substituent groups.

In certain embodiments, the preparation of oligomeric compounds as disclosed herein is performed according to literature procedures for DNA: Protocols for Oligonucleotides and Analogs, Agrawal, Ed., Humana Press, 1993, and/or RNA: Scaringe, *Methods*, 2001, 23, 206-217; Gait et al., *Applications of Chemically synthesized RNA in RNA:Protein Interactions*, Smith, Ed., 1998, 1-36; Gallo et al., *Tetrahedron*, 2001, 57, 5707-5713. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. No. 4,725,677 and Re. 34,069.

Oligomeric compounds are routinely prepared using solid support methods as opposed to solution phase methods. Commercially available equipment commonly used for the preparation of oligomeric compounds that utilize the solid support method is sold by several vendors including, for example, Applied Biosystems (Foster City, Calif.). Any other means for such synthesis known in the art may additionally or alternatively be employed. Suitable solid phase techniques, including automated synthesis techniques, are described in

*Oligonucleotides and Analogues, a Practical Approach*, F. Eckstein, Ed., Oxford University Press, New York, 1991.

The synthesis of RNA and related analogs relative to the synthesis of DNA and related analogs has been increasing as efforts in RNA interference and micro RNA increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl](FPMP), 2'-O-[(triisopropylsilyl)oxy]methyl (2'-O—CH$_2$—O—Si(iPr)$_3$ (TOM) and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS: 5'-O-DMT-2'-O-t-butyldimethylsilyl; TOM: 2'-O-[triisopropylsilyl)oxy]methyl; DOD/ACE: (5'-O-bis(trimethylsiloxy)cyclododecyloxysilyl ether-2'-O-bis(2-acetoxyethoxy)methyl; and FPMP: 5'-O-DMT-2'-O-[1(2-fluorophenyl)-4-ethoxypiperidin-4-yl]. In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed herein in further investigative studies of the function of the peptide, or for use as a research, diagnostic, or therapeutic agent. In the case of oligomeric compounds targeted to microRNA, candidate modulators may be evaluated by the extent to which they increase the expression of a microRNA target RNA or protein (as interference with the activity of a microRNA will result in the increased expression of one or more targets of the microRNA).

As used herein, "expression" refers to the process by which a gene ultimately results in a protein. Expression includes, but is not limited to, transcription, splicing, post-transcriptional modification, and translation.

Suitable target segments may also be combined with their respective complementary oligomeric compounds provided herein to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature*, 1998, 391, 806-811; Timmons and Fire, *Nature*, 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.*, 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The oligomeric compounds provided herein can also be applied in the areas of drug discovery and target validation. In certain embodiments, provided herein is the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with one or more oligomeric compounds provided herein, measuring the nucleic acid or protein level of the target and/or a related phenotypic or chemical endpoint at some time after treatment, and optionally comparing the measured value to a non-treated sample or sample treated with a further oligomeric compound as provided herein. These methods can also be performed in parallel or in combination with other experiments to determine the function of unknown genes for the process of target validation or to determine the validity of a particular gene product as a target for treatment or prevention of a particular disease, condition, or phenotype. In certain embodiments, oligomeric compounds are provided for use in therapy. In certain embodiments, the therapy is reducing target messenger RNA.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds are provided herein that may have a higher affinity for target RNAs than does non-modified DNA. In certain such embodiments, higher affinity in turn provides increased potency allowing for the administration of lower doses of such compounds, reduced potential for toxicity, improvement in therapeutic index and decreased overall cost of therapy.

Effect of nucleoside modifications on RNAi activity is evaluated according to existing literature (Elbashir et al., *Nature*, 2001, 411, 494-498; Nishikura et al., *Cell*, 2001, 107, 415-416; and Bass et al., *Cell*, 2000, 101, 235-238.)

In certain embodiments, oligomeric compounds provided herein can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. In certain embodiments, oligomeric compounds provided herein can be utilized either alone or in combination with other oligomeric compounds or other therapeutics as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of oligomeric compounds as provided herein, particularly the primers and probes, with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

In certain embodiments, the tricyclic oligomeric compounds disclosed herein may be used treat a disease or condition. In certain embodiments, the oligomeric compounds disclosed herein may be used to ameliorate one or more symptoms of a disease or condition. In certain embodiments, a tricyclic nucleoside monomer may be used as an anti-viral agent. In certain embodiments, a tricyclic nucleoside monomer may be used ameliorate one or more symptoms caused by a virus. In certain embodiments, a tricyclic nucleoside monomer, a salt thereof, or a mono-, di-, or tri-phosphate analog thereof, may be used as an anti-viral agent. In certain embodiments, a tricyclic nucleoside monomer, a salt thereof, or a mono-, di-, or tri-phosphate analog thereof, may be used ameliorate one or more symptoms caused by a virus.

As one nonlimiting example, expression patterns within cells or tissues treated with one or more of the oligomeric compounds provided herein are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. USA*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

Those skilled in the art, having possession of the present disclosure will be able to prepare oligomeric compounds, comprising a contiguous sequence of linked monomer subunits, of essentially any viable length to practice the methods disclosed herein. Such oligomeric compounds will include at least one and preferably a plurality of the tricyclic nucleosides provided herein and may also include other monomer subunits including but not limited to nucleosides, modified nucleosides, nucleosides comprising sugar surrogate groups and nucleoside mimetics.

While in certain embodiments, oligomeric compounds provided herein can be utilized as described, the following examples serve only to illustrate and are not intended to be limiting.

EXAMPLES

General $^1$H and $^{13}$C NMR spectra were recorded on a 300 MHz and 75 MHz Bruker spectrometer, respectively.

Example 1

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 2

Synthesis of Oligomeric Compounds

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P=O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M NH$_4$OAc solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. Nos. 5,610,289 or 5,625,050.

Phosphoramidite internucleoside linkages can be prepared as described in U.S. Pat. No. 5,256,775 or 5,366,878.

Alkylphosphonothioate internucleoside linkages can be prepared as described in published PCT applications PCT/

US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378, 825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Pat. No. 5,223,618.

Example 3

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M NH$_4$OAc with >3 volumes of ethanol. Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligomeric compounds are purified by HPLC, as described by Chiang et al., J. Biol. Chem. 1991, 266, 18162-18171. Results obtained with HPLC-purified material are generally similar to those obtained with non-HPLC purified material.

Example 4

Synthesis of Oligomeric Compounds Using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, N.J.). Non-standard nucleosides are synthesized as per standard or patented methods and can be functionalized as base protected beta-cyanoethyldiisopropyl phosphoramidites.

Oligomeric compounds can be cleaved from support and deprotected with concentrated NH$_4$OH at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5

Analysis of Oligomeric Compounds Using the 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6

In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with one or more oligomeric compounds. The oligomeric compound is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 µg/mL per 100 nM oligomeric compound(s). This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

Example 7

Real-time Quantitative PCR Analysis of Target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 8

Analysis of Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 9

Design of Phenotypic Assays and in Vivo Studies for the use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Example 10

RNA Isolation

Poly(A)+mRNA Isolation

Poly(A)+mRNA is isolated according to Miura et al., (Clin. Chem., 1996, 42, 1758-1764). Other methods for poly (A)+mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL it of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL it of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11

Target-specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

```
                                          (SEQ ID NO: 2)
Forward primer: AATGGCTAAGTGAAGATGACAATCAT (SEQ ID NO: 3)
Reverse primer: TGCACATATCATTACACCAGTTCGT
```

And the PCR probe:

```
                                          (SEQ ID NO: 4)
FAM-TTGCAGCAATTCACTGTAAAGCTGGAAAGG-TAMRA,
``` where FAM is the fluorescent dye and TAMRA is the quencher dye.

Example 12

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 13

Preparation of Compound 6

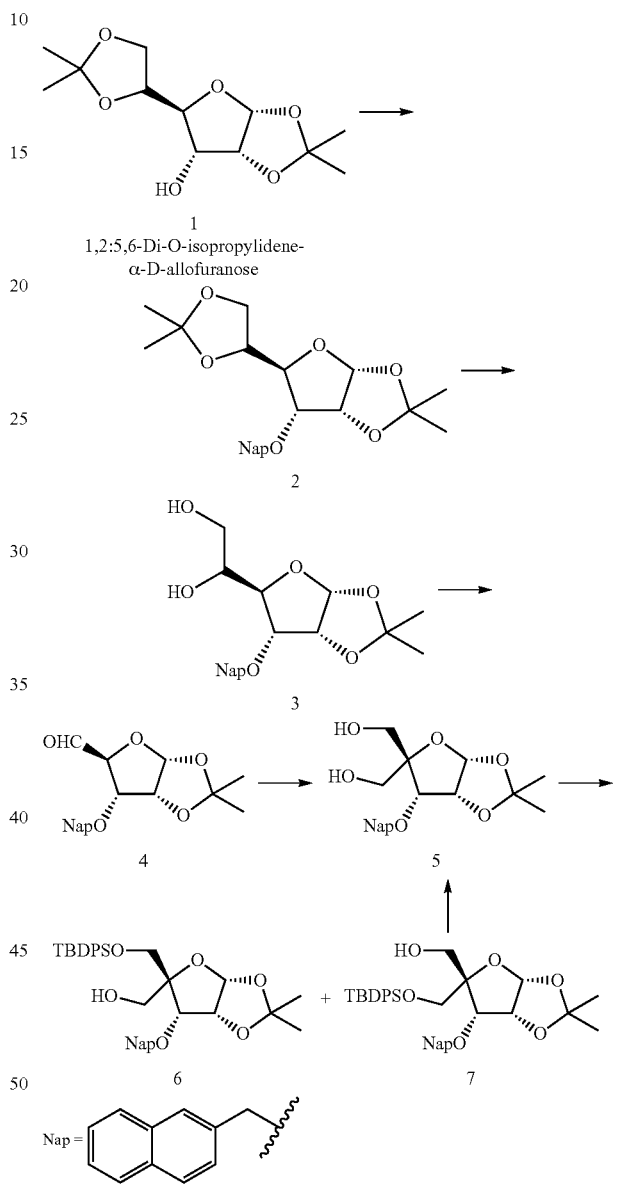

a) Preparation of Compound 2

Commercially available 1,2;5,6-di-O-isopropylidene-α-D-allofuranose, Compound 1, (135 g, 519.0 mmol) and 2-(bromomethyl)-naphthalene (126 g, 570.0 mmol) were dissolved in DMF (500 mL) in a three-necked flask (500 mL) and the reaction was cooled in an ice bath. Sodium hydride (60% w/w, 29 g, 727.0 mmol) was carefully added (6 g portions every 10 minutes) to the reaction and the stirring was continued for another 60 minutes after the addition was complete. At this time TLC analysis showed complete consumption of Compound 1. The reaction was carefully poured onto crushed ice (ca. 500 g) and the resulting slurry was stirred vigorously until all the ice melted. The resulting off-white solid was collected by filtration and suspended in water. The suspension was stirred vigorously using a mechanical stirrer for 30 minutes after which the solid was collected by filtration and suspended in hexanes. The suspension was stirred vigorously for 30 minutes after which the solid was collected by filtration and air dried for 4-6 hours and then dried under high vacuum over $P_2O_5$ for 16 hours to provide Compound 2 (206.0 g, 99%) as an off-white solid.

Compound 2: $^1$H NMR (300 MHz, CDCl$_3$): δ 7.85 (m, 4H), 7.48 (m, 3H), 5.74 (s, 1H), 4.92 (d, 1H, J=11.7), 4.75 (d, 1H, J=11.6), 4.58 (m, 1H), 4.36 (m, 1H), 4.15 (m, 1H), 4.03-3.86 (m, 3H), 1.61 (s, 3H), 1.36 (s, 9H).

b) Preparation of Compound 3

Compound 2 (200.0 g, 0.5 moles) was added in small portions to a solution of acetic acid (2.2 L) and water (740 mL). The reaction was stirred at room temperature for 16 h after which, TLC analysis (30% EtOAc/hexanes) indicated complete consumption of Compound 2. The reaction was then concentrated under reduced pressure until most of the acetic acid was removed. The remaining solution was poured into a stirred mixture of EtOAc (1 L) and water (1 L). Solid KOH was then added to the above mixture until the aqueous layer was strongly basic (pH>12). The organic layer was then separated, washed with saturated sodium bicarbonate solution, brine, dried (Na$_2$SO$_4$), filtered and concentrated under reduced pressure to provide Compound 3 as a yellow foam, which was used without any further purification.

c) Preparation of Compound 4

A solution of NaIO$_4$ (107.0 g) in water (3 L) was added over 40 minutes to a stirred (mechanical stirrer) solution of Compound 3 (crude from above) in dioxane (1.5 L) After 60 minutes the reaction mixture was poured into EtOAc (1.5 L) and the organic layer was separated, washed with water (1 L), brine (1 L), dried (Na$_2$SO$_4$) and concentrated to provide Compound 4 as a yellow oil, which was used without any further purification.

d) Preparation of Compound 5

Compound 4 (crude from above) was dissolved in a mixture of THF (500) and water (500 mL) and the reaction was cooled in an ice bath. 2N NaOH (600 mL) and formaldehyde (250 mL of a 37% aqueous solution) were added to the reaction and the stirring was continued at room temperature for 3 days. The reaction was then poured into EtOAc (1 L) and washed with water (1 L), brine (1 L) and evaporated under reduced pressure until approximately 200 mL of EtOAc was left (a white precipitate was formed in the process). Hexanes (300 mL) was added to the precipitate and the mixture was allowed to stand for 16 hours after which the white solid was collected by filtration, washed with hexanes and dried under high vacuum over $P_2O_5$ to provide Compound 5 as a white solid (124 g, 66% from Compound 2).

Compound 5: $^1$H NMR (300 MHz, CDCl$_3$): δ 7.85 (m, 4H), 7.48 (m, 3H), 5.75 (d, 1H, J=3.9), 4.96 (d, 1H, J=11.8), 4.75 (d, 1H, J=11.8), 4.66 (m, 1H), 4.26 (d, 1H, J=5.2), 3.95 (m, 2H), 3.79 (m, 1H), 3.63 (m, 1H), 2.39 (m, 1H, OH), 1.66 (s, 3H), 1.34 (s, 3H).

e) Preparation of Compounds 6 and 7 tert-Butyldiphenylchlorosilane (305.0 mmol, 84.0 mL) was added to a cold (0° C.) stirring solution of Compound 5 (278.0 mmol, 100.0 g) and triethylamine (305 mmol, 43.0 mL) in dichloromethane (600 mL). After the addition was complete, the reaction was warmed to room temperature and the stirring was continued for 16 hours. MeOH (50 mL) was added (to quench the excess TBDPSC1) to the reaction and the stirring was continued for another 2 hours at room temperature. The reaction was then diluted with chloroform and the organic layer was washed with 10% HCl, saturated NaHCO$_3$, brine, dried (Na$_2$SO$_4$) and concentrated to provide a thick oil. Hexanes (150 mL) was added to the oil and the mixture was sonicated until a solution resulted. The solution was now seeded with a small amount of Compound 6 (previously isolated by column chromatography). After standing for 16 hours additional hexanes was added to the thick slurry and the solid was collected by filtration. The solid was then resuspended in hexanes and stirred vigorously for 30 minutes. The solid was collected by filtration to provide Compound 6 (80.5, 48% g) after drying under high vacuum for 16 hours. The filtrates were combined and concentrated under reduced pressure. The resulting oil was redissolved in minimum amount of hexanes and passed through a plug of silica gel (eluting with 20% EtOAc in hexanes). Fractions containing Compound 6 were combined, concentrated and crystallized as described above to provide a second crop of Compound 6 (20 g, 12%) as a white solid. Further elution of the silica gel plug with 50% EtOAc in hexanes provided pure Compound 6 (40.0 g, 24%) as a thick oil. In addition, a mixture of Compounds 6 and 7 (ca 15 g, 9%) was also isolated as a thick oil.

Compound 6: $^1$H NMR (300 MHz, CDCl$_3$): δ 7.83 (m, 4H), 7.56 (m, 7H), 7.30 (m, 6H), 5.80 (s, 1H), 4.97 (d, 1H, J=11.4), 4.70 (m, 2H), 4.46 (m, 1H), 3.92-3.66 (m, 4H), 2.39 (m, 1H, OH), 1.67 (s, 3H), 1.37 (s, 3H), 0.92 (s, 9H).

Compound 7: $^1$H NMR (300 MHz, CDCl$_3$): δ 7.9-7.3 (m, 17H), 5.71 (d, 1H, J=3.9), 4.86 (d, 1H, J=12.2), 4.74 (d, 1H, J=12.2), 4.56 (m, 1H), 4.22 (d, 1H, J=11.1), 4.18 (m, 1H), 4.07 (d, 1H, J=11.1), 4.02 (dd, 1H, J=4.2, 12.0), 3.64 (dd, 1H, J=9.4, 11.9), 1.89 (m, 1H), 1.25 (s, 6H), 1.05 (s, 9H).

f) Recover Compound 5 from Compound 7

Tetrabutylammonium fluoride (70 mL of a 1M solution in THF) was added to a cold (0° C.) stirring solution of Compound 7 (62.7 mmol, 37.5 g) in THF (250 mL) after which, the reaction was allowed to warm to room temperature gradually. After stirring for an additional 72 hours, the reaction was concentrated under vacuum and the residue was poured onto crushed ice. The flask was rinsed with some additional THF (3×) and added to the above suspension. The supernatant was removed by decantation and the solid at the bottom was added to a stirring mixture of hexanes (200 mL) and water (200 mL). After stirring for 2 hours, the flocculent solid was collected by filtration, washed with additional water and hexanes and dried under high vacuum to provide Compound 5 (20 g, 89%) as a white solid.

Example 14

Preparation of Compound 21

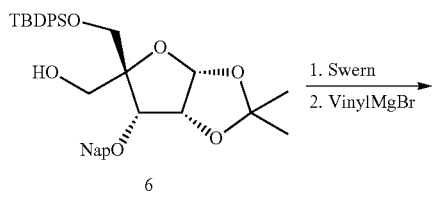

6

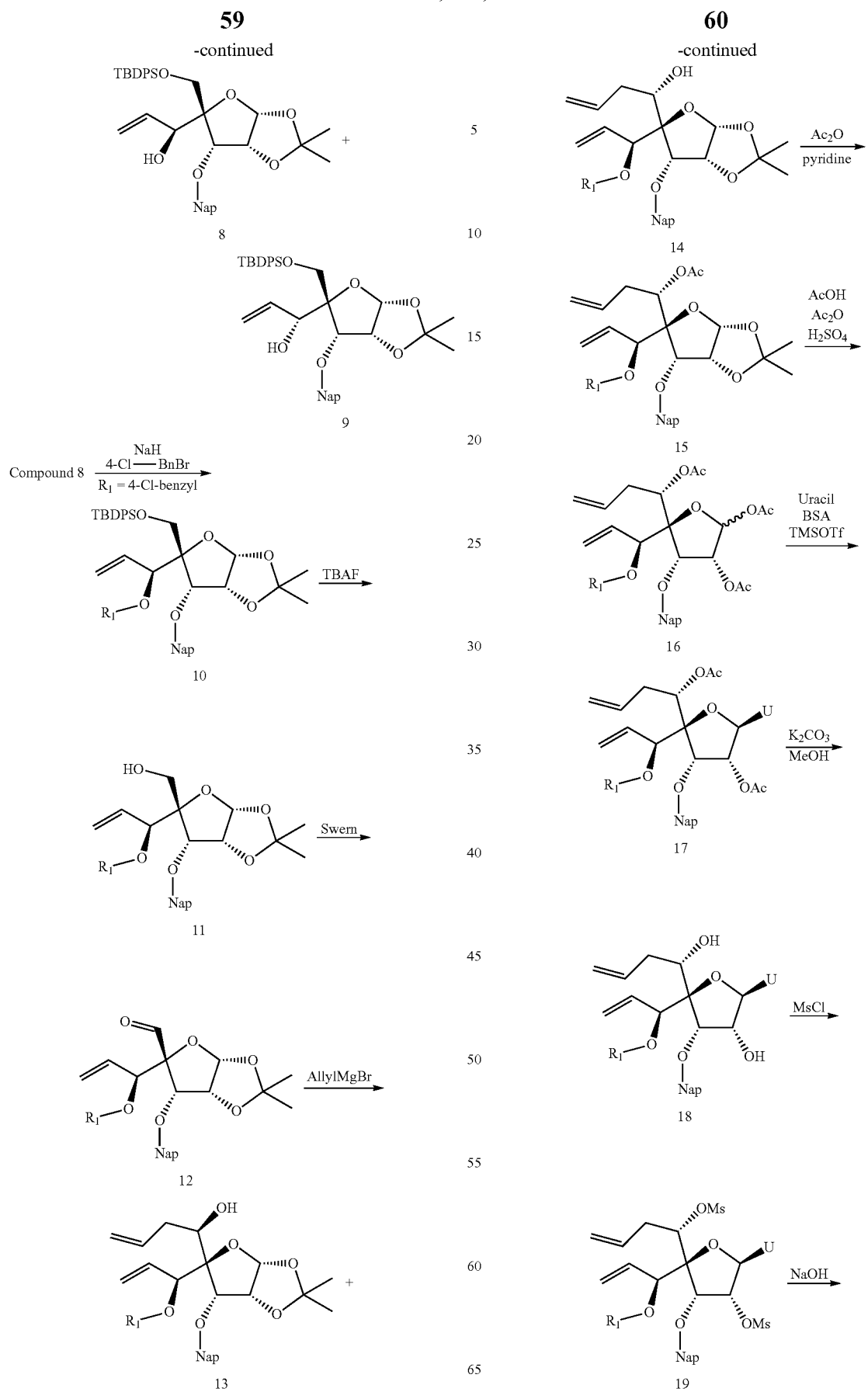

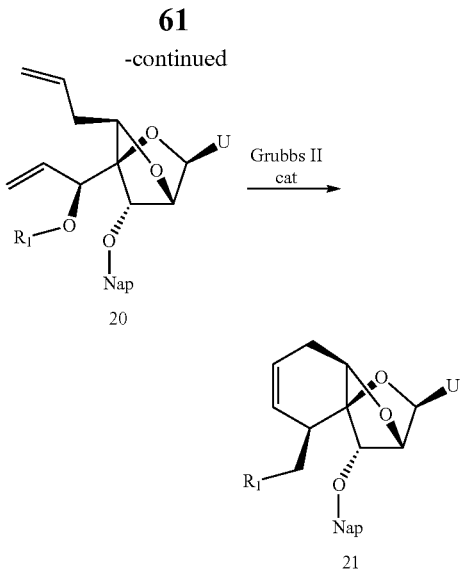

a) Preparation of Compounds 8 and 9

Compound 6 was prepared as per the procedures illustrated in Example 1. Dimethylsulfoxide (35.22 mmol, 2.5 mL) was added dropwise to a cold (−78° C.) solution of oxalyl chloride (17.61 mmol, 1.5 mL) in dichloromethane (100 mL). After stirring for 30 minutes a solution of Compound 6 (12.60 mmol, 7.5 g) in dichloromethane (20 mL) was added dropwise and the stirring was continued for another 45 minutes. Triethylamine (53.00 mmol, 7.4 mL) was added to the reaction and the cooling bath was removed. After stirring for an additional 30 minutes, TLC analysis showed complete consumption of the starting material, Compound 6. The reaction was diluted with chloroform and the organic layer was sequentially washed with 10% HCl, saturated NaHCO$_3$, brine, dried (Na$_2$SO$_4$) and concentrated under reduced pressure to provide the corresponding aldehyde, which was used without any further purification.

Vinyl magnesium bromide (25.20 mmol, 25.2 mL of a 1M solution) was added to a cold (−78° C.) suspension of cerium chloride (2.50 mmol, 0.62 g) in THF (100 mL). After stirring for 1 hour, a solution of aldehyde from above (12.60 mmol) in THF (20 mL) was added to the reaction. After stirring for 2 hours, the reaction was carefully quenched by the addition of saturated NH$_4$Cl solution. The reaction was then diluted with EtOAc and the organic layer was washed with 10% HCl, saturated NaHCO$_3$, brine, dried (Na$_2$SO$_4$) and concentrated under reduced pressure. Purification by column chromatography (SiO$_2$, eluting with 10 to 20% EtOAc in hexanes) provided pure Compound 8 (5.13 g), pure Compound 9 (1.2 g) and a mixture of 8 and 9 (1.13 g). Structural analysis of the desired products was confirmed by $^1$H NMR and LCMS.

b) Preparation of Compound 11

Sodium hydride (60% w/w, 3.86 mmol, 0.15 g) was added to a cold (0° C.) solution of Compound 8 (1.93 mmol, 1.2 g) and 4-chloro benzylbromide (5.77 mmol, 1.18 g) in DMF (4 mL). After stirring for 2 hours, the reaction was quenched with water and diluted with EtOAc. The organic layer was washed with water, brine, dried (Na$_2$SO$_4$) and concentrated to provide Compound 10, which was used without any further purification.

Tetrabutylammonium fluoride (3 mmol, 3 mL of a 1M solution) was added to a solution of Compound 10 from above in THF (2 mL). After stirring for 16 hours at room temperature, additional TBAF (5 mL) was added and the stirring was continued for another 4 hours. The reaction was then diluted with EtOAc and the organic layer was washed with water, brine, dried (Na$_2$SO$_4$) and concentrated. Purification by column chromatography (SiO$_2$, eluting with 25% EtOAc in hexanes) provided Compound 11 (0.70 g, 71% from 2). Structural analysis for the desired product was confirmed by $^1$H NMR and LCMS.

c) Preparation of Compounds 13 and 14

Dimethylsulfoxide (4.10 mmol, 0.29 mL) was added dropwise to a cold (−78° C.) solution of oxalyl chloride (2.05 mmol, 0.18 mL) in dichloromethane (10 mL). After stirring for 30 minutes a solution of Compound 11 (1.37 mmol, 0.7 g) in dichloromethane (3 mL) was added dropwise and the stirring was continued for another 45 minutes. Triethylamine (6.2 mmol, 0.87 mL) was added to the reaction and the cooling bath was removed. After stirring for an additional 30 minutes, TLC analysis showed complete consumption of the starting material, Compound 11. The reaction was diluted with chloroform and the organic layer was sequentially washed with 10% HCl, saturated NaHCO$_3$, brine, dried (Na$_2$SO$_4$) and concentrated under reduced pressure to provide the corresponding aldehyde, Compound 12, which was used without any further purification.

Allyl magnesium bromide (2.74 mmol, 2.7 mL of a 1 M solution) was added to a cold (−78° C.) suspension of cerium chloride (0.27 mmol, 0.07 g) in THF (10 mL). After stirring for 1 hour, a solution of aldehyde, Compound 12, from above (1.37 mmol) in THF (2 mL) was added to the reaction. After stirring for 2 hours, the reaction was carefully quenched by the addition of saturated NH$_4$Cl solution. The reaction was then diluted with EtOAc and the organic layer was washed with 10% HCl, saturated NaHCO$_3$, brine, dried (Na$_2$SO$_4$) and concentrated under reduced pressure. Purification by column chromatography (SiO$_2$, eluting with 10 to 20% EtOAc in hexanes) provided Compound 13 (0.30 g) and Compound 14 (0.39 g). Structural analysis of the desired products was confirmed by $^1$H NMR and LCMS.

d) Preparation of Compound 18

Acetic anhydride (1 mL) was added to a solution of alcohol, Compound 14 (0.71 mmol, 0.39 g) in pyridine (4 mL). After stirring at room temperature for 16 hours, the reaction was diluted with EtOAc and the organic layer was washed with 10% HCl, saturated NaHCO$_3$, brine, dried (Na$_2$SO$_4$) and concentrated to provide acetate, Compound 15, which was used without any further purification.

Concentrated H$_2$SO$_4$ (1 drop) was added to a solution of acetate, Compound 15 from above in acetic acid (2 mL) and acetic anhydride (0.5 mL). After stirring for 5 minutes, the reaction was diluted with EtOAc and the organic layer was carefully washed with saturated NaHCO$_3$, brine, dried (Na$_2$SO$_4$) and concentrated to provide Compound 16, which was used without any further purification.

N,O-bis-trimethylsilylamide (3.55 mmol, 0.88 mL) was added to a suspension of uracil (1.42 mmol, 0.16 g) and Compound 16 (0.71 mmol) in acetonitrile (3.5 mL). The suspension was gently warmed until all the uracil dissolved and a clear solution resulted. The reaction was cooled in an ice-bath and TMSOTf (1.42 mmol, 0.26 mL) was added to the reaction. After stirring for 5 minutes, the reaction was transferred to a preheated oil bath. After refluxing for 2 hours, the reaction was cooled to room temperature and diluted with EtOAc. The organic layer was washed with saturated NaHCO$_3$, brine, dried (Na$_2$SO$_4$) and concentrated to provide Compound 17, which was used without any further purification.

Potassium carbonate (1.4 mmol, 0.19 g) was added to a solution of Compound 17 from above in MeOH (4 mL). After stirring at room temperature for 16 hours, the reaction was neutralized with acetic acid and diluted with EtOAc. The organic layer was washed with water, dried (Na$_2$SO$_4$) and concentrated. Purification by column chromatography (SiO$_2$, eluting with 10 to 30% acetone in chloroform) provided Compound 18 (0.34 g, 80% from 14). Structural analysis of the desired product was confirmed by $^1$H NMR and LCMS.

e) Preparation of Compound 20

Methanesulfonyl chloride (2.25 mmol, 0.18 mL) was added to a solution of Compound 18 (0.56 mmol, 0.34 g) in pyridine (2.8 mL). After stirring at room temperature for 16 hours, the reaction was diluted with EtOAc and the organic layer was washed with HCl, saturated NaHCO$_3$, brine, dried (Na$_2$SO$_4$) and concentrated to provide Compound 19, which was used without any further purification.

A solution of NaOH (4M, 0.4 mmol, 0.8 mL) was added to a solution of Compound 19 from above in dioxane (2.7 mL). After stirring at room temperature for 20 hours, the reaction was acidified with HCl and diluted with EtOAc. The organic layer was washed with water, saturated NaHCO$_3$, brine, dried (Na$_2$SO$_4$) and concentrated. Purification by column chromatography provided Compound 20 (0.195 g). Structural analysis of the desired product was confirmed by $^1$H NMR and LCMS.

f) Preparation of Compound 21

Grubbs II catalyst (0.028 mmol, 23 mg) was added to a solution of Compound 20 (0.28 mmol, 0.165 g) in dichloromethane (8.4 mL). After stirring at room temperature for 16 hours, the solvent was removed under reduced pressure. Purification by column chromatography provided Compound 21 (0.145 g). Structural analysis of the desired product was confirmed by $^1$H NMR and LCMS.

Example 15

Preparation of Compound 38

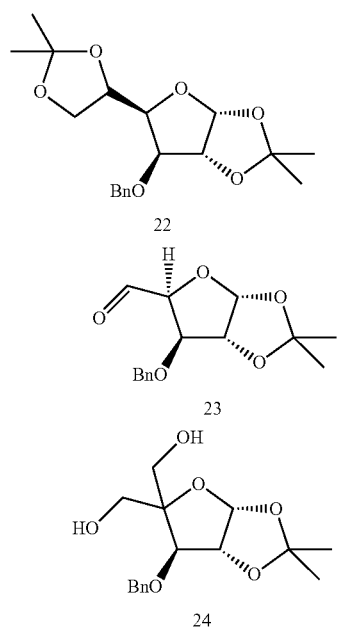

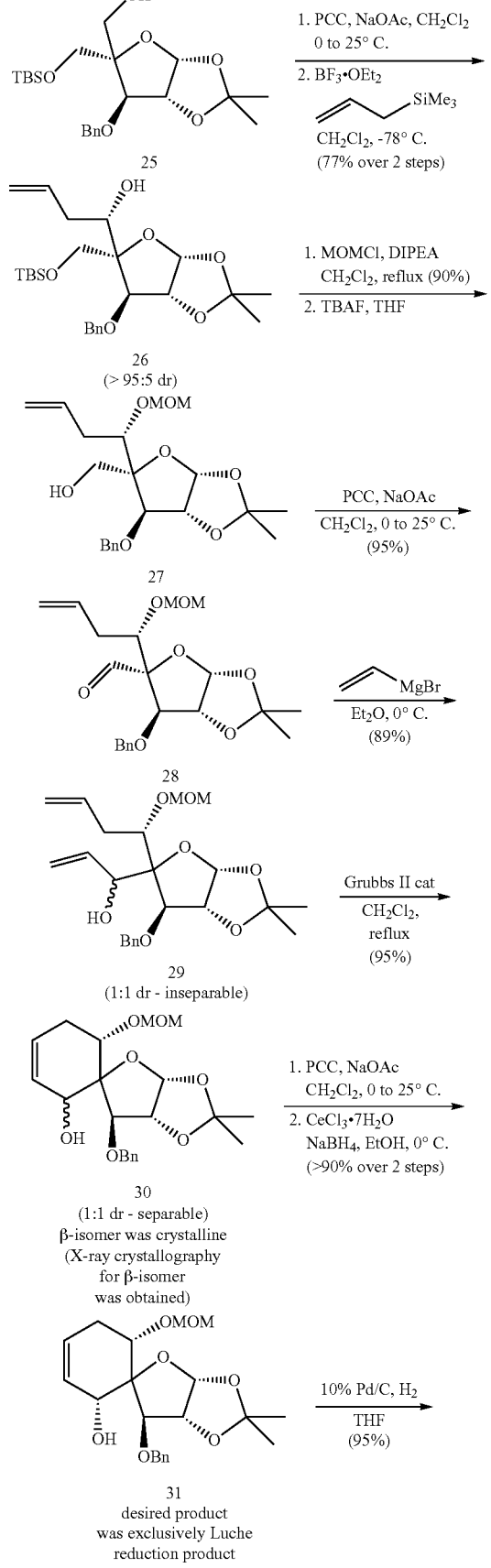

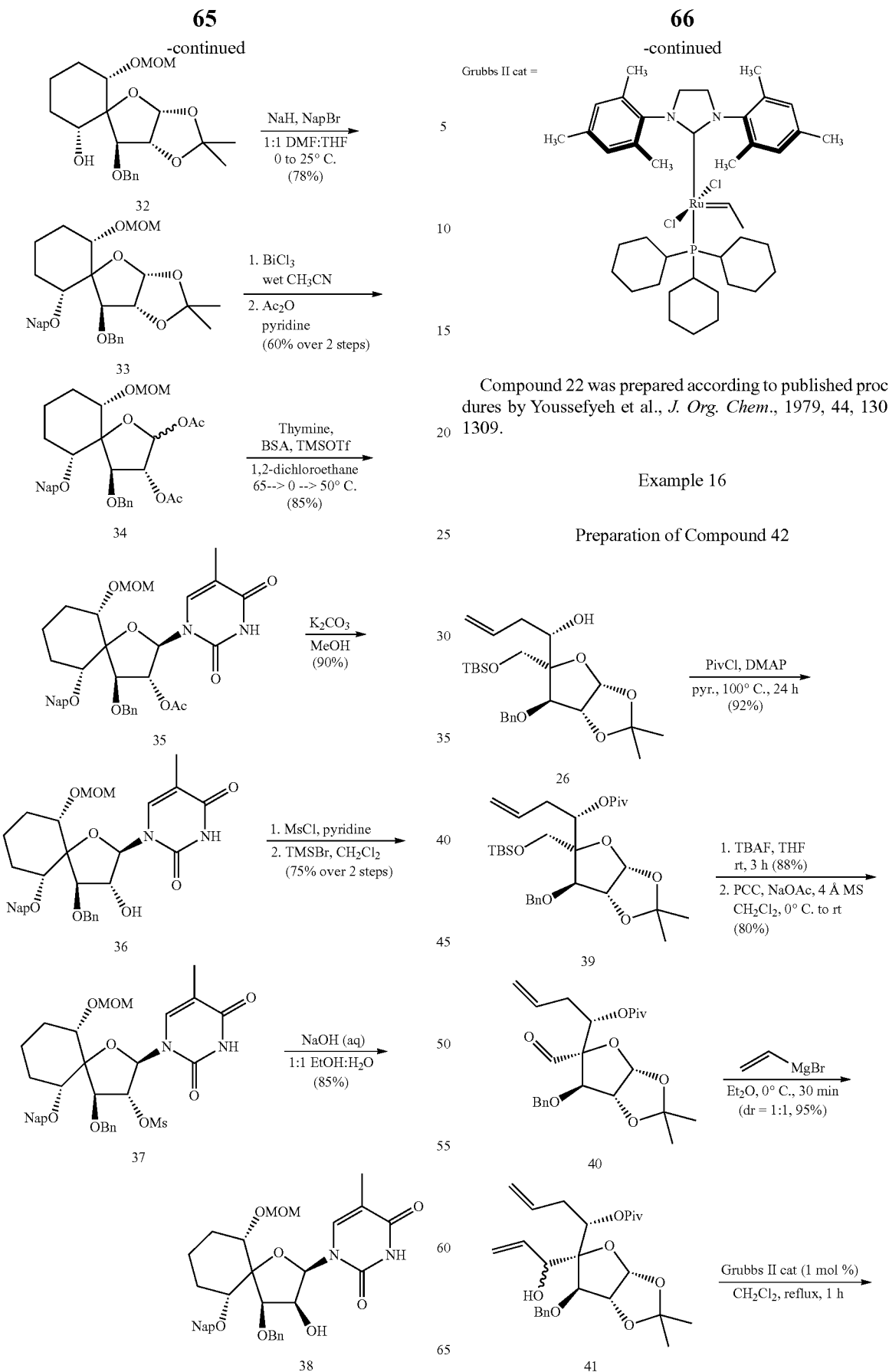
Compound 22 was prepared according to published procedures by Youssefyeh et al., *J. Org. Chem.*, 1979, 44, 1301-1309.
Example 16
Preparation of Compound 42

-continued

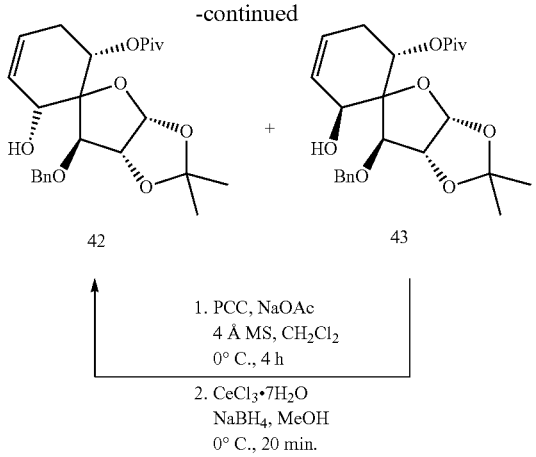

1. PCC, NaOAc
4 Å MS, CH$_2$Cl$_2$
0° C., 4 h

2. CeCl$_3$·7H$_2$O
NaBH$_4$, MeOH
0° C., 20 min.

a) Preparation of Compound 39

Compound 26 was prepared as per the procedure illustrated in Example 15. To a solution of Compound 26 (7.86 g, 16.9 mmol) in pyridine (86 mL) under argon was added pivaloyl chloride (11.0 mL, 84.6 mmol) and 4-(dimethylamino)pyridine (1.03 g, 8.5 mmol). The solution was heated to 100° C. and stirred until complete consumption of the starting material was observed by TLC analysis. After 24 h, the solution was cooled to ambient temperature and partitioned between ethyl acetate (300 mL) and water (150 mL). The aqueous portion was separated and back-extracted with ethyl acetate (3×150 mL), and the combined extracts were washed with 0.5 M aqueous HCl (4×150 mL), a saturated aqueous solution of sodium bicarbonate (150 mL), and brine (150 mL), then dried over magnesium sulfate and concentrated under reduced pressure. The residue was purified by flash column chromatography on silica gel with a solvent system of 9:1 hexanes-ethyl acetate to afford Compound 39 (8.56 g, 92%) as a colorless oil.

Compound 39: R$_f$ 0.50 (9:1 hexanes-ethyl acetate). $[\alpha]_D^{20}$+32.9 (c=1.98, chloroform). IR (film) v 2956, 2931, 1733, 1115 cm$^{-1}$. $^1$H NMR (400 MHz, CDCl$_3$): δ 7.24-7.34 (m, 5H), 6.00 (d, 1H, J=4.4 Hz), 5.71-5.81 (m, 1H), 5.34 (dd, 1H, J=4.4, 4.0 Hz), 4.94-5.01 (m, 2H), 4.74 (dd, 1H, J=2.4, 2.0 Hz), 4.63 (AB, 1H, J=11.6 Hz), 4.57 (AB, 1H, J=11.6 Hz), 4.26 (d, 1H, J=2.0 Hz), 3.78 (AB, 1H, J=10.4 Hz), 3.65 (AB, 1H, J=10.0 Hz), 2.36-2.43 (m, 2H), 1.57 (s, 3H), 1.39 (s, 3H), 1.08 (s, 9H), 0.88 (s, 9H), 0.05 (s, 3H), 0.04 (s, 3H). $^{13}$C NMR (100 MHz, CDCl$_3$): δ 176.82, 137.58, 134.80, 128.31 (2C), 127.65, 127.64 (2C), 117.22, 113.83, 104.80, 89.28, 87.50, 86.46, 72.94, 72.10, 65.02, 38.51, 35.06, 28.11, 27.47, 27.41 (3C), 25.98 (3C), 18.39, −5.32, −5.51. HRMS (ESI) calc'd for C$_{30}$H$_{48}$O$_7$SiNa [M+Na]+m/z 571.3062. found 571.3077.

b) Preparation of Compound 40

To a solution of Compound 39 (8.7 g, 15.8 mmol) in tetrahydrofuran (89 mL) was added a 1.0 M solution of tetrabutylammonium fluoride in tetrahydrofuran (31.7 mL, 31.6 mmol). The solution was stirred for 3 h before a saturated aqueous solution of sodium bicarbonate (40 mL) was added in one portion. The solution was diluted with ethyl acetate (200 mL) and washed with a saturated aqueous solution of sodium bicarbonate (100 mL). The aqueous portion was back-extracted with ethyl acetate (3×75 mL), and the combined extracts were washed with brine (200 mL), dried over magnesium sulfate, and concentrated under reduced pressure. The residue was purified by flash column chromatography on silica gel with a solvent system of 9:1 hexanes-ethyl acetate to afford the primary alcohol (6.05 g, 88%) as a colorless oil.

Primary alcohol: R$_f$ 0.63 (2:1 hexanes-ethyl acetate). $[\alpha]_D^{20}$+21.9 (c=1.48, chloroform). IR (film) v 3496, 2977, 1731, 1158 cm$^{-1}$. $^1$H NMR (400 MHz, CDCl$_3$): δ 7.25-7.35 (m, 5H), 5.96 (d, 1H, J=4.8 Hz), 5.66-5.77 (m, 1H), 5.25 (dd, 1H, J=5.6 Hz, 3.6 Hz), 4.96-5.01 (m, 2H), 4.79 (dd, 1H, J=2.8, 2.0 Hz), 4.70 (AB, 1H, J=11.6 Hz), 4.54 (AB, 1H, J=11.6 Hz), 4.25 (d, 1H, J=2.8 Hz), 3.69 (AB, 1H, J=12.0 Hz), 3.56 (AB, 1H, J=12.0 Hz), 2.43-2.49 (m, 1H), 2.27-2.34 (m, 1H), 2.20 (br s, 1H), 1.56 (s, 3H), 1.37 (s, 3H), 1.13 (s, 9H). $^{13}$C NMR (100 MHz, CDCl$_3$): δ 177.06, 137.36, 134.30, 128.40 (2C), 127.83, 127.57 (2C), 117.53, 114.02, 104.74, 89.52, 86.87, 85.00, 72.73, 71.71, 62.59, 38.61, 35.05, 27.92, 27.52, 27.38 (3C). HRMS (ESI) calc'd for C$_{24}$H$_{34}$O$_7$Na [M+Na]+m/z 457.2197. found 457.2198.

To a mixture of pyridinium chlorochromate (7.3 g, 33.4 mmol), sodium acetate (2.8 g, 33.9 mmol), and powdered 4 Å molecular sieves (9.0 g) in dichloromethane (220 mL) at 0° C. was added a solution of primary alcohol from above (4.9 g, 11.1 mmol) in dichloromethane (70 mL). The mixture was allowed to warm to ambient temperature and following complete consumption of the starting material by TLC analysis (~3 h), diethyl ether and silica gel were added to the reaction mixture, which was stirred for an additional 20 min. The mixture was filtered through a short pad of silica gel and eluted with diethyl ether before the filtrate was concentrated under reduced pressure. The residue was purified by flash column chromatography on silica gel with a solvent system of 7:1 hexanes-ethyl acetate to afford Compound 40 (3.90 g, 80%) as a colorless oil.

Compound 40: R$_f$ 0.38 (9:1 hexanes-ethyl acetate). $[\alpha]_D^{20}$−31.1 (c=0.98, chloroform). IR (film) v 2979, 1733, 1160, 1073 cm$^{-1}$. $^1$H NMR (400 MHz, CDCl$_3$): δ 9.67 (d, 1H, J=1.2 Hz), 7.29-7.38 (m, 5H), 6.03 (d, 1H, J=4.0 Hz), 5.51-5.62 (m, 2H), 4.98 (s, 1H), 4.94-4.95 (m, 1H), 4.69 (AB, 1H, J=11.2 Hz), 4.62 (d, 1H, J=4.0 Hz), 4.52 (AB, 1H, J=11.2 Hz), 4.27 (s, 1H), 2.14-2.29 (m, 2H), 1.40 (s, 3H), 1.27 (s, 3H), 1.17 (s, 9H). $^{13}$C NMR (100 MHz, CDCl3): δ 202.23, 177.20, 136.61, 133.14, 128.69 (2C), 128.31, 127.86 (2C), 118.11, 112.02, 105.53, 93.97, 84.03, 82.76, 73.44, 72.40, 39.04, 34.48, 27.27 (3C), 25.88, 25.70. HRMS (ESI) calc'd for C$_{24}$H$_{32}$O$_7$Na [M+Na]+m/z 455.2040. found 455.2039.

c) Preparation of Compound 41

To a solution of Compound 40 (2.58 g, 5.97 mmol) in anhydrous diethyl ether (50 mL) at 0° C. was added dropwise a 1 M solution of vinylmagnesium bromide in THF (11.9 mL, 11.9 mmol). The solution was stirred at 0° C. for 30 min. before a saturated aqueous solution of ammonium chloride (5 mL) was added. The mixture was partitioned between ethyl acetate (100 mL) and additional ammonium chloride (100 mL). The aqueous portion was separated and back-extracted with ethyl acetate (3×50 mL), and the combined extracts were washed with a saturated aqueous solution of sodium bicarbonate (100 mL) and brine (100 mL), then dried over magnesium sulfate, filtered, and concentrated under reduced pressure. The residue was purified by flash column chromatography on silica gel with a solvent system of 9:1 hexanes-ethyl acetate to afford Compound 41 (2.61 g, 95%, mixture of diastereomers) as a colorless oil.

Compound 41: Rf 0.50 (4:1 hexanes-ethyl acetate). $[\alpha]_D^{20}$+44.6 (c=1.18, chloroform). IR (film) v 2979, 1732, 1152 cm$^{-1}$. $^1$H NMR (400 MHz, CDCl$_3$): δ 7.23-7.36 (m, 10H), 5.91-6.03 (m, 3H), 5.67-5.80 (m, 3H), 5.40-5.48 (m, 2H), 5.21-5.30 (m, 5H), 4.94-5.04 (m, 4H), 4.76-4.78 (m, 2H), 4.66 (AB, 1H, J=12.0 Hz), 4.59 (AB, 1H, J=12.0 Hz), 4.51 (AB, 1H, J=12.0 Hz), 4.48 (AB, 1H, J=12.0 Hz), 4.30-

4.33 (m, 3H), 4.11 (d, 1H, J=2.4 Hz), 2.64-2.70 (m, 1H), 2.39-2.48 (m, 3H), 1.61 (s, 3H), 1.54 (s, 3H), 1.38 (s, 3H), 1.37 (s, 3H), 1.11 (s, 9H), 1.07 (s, 9H). $^{13}$C NMR (100 MHz, CDCl$_3$): δ 176.80, 176.36, 137.36, 137.23, 135.41, 134.89, 134.16, 133.28, 128.48 (2C), 128.26 (2C), 128.05 (2C), 127.97, 127.65, 127.58 (2C), 118.91, 117.72, 117.15, 116.94, 114.47, 114.41, 104.82, 104.64, 93.30, 90.38, 87.372, 87.3428, 85.6532, 83.2138, 74.6803, 72.6533, 72.3568, 72.0312, 71.6992, 71.3711, 38.5883, 38.4496, 35.1333, 34.8085, 28.1392, 27.8892, 27.7646, 27.6209, 27.4653 (3C), 27.4397 (3C). FIRMS (ESI) calc'd for C$_{26}$H$_{36}$O$_7$Na [M+Na]+m/z 483.2353. found 483.2351.

d) Preparation of Compound 42

To a solution of Compound 41 (2.60 g, 5.65 mmol) in anhydrous dichloromethane was added Grubbs' II catalyst (0.048 g, 0.056 mmol). The solution was heated to reflux and stirred for 1 h under argon before it was cooled to ambient temperature and concentrated under reduced pressure. The residue was purified by flash column chromatography on silica gel with a solvent system of 5:1 hexanes-ethyl acetate to afford Compound 42 (1.12 g, 46%) and Compound 43 (1.16 g, 47%) as a separable mixture of colorless oils.

Compound 42: R$_f$ 0.37 (4:1 hexanes-ethyl acetate). [α]$_D^{20}$+12.5 (c=1.23, chloroform). IR (film) v 3500, 2977, 1732, 1150 cm$^{-1}$. $^1$H NMR (400 MHz, CDCl$_3$): δ 7.26-7.32 (m, 5H), 6.07 (d, 1H, J=4.8 Hz), 5.57-5.66 (m, 2H), 5.12 (dd, 1H, J=6.0, 4.0 Hz), 4.89 (dd, 1H, J=4.8, 0.8 Hz), 4.75 (AB, 1H, J=12.0 Hz), 4.58 (AB, 1H, J=12.0 Hz), 4.41 (d, 1H, J=3.6 Hz), 4.16 (d, 1H, J=6.8 Hz), 2.55 (d, 1H, J=10.8 Hz), 2.38-2.45 (m, 1H), 2.18-2.25 (m, 1H), 1.62 (s, 3H), 1.42 (s, 3H), 1.16 (s, 9H). $^{13}$C NMR (100 MHz, CDCl$_3$): δ 176.46, 137.41, 128.78, 128.19 (2C), 127.52, 127.05 (2C), 125.36, 114.69, 105.04, 86.80, 86.74, 84.71, 72.36, 70.48, 68.52, 38.24, 28.24, 28.06, 27.39, 27.15 (3C). HRMS (ESI) calc'd for C$_{24}$H$_{32}$O$_7$Na [M+Na]+m/z 455.2040. found 455.2050.

Compound 43: R$_f$ 0.29 (4:1 hexanes-ethyl acetate). [α]$_D^{20}$+81.4 (c=0.83, chloroform). IR (film) v 3500, 2975, 1732, 1151 cm$^{-1}$. $^1$H NMR (400 MHz, CDCl$_3$): δ 7.17-7.29 (m, 5H), 6.02 (d, 1H, J=4.4 Hz), 5.70-5.78 (m, 2H), 5.38 (dd, 1H, J=6.0, 2.8 Hz), 4.76 (dd, 1H, J=2.0, 2.0 Hz), 4.64 (s, 2H), 4.33 (d, 1H, J=2.0 Hz), 4.07 (br s, 1H), 3.02 (br s, 1H), 2.44-2.50 (m, 1H), 2.19-2.25 (m, 1H), 1.54 (s, 3H), 1.40 (s, 3H), 1.09 (s, 9H). $^{13}$C NMR (100 MHz, CDCl$_3$): δ 177.25, 137.61, 128.02 (2C), 127.78, 127.31, 127.23 (2C), 126.27, 113.96, 104.69, 87.72, 87.60, 86.72, 72.62, 72.47, 68.97, 38.24, 28.56, 27.95, 27.62, 27.06 (3C). HRMS (ESI) calc'd for C$_{24}$H$_{32}$O$_7$Na [M+Na]+m/z 455.2040. found 455.2048.

e) Recover Compound 42 from Compound 43

To a mixture of pyridinium chlorochromate (1.55 g, 7.2 mmol), sodium acetate (0.60 g, 7.3 mmol), and powdered 4 Å molecular sieves (1.9 g) in dichloromethane (63 mL) at 0° C. was added a solution of Compound 43 (1.15 g, 2.6 mmol) in dichloromethane (30 mL). After 4 h when complete consumption of the starting was observed by TLC analysis, diethyl ether and silica gel were added to the reaction mixture, which was stirred for an additional 30 min. The mixture was filtered through a short pad of silica gel and eluted with diethyl ether before the filtrate was concentrated under reduced pressure to afford a residue (1.15 g) that was used without further purification in the next step. A portion of the residue was purified by flash column chromatography on silica gel with a solvent system of 5:1 hexanes-ethyl acetate to afford the enone product as a colorless oil.

Enone product: R$_f$ 0.53 (4:1 hexanes-ethyl acetate). [α]$_D^{20}$+71.6 (c=0.85, chloroform). IR v 2975, 1738, 1694, 1277, 1143 cm$^{-1}$. $^1$H NMR (400 MHz, CDCl$_3$): δ 7.22-7.32 (m, 5H), 6.88-6.93 (m, 1H), 6.12-6.15 (m, 1H), 6.08 (d, 1H, J=4.4 Hz), 5.29 (dd, 1H, J=5.6, 3.2 Hz), 4.97 (d, 1H, J=2.4 Hz), 4.87-4.88 (m, 1H), 4.67 (AB, 1H, J=11.6 Hz), 4.55 (AB, 1H, J=11.6 Hz), 2.72-2.79 (m, 1H), 2.60-2.67 (m, 1H), 1.53 (s, 3H), 1.43 (s, 3H), 1.15 (s, 9H). 13C NMR (100 MHz, CDCl$_3$): δ 191.37, 176.53, 147.97, 137.18, 128.18 (3C), 127.58, 127.18 (2C), 114.72, 105.96, 87.59, 87.08, 83.18, 72.71, 70.91, 38.32, 28.57, 27.95, 27.40, 27.12 (3C). HRMS (ESI) calc'd for C$_{24}$H$_{30}$O$_7$Na [M+Na]+m/z 453.1884. found 453.1898.

To a solution of crude enone product from above (1.15 g, 2.4 mmol) in methanol (55 mL) at 0° C., was added cerium (III) chloride heptahydrate (1.8 g, 4.8 mmol). The solution was stirred for 10 min before sodium borohydride (0.18 g, 4.8 mmol) was added in one portion. After 10 min when complete consumption of the starting material was observed by TLC analysis, acetone (3 mL) was added and the solution was concentrated under reduced pressure. The residue was reconstituted in ethyl acetate (100 mL), washed sequentially with water (50 mL), 0.5 M aqueous HCl (50 mL), and brine (50 mL), then dried over magnesium sulfate, filtered, and concentrated under reduced pressure. The residue was purified by flash column chromatography on silica gel with a solvent system of 5:1 hexanes-ethyl acetate to afford Compound 42 (0.982 g, 85% over two steps) as a colorless oil.

Example 17

Alternative Method for the Preparation of Compound 38

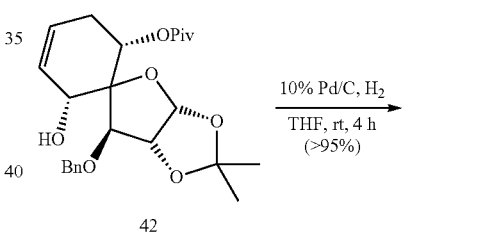

42

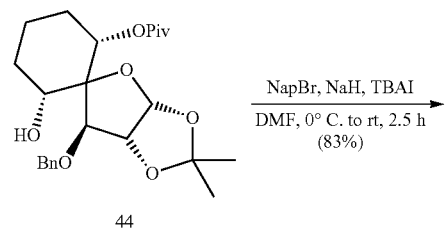

44

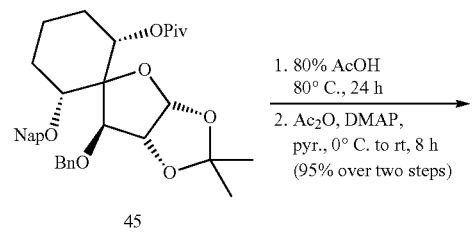

45

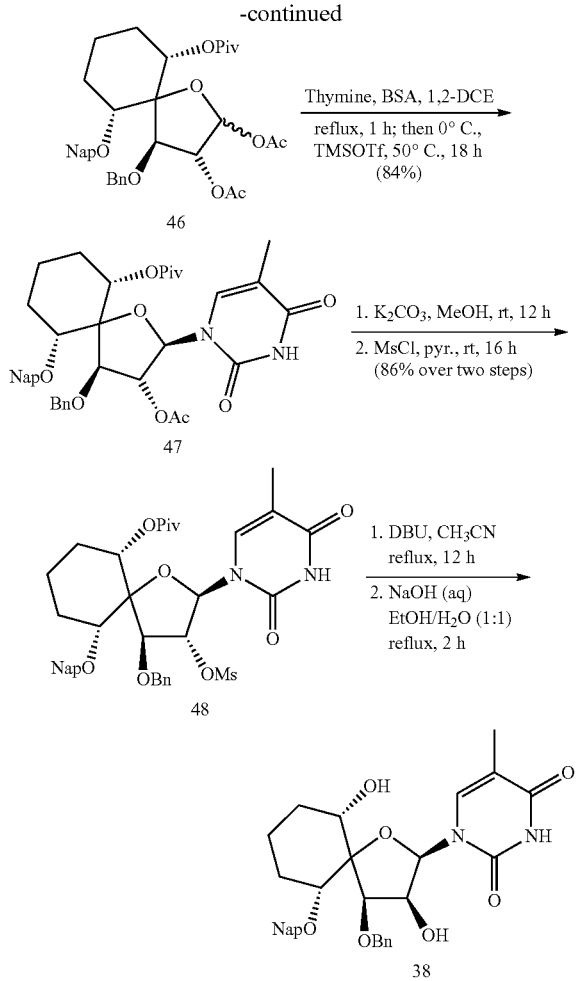

a) Preparation of Compound 44

Compound 42 was prepared as per the procedure illustrated in Example 16. To a solution of Compound 42 (1.97 g, 4.55 mmol) in tetrahydrofuran (50 mL) was added 10% (w/w) palladium on carbon (0.10 g). The suspension was purged with $H_2$ and maintained under an atmosphere of $H_2$ for 4 h. The reaction mixture was diluted with ethyl acetate, filtered through a pad of Celite® 545, and concentrated under reduced pressure. The residue was purified by flash column chromatography on silica gel with a solvent system of 4:1 hexanes-ethyl acetate to afford Compound 44 (1.90 g, 96%) as a colorless foam.

Compound 44: $R_f$ 0.33 (4:1 hexanes-ethyl acetate). $[\alpha]_D^{20}$+18.6 (c=0.29, chloroform). IR (film) v 3512, 2941, 1731, 1159, 1089, 1035 cm$^{-1}$. $^1$H NMR (400 MHz, CDCl$_3$): δ 7.23-7.34 (m, 5H), 6.02 (d, 1H, J=4.8 Hz), 4.79-4.85 (m, 2H), 4.72 (AB, 1H, J=12.0 Hz), 4.56 (AB, 1H, J=12.0 Hz), 4.48 (d, 1H, J=3.6 Hz), 3.37 (dd, 1H, J=6.8, 4.8 Hz), 2.16 (br s, 1H), 1.85-1.89 (m, 1H), 1.74-1.78 (m, 1H), 1.67-1.68 (m, 1H), 1.59 (s, 3H), 1.40-1.55 (m, 2H), 1.39 (s, 3H), 1.21-1.32 (m, 1H), 1.14 (s, 9H). $^{13}$C NMR (100 MHz, CDCl$_3$): δ 176.67, 137.69, 128.27 (2C), 127.55, 127.15 (2C), 114.12, 104.54, 90.20, 87.13, 83.85, 72.86, 72.39, 70.04, 38.38, 30.99, 28.22, 27.93, 27.26 (3C), 25.59, 19.62. FIRMS (ESI) calc'd for C$_{24}$H$_{34}$O$_7$Na [M+Na]+m/z 457.2197. found 457.2210.

b) Preparation of Compound 45

To a solution of Compound 44 (1.79 g, 4.12 mmol) in tetrahydrofuran (25 mL) and N,N-dimethylformamide (25 mL) at 0° C. was sequentially added a 60% (w/w) dispersion of sodium hydride in mineral oil (0.148 g, 6.18 mmol), 2-(bromomethyl)naphthalene (1.37 g, 6.18 mmol) and tetrabutylammonium iodide (0.761 g, 2.06 mmol). The mixture was warmed to ambient temperature and stirred until complete consumption of the starting material as indicated by TLC analysis (~2.5 h). The mixture was cooled to 0° C., methanol (5 mL) was added in one portion, and the mixture was partitioned between dichloromethane (200 mL) and water (100 mL). The aqueous portion was separated and back-extracted with dichloromethane (3×50 mL), and the combined extracts were washed with a saturated aqueous solution of sodium bicarbonate (4×100 mL) and brine (100 mL), then dried over magnesium sulfate, filtered, and concentrated under reduced pressure. The residue was purified by flash column chromatography on silica gel with a solvent system of 9:1 hexanes-ethyl acetate to afford Compound 45 (1.96 g, 83%) as a colorless oil.

Compound 45: $R_f$ 0.61 (4:1 hexanes-ethyl acetate). $[\alpha]_D^{20}$-24.6 (c=1.80, chloroform). IR (film) v 2968, 1729, 1148, 1027 cm$^{-1}$. $^1$H NMR (300 MHz, CDCl$_3$): δ 7.76-7.83 (m, 3H), 7.64 (s, 1H), 7.44-7.50 (m, 2H), 7.22-7.33 (m, 4H), 7.14-7.21 (m, 2H), 6.08 (d, 1H, J=4.8 Hz), 4.76-4.83 (m, 2H), 4.64 (AB, 1H, J=11.7 Hz), 4.61 (AB, 1H, J=12.0 Hz), 4.43 (d, 1H, J=3.0 Hz), 4.24 (AB, 1H, J=11.7 Hz), 4.22 (AB, 1H, J=12.0 Hz), 3.22 (dd, 1H, J=7.2, 4.5 Hz), 1.93-2.01 (m, 1H), 1.65-1.74 (m, 5H), 1.51 (s, 3H), 1.40 (s, 3H), 1.17 (s, 9H). $^{13}$C NMR (75 MHz, CDCl$_3$): δ 176.91, 137.77, 135.43, 133.20, 133.01, 128.33 (2C), 128.01, 127.96, 127.77, 127.67, 127.63 (2C), 127.16, 126.62, 126.20, 126.02, 114.78, 104.81, 88.27, 88.07, 82.73, 76.66, 73.78, 71.93, 71.87, 38.47, 28.42, 28.00, 27.38 (3C), 26.19, 25.84, 19.90. HRMS (ESI) calc'd for C$_{35}$H$_{42}$O$_7$Na [M+Na]+m/z 597.2823. found 597.2834.

c) Preparation of Compound 46

A solution of Compound 45 (1.96 g, 3.42 mmol) in aqueous 80% (v/v) acetic acid (20 mL) was heated to 80° C. and stirred until complete consumption of the starting material as indicated by TLC analysis. After approximately 24 h, the solution was cooled to ambient temperature and concentrated under reduced pressure. The residue was reconstituted in toluene and concentrated under reduced pressure (5×50 mL) to remove the residual acetic acid. The resultant oil was placed under high vacuum for 3 h, reconstituted in pyridine (20 mL), and cooled to 0° C. Acetic anhydride (3.35 mL, 35.1 mmol) and 4-(dimethylamino)pyridine (0.043 g, 0.352 mmol) were added to the solution before it was warmed to ambient temperature and stirred until complete consumption of the starting material as indicated by TLC analysis. After approximately 8 h, the solution was partitioned between ethyl acetate (100 mL) and water (100 mL). The aqueous portion was separated and back-extracted with ethyl acetate (2×50 mL), and the combined extracts were washed with 0.5 M aqueous HCl (5×100 mL), saturated aqueous solution of sodium bicarbonate (100 mL) and brine (100 mL), then dried over magnesium sulfate, filtered, and concentrated under reduced pressure. The residue was purified by flash column chromatography on silica gel with a solvent system of 4:1 hexanes-ethyl acetate to afford Compound 46 (2.01 g, 95% over two steps) as an amorphous solid.

Compound 46: $R_f$ 0.71 (7:3 hexane-ethyl acetate). $[\alpha]_D^{20}$+ 12.6 (c=1.36, chloroform). IR (film) v 2956, 1752, 1728, 1220 cm$^{-1}$. $^1$H NMR (400 MHz, CDCl$_3$): δ 7.75-7.88 (m, 4H), 7.51-7.53 (m, 2H), 7.42 (d, 1H, J=8.0 Hz), 7.17-7.29 (m, 5H), 6.37 (d, 1H, J=5.2 Hz), 5.57 (dd, 1H, J=5.2, 3.2 Hz), 5.05

(dd, 1H, J=7.6, 4.4 Hz), 4.81-4.85 (m, 2H), 4.72 (AB, 1H, J=11.6 Hz), 4.53 (AB, 1H, J=12.4 Hz), 4.38 (AB, 1H, J=12.4 Hz), 4.26 (AB, 1H, J=12.0 Hz), 2.12 (s, 3H), 1.95-2.01 (m, 1H), 1.57-1.82 (m, 8H), 1.26 (s, 9H). $^{13}$C NMR (100 MHz, CDCl$_3$, major diastereomer): δ177.16, 170.27, 170.16, 138.04, 136.11, 133.32, 133.00, 128.45 (2C), 128.05, 127.90, 127.87, 127.85, 127.80 (2C), 126.35, 126.32, 126.05, 125.95, 91.79, 85.45, 77.74, 77.04, 73.17, 72.27, 71.42, 38.79, 27.34 (3C), 27.30, 25.83, 25.63, 21.16, 20.81, 19.66. FIRMS (ESI) calc'd for C$_{36}$H$_{42}$O$_9$Na [M+Na]+m/z 641.2721. found 641.2732.

d) Preparation of Compound 47

To a mixture of thymine (0.795 g, 6.30 mmol) in anhydrous 1,2-dichloroethane (30 mL) was added N,O-bis(trimethylsilyl)acetamide (4.52 mL, 31.5 mmol). The mixture was heated to 80° C. for 1 h and then cooled to 0° C. To the solution was added Compound 46 (1.95 g, 3.15 mmol) as a solution in anhydrous 1,2-dichloroethane (10 mL) and trimethylsilyl trifluoromethylsulfonate (1.14 mL, 6.30 mmol). The solution was heated to 50° C. for 18 h, then cooled to 0° C. before a saturated aqueous solution of sodium bicarbonate (2 mL) was added in one portion. The mixture was partitioned between ethyl acetate (100 mL) and a saturated aqueous solution of sodium bicarbonate (50 mL). The aqueous portion was separated and back-extracted with ethyl acetate (3×50 mL), and the combined extracts were washed with brine (100 mL), then dried over magnesium sulfate, filtered, and concentrated under reduced pressure. The residue was purified by flash column chromatography on silica gel with a solvent system of 2:1 hexanes-ethyl acetate to afford Compound 47 (2.02 g, 84%) as a colorless foam.

Compound 47: R$_f$ 0.50 (1:1 hexane-ethyl acetate). $[\alpha]_D^{20}$+ 9.19 (c=2.22, chloroform). IR (film) v 3187, 2957, 1748, 1694, 1226, 1141 cm$^{-1}$. $^1$H NMR (400 MHz, CDCl$_3$): δ 8.83 (br s, 1H), 7.83-7.88 (m, 3H), 7.76 (s, 1H), 7.68 (d, 1H, J=1.2 Hz), 7.43-7.53 (m, 3H), 7.24-7.26 (m, 3H), 7.02-7.05 (m, 2H), 6.19 (d, 1H, J=8.0 Hz), 5.48 (t, 1H, J=8.4 Hz), 4.83 (dd, 1H, J=7.6, 4.4 Hz), 4.82 (AB, 1H, J=12.4 Hz), 4.69 (d, 1H, J=8.4 Hz), 4.37 (AB, 1H, J=12.4 Hz), 4.27 (AB, 1H, J=12.0 Hz), 4.14 (AB, 1H, J=12.0 Hz), 3.05 (dd, 1H, J=6.8, 4.4 Hz), 2.04 (s, 3H), 1.95-1.99 (m, 4H), 1.72-1.81 (m, 2H), 1.56-1.65 (m, 2H), 1.24 (m, 10H). $^{13}$C NMR (100 MHz, CDCl$_3$): δ 176.99, 170.68, 163.69, 150.77, 137.48, 135.39, 134.83, 133.35, 133.09, 128.42 (3C), 128.07, 128.03, 127.94 (2C), 127.83, 126.70, 126.47, 126.21, 125.92, 111.30, 85.12, 83.15, 79.48, 78.80, 78.72, 73.68, 72.41, 71.18, 38.66, 27.50 (3C), 26.29, 25.54, 20.85, 19.55, 12.64. HRMS (ESI) calc'd for C$_{39}$H$_{45}$O$_9$N$_2$ [M+H]+m/z 685.3120. found 685.3127.

e) Preparation of Compound 48

To a solution of Compound 47 (2.48 g, 3.6 mmol) in methanol (25 mL) was added potassium carbonate (0.050 g, 0.36 mmol). The solution was stirred at ambient temperature for 12 h before being concentrated under reduced pressure. The residue was reconstituted in ethyl acetate (100 mL) and partitioned with water (75 mL). The aqueous portion was separated and back-extracted with ethyl acetate (3×75 mL), and the combined extracts were washed with brine (100 mL), then dried over magnesium sulfate, filtered, and concentrated under reduced pressure to afford a residue (2.20 g) that was used without further purification in the next step. A portion of the residue was purified by flash column chromatography on silica gel with a solvent system of 3:2 hexanes-ethyl acetate to afford the product as a colorless foam.

Crude alcohol: R$_f$ 0.50 (1:1 hexane-ethyl acetate). $[\alpha]_D^{20}$- 11.3 (c=1.26, chloroform). IR (film) v 3419, 2956, 1694, 1144, 753 cm$^{-1}$. $^1$H NMR (400 MHz, CDCl$_3$): δ 9.33 (br s, 1H), 7.79-7.84 (m, 3H), 7.72 (s, 1H), 7.61 (d, 1H, J=0.8 Hz), 7.41-7.49 (m, 3H), 7.23-7.27 (m, 3H), 7.16-7.18 (m, 2H), 5.93 (d, 1H, J=7.2 Hz), 4.83 (dd, 1H, J=7.2, 4.8 Hz), 4.56-4.68 (m, 3H), 4.28-4.37 (m, 3H), 4.16 (br s, 1H), 3.07 (dd, 1H, J=6.8, 4.4 Hz), 1.97-2.01 (m, 1H), 1.81-1.89 (m, 4H), 1.75-1.80 (m, 1H), 1.50-1.66 (m, 2H), 1.24-1.28 (m, 1H), 1.12 (s, 9H). $^{13}$C NMR (100 MHz, CDCl$_3$): δ 176.82, 163.89, 151.69, 138.06, 135.43, 135.35, 133.31, 133.07, 128.38 (2C), 128.36, 128.13 (2C), 128.09, 127.78 (2C), 126.63, 126.33, 126.12, 125.97, 110.64, 88.70, 86.96, 82.37, 81.75, 78.55, 72.74, 72.23, 71.60, 38.57, 27.37 (3C), 26.71, 25.90, 19.61, 12.66. HRMS (ESI) calc'd for C$_{37}$H$_{43}$O$_8$N$_2$[M+H]+m/z 643.3014. found 643.3020.

To a solution of crude alcohol from above (2.20 g, 3.2 mmol) in pyridine (61 mL) was added methanesulfonyl chloride (1.4 mL, 14.0 mmol). The solution was allowed to stir at ambient temperature for 16 h and partitioned between dichloromethane (150 mL) and water (100 mL). The aqueous portion was separated and back-extracted with dichloromethane (3×75 mL), and the combined extracts were washed sequentially with 0.5 M aqueous HCl (3×150 mL), a saturated aqueous solution of sodium bicarbonate (150 mL), and brine (150 mL), then dried over magnesium sulfate, filtered, and concentrated under reduced pressure. The residue was purified by flash column chromatography on silica gel with a solvent system of 1:2 hexanes-ethyl acetate to afford Compound 48 (2.25 g, 86% over two steps) as a colorless foam.

Compound 48: R$_f$ 0.58 (1:1 hexanes-ethyl acetate). $[\alpha]_D^{20}$+17.7 (c=0.82, chloroform). IR (film) v 2936, 1694, 1180, 1140 cm$^{-1}$. $^1$H NMR (400 MHz, CDCl$_3$): δ 8.67 (br s, 1H), 7.82-7.88 (m, 3H), 7.73 (s, 1H), 7.59 (d, 1H, J=1.2 Hz), 7.46-7.53 (m, 2H), 7.42 (dd, 1H, J=7.2, 1.2 Hz), 7.26-7.28 (m, 3H), 7.07-7.10 (m, 2H), 6.33 (d, 1H, J=8.0 Hz), 5.19 (t, 1H, J=8.0 Hz), 4.81 (dd, 1H, J=7.6, 4.4 Hz), 4.69-4.73 (m, 2H), 4.42 (AB, 1H, J=11.6 Hz), 4.32 (AB, 1H, J=12.0 Hz), 4.21 (AB, 1H, J=11.6 Hz), 3.00 (dd, 1H, J=6.6, 4.8 Hz), 2.96 (s, 3H), 1.95-1.99 (m, 4H), 1.52-1.81 (m, 5H), 1.23 (s, 9H). $^{13}$C NMR (100 MHz, CDCl$_3$): δ 176.59, 163.79, 151.05, 136.85, 135.04, 134.03, 133.08, 132.86, 128.29, 128.20 (2C), 128.11 (2C), 127.92, 127.86, 127.60, 126.54, 126.27, 126.00, 125.73, 111.83, 84.74, 82.57, 82.02, 78.72, 78.20, 73.43, 72.12, 70.88, 38.46, 38.37, 27.26 (3C), 25.94, 25.17, 19.22, 12.44. HRMS (ESI) calc'd for C$_{38}$H$_{44}$O$_{10}$N$_2$SNa [M+Na]+m/z 743.2609. found 743.2617.

f) Preparation of Compound 38

To a solution containing Compound 48 (2.25 g, 3.12 mmol) in acetonitrile (69 mL) was added 1,8-diazabicyclo[5.4.0] undec-7-ene (4.7 mL, 31.2 mmol). The solution was heated to reflux and stirred for 12 h under argon before being cooled to ambient temperature and partitioned between 0.5 M aqueous HCl (100 mL) and ethyl acetate (150 mL). The aqueous portion was separated and back-extracted with ethyl acetate (3×100 mL). The combined extracts were washed with brine (150 mL), dried over magnesium sulfate, filtered, and concentrated under reduced pressure. The crude anhydronucleoside (2.0 g) was utilized without further purification as a pale brown foam.

Crude anhydronucleoside: R$_f$ 0.0 (1:1 hexanes-ethyl acetate). $[\alpha]_D^{20}$-86.9 (c=1.38, chloroform). IR (film) v 2954, 1720, 1644, 1559, 1481 cm$^{-1}$. $^1$H NMR (400 MHz, CDCl$_3$): δ 7.78-7.81 (m, 3H), 7.62 (s, 1H), 7.42-7.48 (m, 2H), 7.26-7.31 (m, 2H), 7.10-7.20 (m, 5H), 6.10 (d, 1H, J=5.6 Hz), 5.30-5.32 (m, 1H), 4.79 (dd, 1H, J=6.8, 4.4 Hz), 4.71 (AB, 1H, J=11.2 Hz), 4.55 (AB, 1H, J=11.2 Hz), 4.34 (AB, 1H, J=11.6 Hz), 4.13 (AB, 1H, J=11.2 Hz), 4.06 (d, 1H, J=6.0 Hz), 3.02 (dd, 1H, J=7.6, 3.6 Hz), 1.92-1.95 (m, 4H), 1.67-1.69 (m, 2H), 1.38-1.56 (m, 2H), 1.08-1.22 (m, 1H), 0.71 (s, 9H). $^{13}$C NMR (100 MHz, CDCl$_3$): δ176.64, 172.22, 159.72, 136.27, 134.42, 132.99, 132.93, 131.30, 129.01 (2C), 128.58, 128.23 (2C), 128.02, 127.80, 127.64, 127.05, 126.39, 126.27, 125.68, 118.49, 91.73, 90.96, 82.16, 80.82, 80.81, 74.26, 71.11, 69.22, 38.00, 27.70, 26.21 (3C), 24.78, 18.97, 13.73. HRMS (ESI) calc'd for $C_{37}H_{41}O_7N_2$ [M+H]+ m/z 625.2908. found 625.2917.

To a mixture of crude anhydronucleoside from above (2.0 g, 3.1 mmol) in ethanol (40 mL) and water (40 mL) was added sodium hydroxide (1.3 g, 32 mmol). The mixture was heated to reflux and stirred for 2 h. The solution was then cooled to ambient temperature and partitioned between ethyl acetate (300 mL) and water (150 mL). The aqueous portion was separated and back-extracted with ethyl acetate (4×100 mL). The combined extracts were washed with 0.5 M aqueous HCl (100 mL) and brine (100 mL), dried over magnesium sulfate, filtered, and concentrated under reduced pressure to afford a crude residue Compound 38 that was used without further purification in the next step.

For the purpose of spectral analysis, a portion of the residue was purified by flash column chromatography on silica gel with a solvent system of 2:3 hexanes-ethyl acetate to afford the desired product as a colorless foam.

Compound 38: $R_f$ 0.20 (1:1 hexanes-ethyl acetate). $[\alpha]_D^{20}$+10.4 (c=0.74, chloroform). IR (film) v 3270, 2941, 1711, 1697, 1661, 1070 cm$^{-1}$. $^1$H NMR (400 MHz, methanol-$d_4$): δ 7.76-7.85 (m, 4H), 7.65 (s, 1H), 7.40-7.45 (m, 2H), 7.28-7.30 (m, 1H), 7.12-7.22 (m, 5H), 5.99 (d, 1H, J=2.8 Hz), 4.62 (AB, 1H, J=12.0 Hz), 4.57 (d, 1H, J=4.8 Hz), 4.52 (AB, 1H, J=11.6 Hz), 4.28 (dd, 1H, J=2.8, 2.0 Hz), 4.17 (AB, 1H, J=11.6 Hz), 4.03 (AB, 1H, J=12.0 Hz), 3.63 (dd, 1H, J=7.2, 4.4 Hz), 1.97-2.01 (m, 1H), 1.84 (d, 3H, J=1.2 Hz), 1.77-1.81 (m, 1H), 1.46-1.72 (m, 3H), 1.14 (dd, 1H, J=7.2, 4.4 Hz), 1.12-1.22 (m, 1H). $^{13}$C NMR (100 MHz, methanol-$d_4$): δ 166.36, 152.05, 139.85, 138.93, 136.80, 134.62, 134.37, 129.37 (2C), 129.23, 129.08 (2C), 129.02, 128.91, 128.68, 127.75, 127.23, 127.18, 127.06, 109.33, 88.59, 87.24, 79.70, 78.74, 72.89, 72.37, 70.04, 69.18, 30.82, 27.01, 20.68, 12.61. HRMS (ESI) calc'd for $C_{32}H_{35}O_7N_2$ [M+H]+ m/z 559.2439. found 559.2450.

Example 18

Preparation of Compound 55

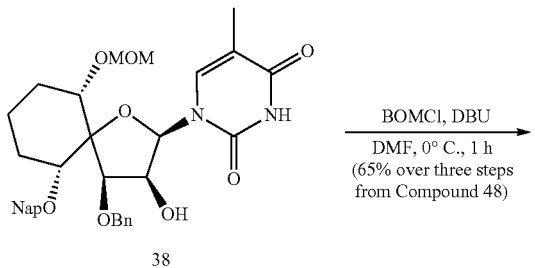

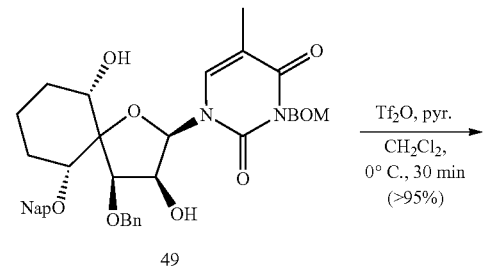

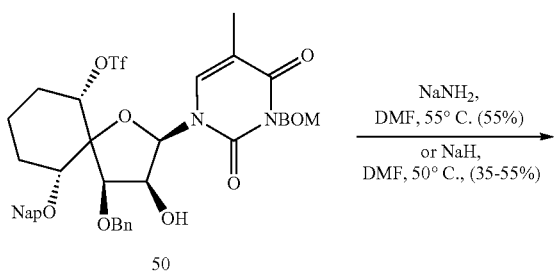

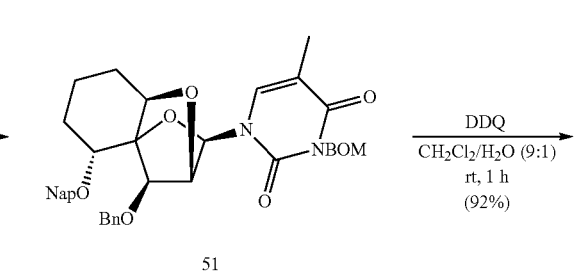

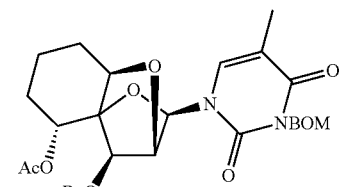

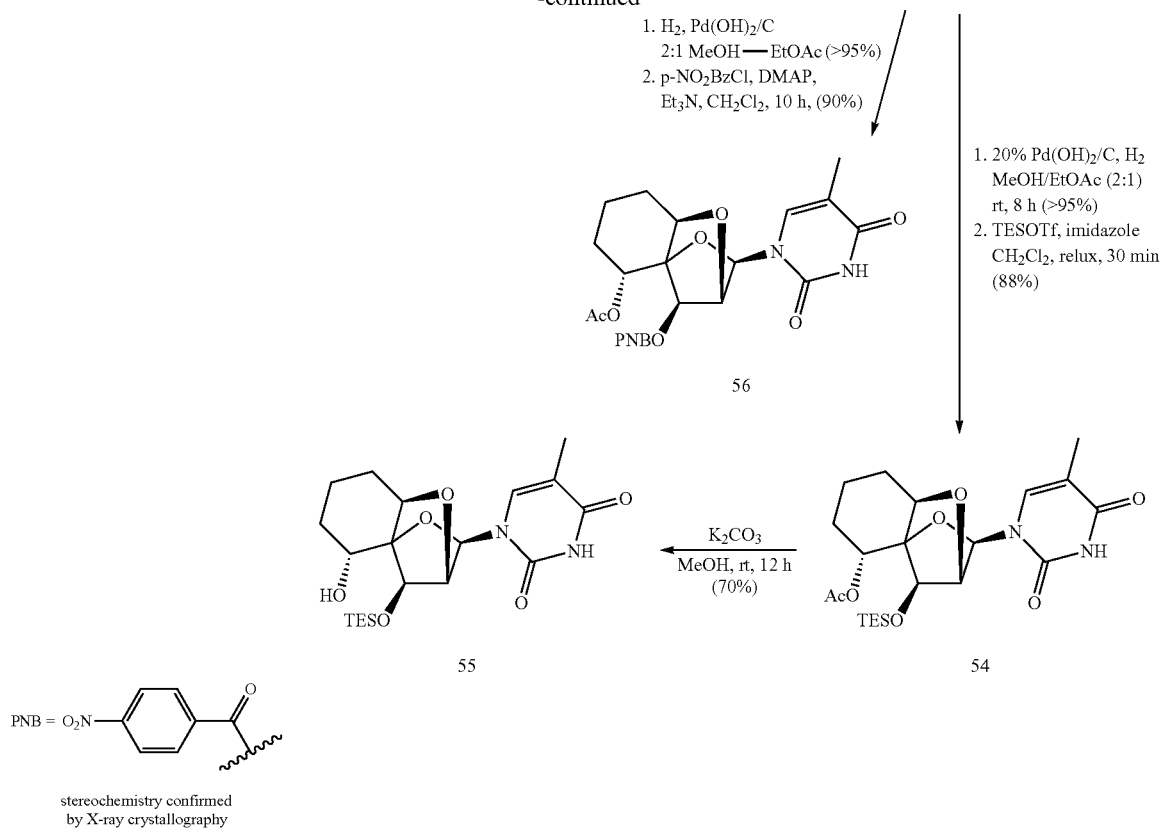

PNB = O₂N—C₆H₄—C(O)— stereochemistry confirmed
by X-ray crystallography a) Preparation of Compound 49

Compound 38 was prepared as per the procedure illustrated in Example 17. To a solution of crude Compound 38 (1.62 g, 2.9 mmol) in N,N-dimethylformamide (53 mL) at 0° C. was added sequentially a 60% (NMR) benzyl chloromethyl ether solution (0.74 mL, 3.2 mmol) and 1,8-diazabicyclo[5.4.0]undec-7-ene (0.52 mL, 3.5 mmol). The solution was stirred for 1 h before it was partitioned between ethyl acetate (200 mL) and water (100 mL). The aqueous portion was separated and back-extracted with ethyl acetate (3×75 mL). The combined extracts were washed with a saturated aqueous solution of sodium bicarbonate (3×100 mL) and brine (100 mL). The organic phase was collected, then dried over magnesium sulfate, filtered, and concentrated under reduced pressure. The residue was purified by flash column chromatography on silica gel with a solvent system of 3:2 hexanes-ethyl acetate to afford Compound 49 (1.32 g, 65% over three steps from Compound 48) as a colorless foam.

Compound 49: $R_f$ 0.55 (1:1 hexanes-ethyl acetate). $[\alpha]_D^{20}$ +14.2 (c=0.24, chloroform). IR (film) v 3322, 1704, 1664, 1067 cm$^{-1}$. $^1$H NMR (400 MHz, CDCl$_3$): δ 7.83-7.87 (m, 3H), 7.67 (s, 1H), 7.73 (s, 1H), 7.48-7.53 (m, 2H), 7.26-7.39 (m, 9H), 7.15-7.17 (m, 2H), 6.11 (d, 1H, J=2.8 Hz), 5.64 (s, 2H), 4.65-4.68 (m, 3H), 4.56-4.60 (m, 2H), 4.36-4.38 (m, 1H), 4.29 (AB, 1H, J=12.0 Hz), 4.11 (AB, 1H, J=11.6 Hz), 3.68 (dd, 1H, J=7.2, 4.4 Hz), 1.96-1.99 (m, 1H), 1.92 (s, 3H), 1.51-1.79 (m, 4H), 1.13 (dd, 1H, J=7.2, 4.4 Hz), 1.10-1.20 (m, 1H). $^{13}$C NMR (100 MHz, CDCl$_3$): δ 163.99, 150.92, 138.02, 137.33, 137.14, 135.28, 133.24, 133.07, 128.57 (2C), 128.44, 128.35 (2C), 128.22, 128.14 (2C), 128.02, 127.86 (2C), 127.79, 127.67, 126.83, 126.38, 126.19, 126.03, 108.02, 87.20, 86.58, 78.64, 78.12, 72.38, 72.13, 71.52, 70.41, 69.74, 68.50, 29.71, 25.87, 19.77, 13.51. HRMS (ESI) calc'd for C$_{40}$H$_{43}$O$_8$N$_2$ [M+H]+m/z 679.3018. found 679.3014.

b) Preparation of Compound 50

To a solution of trifluoromethanesulfonic anhydride (0.57 mL, 3.4 mmol) in anhydrous dichloromethane (16 mL) at 0° C. was added pyridine (0.37 mL, 4.5 mmol) in a dropwise fashion. After stirring 10 min, a solution of Compound 49 (1.54 g, 2.27 mmol) in dichloromethane (16 mL) was added. The reaction mixture solution was allowed to stir at 0° C. for another 30 min before it was partitioned between dichloromethane (75 mL) and water (75 mL). The aqueous portion was separated and back-extracted with dichloromethane (3×50 mL), and the combined extracts were washed sequentially with 0.5 M aqueous HCl (75 mL), a saturated aqueous solution of sodium bicarbonate (75 mL), and brine (75 mL). The organic phase was collected, dried over magnesium sulfate, filtered, and concentrated under reduced pressure to afford Compound 50 that was used as a crude in the next step without further purification.

For the purpose of spectral analysis, a portion the residue was purified by flash column chromatography on silica gel with a solvent system of 3:1 hexanes-ethyl acetate to afford Compound 50 as a colorless foam.

Compound 50: $R_f$ 0.50 (7:3 hexanes-ethyl acetate). $[\alpha]_D^{20}$ +13.8 (c=0.34, chloroform). IR (film) v 2946, 1709, 1666, 1650, 1210 cm$^{-1}$. $^1$H NMR (400 MHz, CDCl$_3$): δ 7.83-7.91 (m, 3H), 7.74 (s, 1H), 7.65 (s, 1H), 7.48-7.57 (m, 2H), 7.15-7.40 (m, 11H), 6.40 (d, 1H, J=3.6 Hz), 5.46-5.54 (m, 3H), 4.78 (AB, 1H, J=12.0 Hz), 4.73 (d, 1H, J=5.6 Hz), 4.69 (s, 2H), 4.59 (AB, 1H, J=12.0 Hz), 4.16 (AB, 1H, J=12.0 Hz), 4.12 (AB, 1H, J=12.0 Hz), 3.58 (dd, 1H, J=7.6, 4.4 Hz), 2.75 (dd, 1H, J=6.8, 4.4 Hz), 2.60 (br s, 1H), 1.98 (s, 3H), 1.47-1.92 (m, 5H), 1.07-1.17 (s, 1H). $^{13}$C NMR (100 MHz, CDCl$_3$): δ 163.44, 150.84, 137.90, 136.03, 135.23, 134.99, 133.27, 133.12, 129.11, 128.99, 128.90 (2C), 128.86 (2C), 128.69, 128.38 (2C), 128.00, 127.88 (2C), 127.87, 127.75, 126.63, 126.61, 126.37, 125.63, 109.87, 88.31, 83.59, 82.88, 79.56, 77.53, 74.90, 72.11, 71.28, 70.46, 70.35, 28.31, 25.66, 19.82, 13.29. HRMS (ESI) calc'd for C$_{41}$H$_{41}$O$_{10}$N$_2$SF$_3$Na [M+Na]+m/z 833.2326. found 833.2347.

c) Preparation of Compound 51

To a mixture of sodium amide (0.17 g, 4.5 mmol) in anhydrous N,N-dimethylformamide (300 mL) at 55° C. was added a solution of Compound 50 (1.54 g, 1.8 mmol) in anhydrous N,N-dimethylformamide (24 mL). The mixture was stirred at 55° C. for 15 min., then quickly cooled to 0° C. before methanol (1 mL) was added in one portion. The solution was partitioned between ethyl acetate (500 mL) and a saturated aqueous solution of sodium bicarbonate (250 mL). The aqueous portion was separated and back-extracted with ethyl acetate (3×200 mL), and the combined extracts were washed with a saturated aqueous solution of sodium bicarbonate (3×200 mL) and brine (200 mL). The organic phase was collected, dried over magnesium sulfate, filtered, and concentrated under reduced pressure. The residue was purified by flash column chromatography on silica gel with a solvent system of 7:3 hexanes-ethyl acetate to afford the desired tricyclic nucleoside Compound 51 (0.62 g, 52% over two steps from Compound 49) as a colorless oil.

Compound 51 was also prepared in a similar manner as described above except NaH was used in place of NaNH$_2$ and the reaction mixture was left heated at 50° C. instead of at 55° C. The resulting residue was purified using the same solvent system as above to provide the desired product in 35-55% yield.

Compound 51: R$_f$ 0.44 (7:3 hexanes-ethyl acetate). [α]$_D^{20}$+17.3 (c=0.22, chloroform). IR (film) v 2926, 1706, 1663, 1068 cm$^{-1}$. $^1$H NMR (400 MHz, CDCl$_3$): δ 7.80-7.85 (m, 4H), 7.56 (d, 1H, J=0.8 Hz), 7.47-7.51 (m, 3H), 7.28-7.39 (m, 10H), 5.75 (d, 1H, J=0.8 Hz), 5.51 (AB, 1H, J=9.6 Hz), 5.46 (AB, 1H, J=9.6 Hz), 4.89 (s, 1H), 4.83-4.85 (m, 2H), 4.74 (AB, 1H, J=12.0 Hz), 4.70 (s, 2H), 4.52 (AB, 1H, J=12.0 Hz), 4.25 (dd, 1H, J=7.6, 3.2 Hz), 4.14 (s, 1H), 4.08 (s, 1H), 1.88-2.01 (m, 3H), 1.86 (s, 3H), 1.74-1.81 (m, 1H), 1.49-1.52 (m, 2H). $^{13}$C NMR (100 MHz, CDCl$_3$): δ 163.70, 151.13, 138.08, 136.98, 136.31, 134.17, 133.36, 133.07, 128.75 (2C), 128.41 (2C), 128.25, 128.18, 127.88 (2C), 127.87 (2C), 127.75, 127.55 (2C), 126.34, 126.09, 126.05, 125.64, 109.19, 89.05, 87.90, 82.36, 81.49, 76.68, 75.12, 72.40, 72.30, 72.27, 70.39, 29.58, 27.94, 17.02, 13.59. HRMS (ESI) calc'd for C$_{40}$H$_{41}$O$_7$N$_2$ [M+H]+m/z 661.2908. found 661.2930.

d) Preparation of Compound 52

To a solution of Compound 51 (0.62 g, 0.94 mmol) in dichloromethane (30.6 mL) and water (3.4 mL) was added 2,3-dichloro-5,6-dicyano-1,4-benzoquinone (0.43 g, 1.9 mmol). After approximately 1 h when the starting material was completely consumed as indicated by TLC analysis, the mixture was concentrated under reduced pressure and reconstituted in ethyl acetate (50 mL). The solution was washed sequentially with a saturated aqueous solution of sodium bicarbonate (50 mL), 10% (w/v) sodium hydrogen sulfite (50 mL), and brine (50 mL). The organic phase was collected, dried over magnesium sulfate, filtered, and concentrated under reduced pressure. The residue was purified by flash column chromatography on silica gel with a solvent system of 1:1 hexanes-ethyl acetate to afford the desired product Compound 52 (0.45 g, 92%) as a colorless foam.

Compound 52: R$_f$ 0.19 (2:1 hexanes-ethyl acetate). [α]$_D^{20}$+2.5 (c=0.12, chloroform). IR (film) v 3444, 2926, 1709, 1666, 1109 cm$^{-1}$. $^1$H NMR (400 MHz, CDCl$_3$): δ 7.49 (d, 1H, J=0.8 Hz), 7.26-7.40 (m, 10H), 5.79 (d, 1H, J=0.8 Hz), 5.49 (AB, 1H, J=9.6 Hz), 5.45 (AB, 1H, J=9.6 Hz), 4.81 (s, 1H), 4.73 (AB, 1H, J=12.0 Hz), 4.69 (s, 2H), 4.53 (AB, 1H, J=12.0 Hz), 4.40 (t, 1H, J=2.4 Hz), 4.21 (dd, 1H, J=7.2, 3.6 Hz), 4.05 (s, 1H), 2.27 (br s, 1H), 2.04-2.07 (m, 1H), 1.98 (d, 3H, J=0.8 Hz), 1.87-1.90 (m, 3H), 1.67-1.77 (m, 1H), 1.49-1.53 (m, 1H). $^{13}$C NMR (100 MHz, CDCl$_3$): δ 163.54, 151.16, 137.98, 136.88, 133.92, 128.77 (2C), 128.41 (2C), 128.25, 127.86 (2C), 127.79, 127.55 (2C), 109.47, 88.70, 87.64, 81.98, 81.36, 72.47, 72.35, 70.47, 67.81, 29.44, 29.41, 16.57, 13.62 (observed 28 of 29 carbon signals); HRMS (ESI) calc'd for C$_{29}$H$_{33}$O$_7$N$_2$ [M+H]+m/z 521.2282. found 521.2297.

e) Preparation of Compound 53

To a solution of Compound 52 (0.451 g, 0.87 mmol) in dichloromethane (14 mL) was sequentially added triethylamine (0.36 mL, 2.6 mmol), acetic anhydride (0.69 mL, 6.9 mmol) and 4-(dimethylamino)pyridine (0.05 g, 0.4 mmol). After stirring for 12 h, the reaction mixture was partitioned between dichloromethane (20 mL) and water (25 mL). The aqueous portion was separated, back-extracted with dichloromethane (2×50 mL), and the combined extracts were sequentially washed with 1 M aqueous HCl (50 mL), sat. sodium bicarbonate (50 mL), and brine (50 mL). The organic phase was collected, dried over magnesium sulfate, filtered, and concentrated under reduced pressure. The residue was purified by flash column chromatography on silica gel with a solvent system of 2:1 hexanes-ethyl acetate to afford Compound 53 (0.47 g, >95%) as a colorless solid.

Compound 53: R$_f$ 0.55 (1:1 hexanes-ethyl acetate). [α]$_D^{20}$+32.9 (c=0.14, chloroform). IR (film) v 2926, 1740, 1707, 1666, 1071 cm$^{-1}$. $^1$H NMR (400 MHz, CDCl$_3$): δ 7.27-7.42 (m, 11H), 5.68 (d, 1H, J=0.8 Hz) 5.65 (s, 1H), 5.49 (AB, 1H, J=10.0 Hz), 4.89 (s, 1H), 4.74 (AB, 1H, J=12.0 Hz), 4.69 (s, 2H), 4.54 (AB, 1H, J=12.0 Hz), 4.45 (AB, 1H, J=10.0 Hz), 4.10-4.14 (m, 2H), 2.03-2.12 (m, 4H), 1.98 (s, 3H), 1.88-1.93 (m, 4H), 1.55-1.63 (m, 1H). $^{13}$C NMR (100 MHz, CDCl$_3$): δ 169.73, 163.56, 151.01, 137.99, 136.69, 133.74, 128.83 (2C), 128.41 (2C), 128.34, 127.87 (2C), 127.77, 127.65 (2C), 109.15, 87.80, 86.25, 82.11, 81.29, 76.89, 72.54, 72.31, 70.40, 69.50, 29.26, 28.06, 21.20, 17.23, 13.87. FIRMS (ESI) calc'd for C$_{31}$H$_{35}$O$_8$N$_2$ [M+H]+m/z 563.2388. found 563.2400.

f) Preparation of Compound 54

To a solution of Compound 53 (0.166 g, 0.295 mmol) in ethyl acetate (10 mL) and methanol (10 mL) was added 20% (w/w) palladium hydroxide on carbon (0.01 g). The suspension was purged with H$_2$ and maintained under an atmosphere of H$_2$ for 8 h. The reaction mixture was then diluted with ethyl acetate, filtered through a pad of Celite® 545, and concentrated under reduced pressure. The residue was purified by flash column chromatography on silica gel with a solvent system of 1:9 hexanes-ethyl acetate to afford the alcohol (0.104 g, >95%) as a colorless foam.

Alcohol: R$_f$ 0.47 (9:1 hexanes-ethyl acetate). [α]$_D^{20}$+109 (c=0.31, methanol). IR (film) v 3410, 2935, 1701, 1269, 1057 cm$^{-1}$. $^1$H NMR (400 MHz, methanol-d4): δ 7.58 (d, 1H, J=0.8 Hz), 5.72 (d, 1H, J=0.4 Hz), 5.61 (s, 1H), 4.55 (s, 1H), 4.37 (s, 1H), 4.17 (dd, 1H, J=7.6, 2.8 Hz), 3.35 (s, 1H), 2.08-2.19 (m, 4H), 1.86-1.94 (m, 6H), 1.54-1.69 (m, 2H). $^{13}$C NMR (100 MHz, methanol-d4): δ 171.56, 166.37, 152.04, 136.98, 110.13, 88.31, 87.46, 82.28, 81.41, 76.89, 71.21, 30.19, 28.87, 20.97, 18.32, 12.82. HRMS (ESI) calc'd for C$_{16}$H$_{21}$O$_7$N$_2$ [M+H]+m/z 353.1343. found 353.1345.

To a solution of the alcohol from above (0.090 g, 0.260 mmol) in dichloromethane (12 mL) was added sequentially imidazole (0.106 g, 1.56 mmol) and triethylsilyl trifluoromethanesulfonate (0.142 mL, 0.780 mmol) at ambient temperature. The solution was heated to reflux and stirred until the starting material was completely consumed as indicated by TLC analysis. After approximately 30 min, the solution was cooled to ambient temperature and partitioned between dichloromethane (50 mL) and water (50 mL). The aqueous portion was separated and back-extracted with dichloromethane (2×50 mL), and the combined extracts were washed with 0.5 M aqueous HCl (50 mL), sat. sodium bicarbonate (50 mL), and brine (50 mL). The organic phase was collected, dried over magnesium sulfate, filtered, and concentrated under reduced pressure. The residue was purified by flash column chromatography on silica gel with a solvent system of 1:1 hexanes-ethyl acetate to afford Compound 54 (0.121 g, 88%) as a colorless oil.

Compound 54: $R_f$ 0.40 (1:1 hexanes-ethyl acetate). $[\alpha]_D^{20}$+56.5 (c=0.57, chloroform). IR (film) v 3207, 2955, 1694, 1463, 1233, 1066 cm$^{-1}$. $^1$H NMR (400 MHz, CDCl$_3$): δ 9.68 (br s, 1H), 7.41 (d, 1H, J=1.2 Hz), 5.73 (d, 1H, J=1.2 Hz), 5.58 (t, 1H, J=2.8 Hz), 4.52 (s, 1H), 4.28 (s, 1H), 4.11 (dd, 1H, J=7.6, 3.2 Hz), 2.00-2.09 (m, 4H), 1.92 (d, 3H, J=0.8 Hz), 1.81-1.91 (m, 3H), 1.51-1.63 (m, 2H), 0.96 (t, 9H, J=8.0 Hz), 0.65 (q, 6H, J=8.0 Hz). $^{13}$C NMR (100 MHz, CDCl$_3$): δ 169.75, 164.30, 150.47, 135.14, 109.56, 86.91, 86.30, 81.20, 80.04, 76.57, 69.66, 29.20, 27.98, 21.14, 17.25, 13.04, 6.72 (3C), 4.63 (3C). HRMS (ESI) calc'd for $C_{22}H_{35}O_7N_2Si$ [M+H]+m/z 467.2208. found 467.2216.

g) Preparation of Compound 55

To a solution of Compound 54 (118 mg, 0.253 mmol) in methanol (3 mL) was added potassium carbonate (3 mg, 0.025 mmol). The solution was stirred until complete consumption of the starting material was observed by TLC analysis. After approximately 12 h, water (0.5 mL) was added in one portion and the solution was partitioned between ethyl acetate (25 mL) and water (25 mL). The aqueous portion was back-extracted with ethyl acetate (3×25 mL) and the combined extracts were washed with brine. The organic phase was collected, dried over magnesium sulfate, filtered, and concentrated under reduced pressure. The residue was purified by flash column chromatography on silica gel with a solvent system of 1:2 hexanes-ethyl acetate to afford Compound 55 (75 mg, 70%) as a colorless oil.

Compound 55: $R_f$ 0.17 (1:1 hexanes-ethyl acetate). $[\alpha]_D^{20}$+38.5 (c=0.33, chloroform). IR (film) v 3444, 3204, 2955, 1694, 1273, 1064 cm$^{-1}$. $^1$H NMR (400 MHz, CDCl$_3$): δ 9.49 (br s, 1H), 7.54 (s, 1H), 5.88 (s, 1H), 4.44 (s, 1H), 4.36 (s, 1H), 4.18-4.22 (m, 2H), 2.70 (br s, 1H), 2.05-2.08 (m, 1H), 1.93 (s, 3H), 1.69-1.88 (m, 4H), 1.46-1.50 (m, 1H), 0.97 (t, 9H, J=8.0 Hz), 0.62-0.68 (q, 6H, J=8.0 Hz). $^{13}$C NMR (100 MHz, CDCl$_3$): δ 164.18, 150.72, 135.51, 110.02, 88.83, 86.52, 81.38, 80.10, 76.46, 67.84, 29.44 (2C), 16.63, 12.83, 6.75 (3C), 4.65 (3C). HRMS (ESI) calc'd for $C_{20}H_{33}O_6N_2Si$ [M+H]+m/z 425.2112. found 425.2102.

h) Preparation of Compound 56 from Compound 53

To a solution of Compound 56 (0.166 g, 0.295 mmol) in ethyl acetate (10 mL) and methanol (10 mL) was added 20% (w/w) palladium hydroxide on carbon (0.01 g). The suspension was purged with H$_2$. After 8 h under an atmosphere of H$_2$, the reaction mixture was diluted with ethyl acetate, filtered through a pad of Celite® 545, and concentrated under reduced pressure. The residue was purified by flash column chromatography on silica gel with a solvent system of 1:9 hexanes-ethyl acetate to afford the alcohol (0.104 g, >95% yield) as a colorless foam.

Alcohol: $R_f$ 0.47 (9:1 hexanes-ethyl acetate). $[\alpha]_D^{20}$+109 (c=0.31, methanol). IR (film) v 3410, 2935, 1701, 1269, 1057 cm$^{-1}$. $^1$H NMR (400 MHz, methanol-d4): δ 7.58 (d, 1H, J=0.8 Hz), 5.72 (d, 1H, J=0.4 Hz), 5.61 (s, 1H), 4.55 (s, 1H), 4.37 (s, 1H), 4.17 (dd, 1H, J=7.6, 2.8 Hz), 3.35 (s, 1H), 2.08-2.19 (m, 4H), 1.86-1.94 (m, 6H), 1.54-1.69 (m, 2H). $^{13}$C NMR (methanol-d4): δ 171.56, 166.37, 152.04, 136.98, 110.13, 88.31, 87.46, 82.28, 81.41, 76.89, 71.21, 30.19, 28.87, 20.97, 18.32, 12.82. HRMS (ESI) calc'd for $C_{16}H_{21}O_7N_2$ [M+H]+m/z 353.1343. found 353.1345.

To a solution of the alcohol from above (0.044 g, 0.12 mmol) in dichloromethane (2 mL) was sequentially added triethylamine (52 µL, 0.56 mmol), pnitrobenzoyl chloride (0.061 g, 0.31 mmol) and 4-(dimethylamino)pyridine (0.008 g, 0.62 mmol). After 10 h of stirring, the solution was partitioned between dichloromethane (5 mL) and water (5 mL). The aqueous portion was separated, back-extracted with dichloromethane (2×5 mL), and the combined extracts were sequentially washed with 1 M aqueous HCl (5 mL), sat. sodium bicarbonate (5 mL), and brine (5 mL). The organic layer was collected, dried through a phase separator cartridge and concentrated under reduced pressure. The resulting residue was purified by flash column chromatography on silica gel with a solvent system of 1:3 hexanes-ethyl acetate to provide Compound 56 (0.057 g, 90%) as a colorless solid. Compound 56 was recrystallized from ethyl acetate-hexanes and the stereochemistry was confirmed by X-ray crystallography.

Compound 56: $R_f$ 0.22 (1:2 hexanes-ethyl acetate). m.p. 213-214° C. (ethyl acetate-hexanes). $[\alpha]_D^{20}$+42.3 (c=1.0, chloroform). IR (KBr disc) v 3310, 3104, 2958, 1735, 1711, 1684, 1607, 1527, 1346, 1267, 1232, 1105, 1073, 1022 cm$^{-1}$. $^1$H NMR (300 MHz, CDCl$_3$): δ 8.78 (s, 1H), 8.36 (d, 2H, J=8.9 Hz), 8.21 (d, 2H, J=8.9 Hz, 7.45 (d, 1H, J=1.1 Hz), 5.86 (d, 1H, J=1.2 Hz), 5.78 (t, 1H, J=2.4 Hz), 5.51 (s, 1H), 5.07 (s, 1H), 4.26 (dd, 1H, J=10.5, 7.3 Hz), 2.08-2.18 (m, 4H), 1.59-2.04 (m, 7H), 1.43-1.57 (m, 1H). $^{13}$C NMR (75 MHz, CDCl$_3$): δ 169.38, 163.70, 163.52, 151.26, 150.15, 134.66, 133.89, 131.13 (2C), 124.18 (2C), 110.09, 86.96, 86.46, 80.70, 78.72, 76.40, 68.39, 29.61, 28.47, 21.12, 17.03, 13.21. HRMS (ESI) calc'd for $C_{23}H_{24}O_{10}N_3$ [M+H]+m/z 502.1456. found 502.1455.

Example 19

Preparation of Compound 57

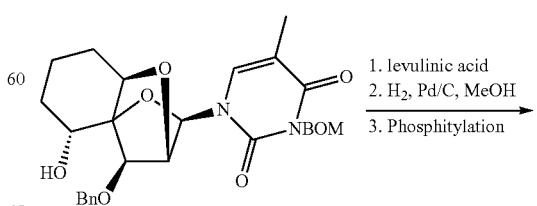

52

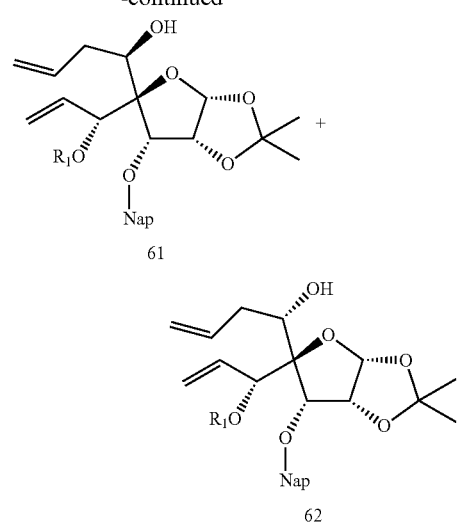

57 levulinic acid = 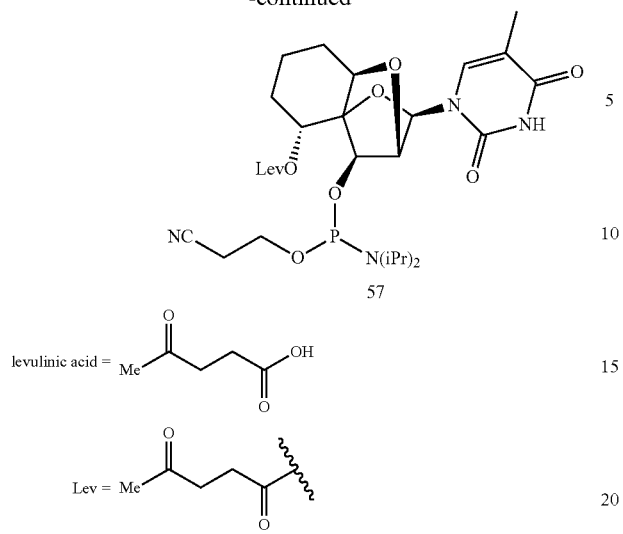

Lev = 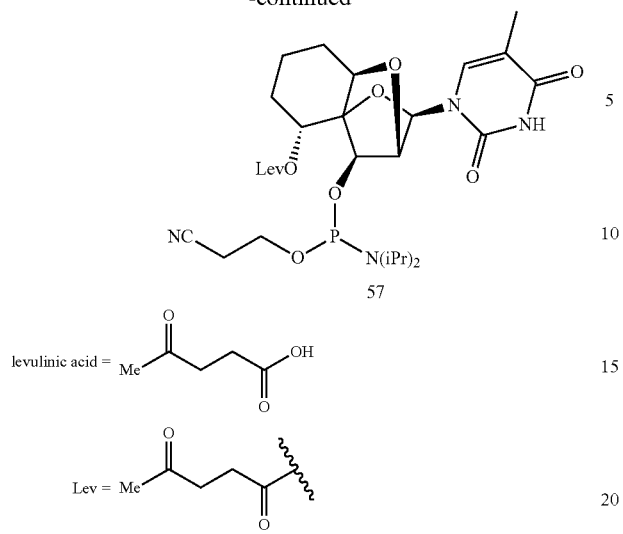

Compound 51 is prepared as per the procedure illustrated in Example 18.

Example 20

Preparation of Compound 69

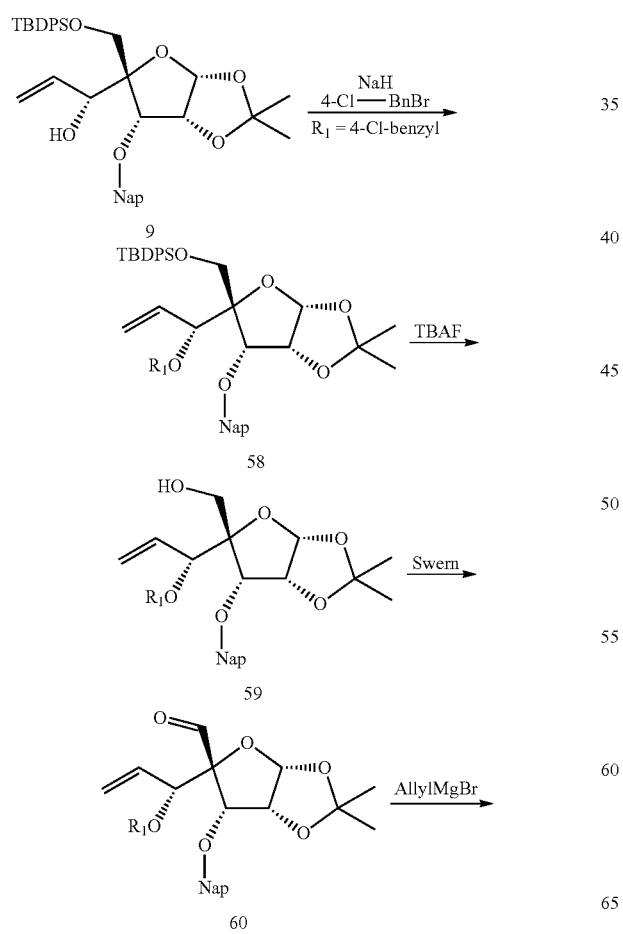

Compound 62 $\xrightarrow{\text{Ac}_2\text{O}\\ \text{pyridine}}$

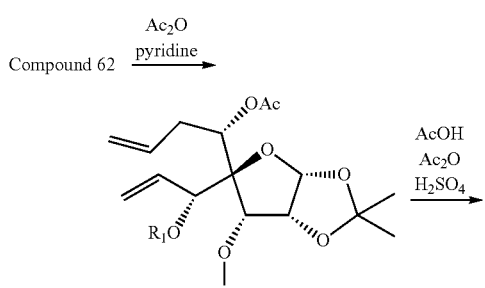 $\xrightarrow{\text{AcOH}\\ \text{Ac}_2\text{O}\\ \text{H}_2\text{SO}_4}$

63

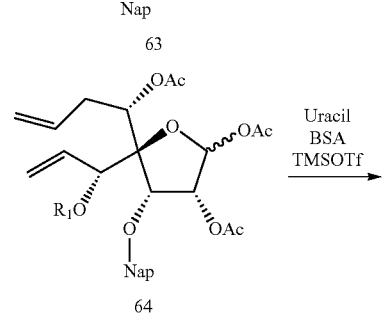 $\xrightarrow{\text{Uracil}\\ \text{BSA}\\ \text{TMSOTf}}$

64

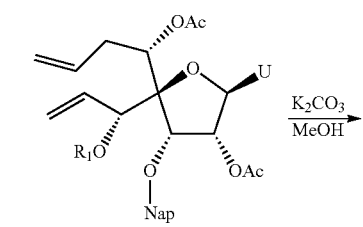 $\xrightarrow{\text{K}_2\text{CO}_3\\ \text{MeOH}}$

65

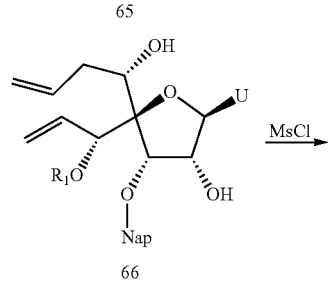 $\xrightarrow{\text{MsCl}}$

66

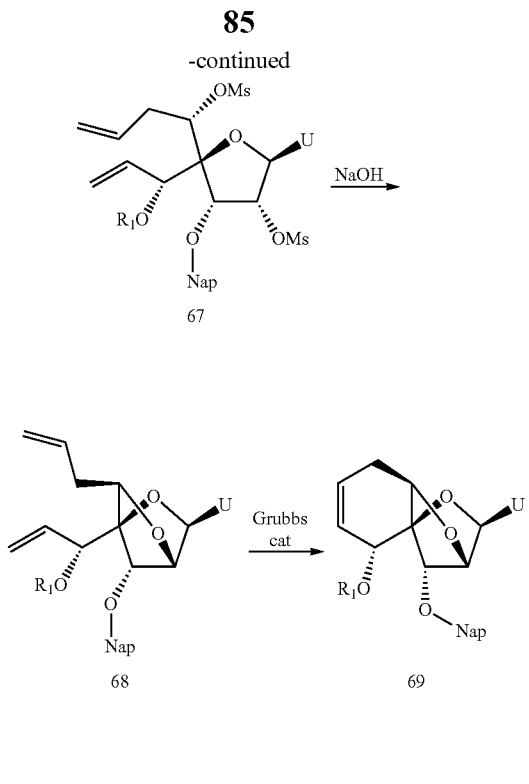

Compound 9 is prepared as per the procedure illustrated in Example 14.

Example 21

Preparation of Compounds 72 and 73

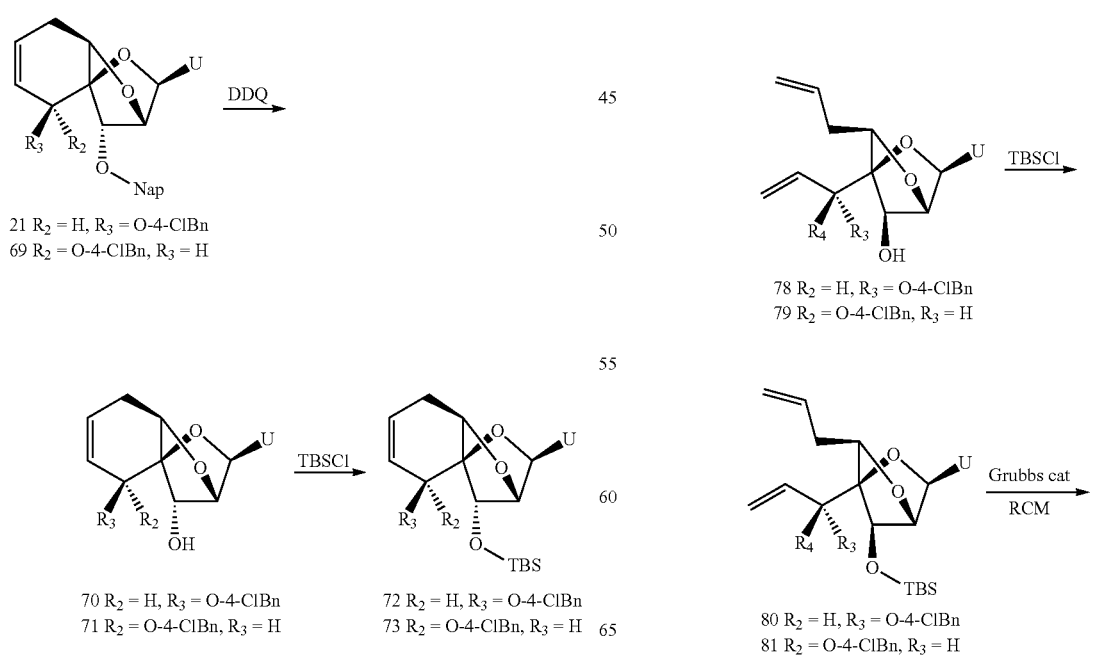

70 R$_2$ = H, R$_3$ = O-4-ClBn
71 R$_2$ = O-4-ClBn, R$_3$ = H

72 R$_2$ = H, R$_3$ = O-4-ClBn
73 R$_2$ = O-4-ClBn, R$_3$ = H

Compounds 21 and 69 are prepared as per the procedures illustrated in Examples 14 and 20, respectively.

Example 22

Preparation of Compounds 82 and 83

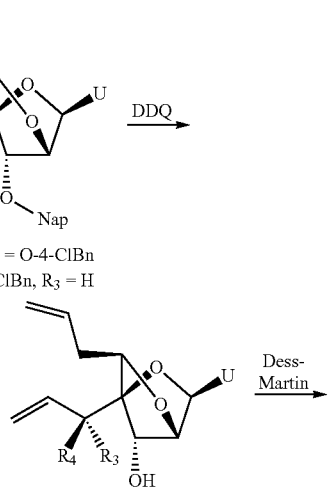

20 R$_2$ = H, R$_3$ = O-4-ClBn
68 R$_2$ = O-4-ClBn, R$_3$ = H

74 R$_2$ = H, R$_3$ = O-4-ClBn
75 R$_2$ = O-4-ClBn, R$_3$ = H

76 R$_2$ = H, R$_3$ = O-4-ClBn
77 R$_2$ = O-4-ClBn, R$_3$ = H

78 R$_2$ = H, R$_3$ = O-4-ClBn
79 R$_2$ = O-4-ClBn, R$_3$ = H

80 R$_2$ = H, R$_3$ = O-4-ClBn
81 R$_2$ = O-4-ClBn, R$_3$ = H

87
-continued

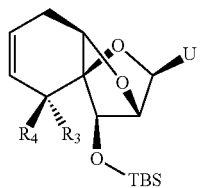

82 R$_2$ = H, R$_3$ = O-4-ClBn
843 R$_2$ = O-4-ClBn, R$_3$ = H

Compounds 20 and 68 are prepared as per the procedures illustrated in Examples 14 and 20, respectively.

Example 23

Preparation of Compounds 96-99

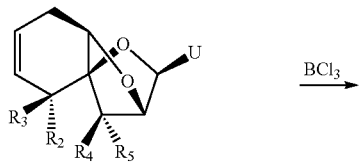   BCl$_3$ →

72 R$_2$ = H, R$_3$ = O-4-ClBn, R$_4$ = H, R$_5$ = OTBS
73 R$_2$ = O-4-ClBn, R$_3$ = H, R$_4$ = H, R$_5$ = OTBS
82 R$_2$ = H, R$_3$ = O-4-ClBn, R$_4$ = OTBS, R$_5$ = H
83 R$_2$ = O-4-ClBn, R$_3$ = H, R$_4$ = OTBS, R$_5$ = H

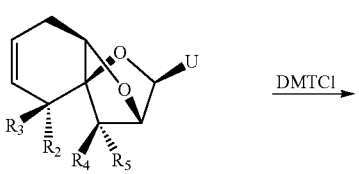   DMTCl →

84 R$_2$ = H, R$_3$ = OH, R$_4$ = H, R$_5$ = OTBS
85 R$_2$ = OH, R$_3$ = H, R$_4$ = H, R$_5$ = OTBS
86 R$_2$ = H, R$_3$ = OH, R$_4$ = OTBS, R$_5$ = H
87 R$_2$ = OH, R$_3$ = H, R$_4$ = OTBS, R$_5$ = H

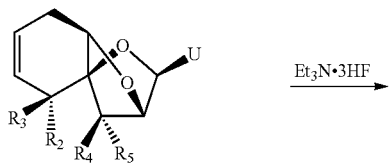   Et$_3$N•3HF →

88 R$_2$ = H, R$_3$ = ODMT, R$_4$ = H, R$_5$ = OTBS
89 R$_2$ = ODMT, R$_3$ = H, R$_4$ = H, R$_5$ = OTBS
90 R$_2$ = H, R$_3$ = ODMT, R$_4$ = OTBS, R$_5$ = H
91 R$_2$ = ODMT, R$_3$ = H, R$_4$ = OTBS, R$_5$ = H

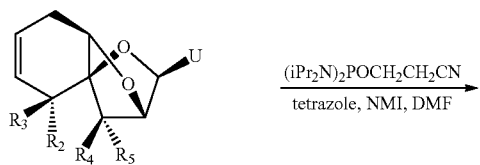   (iPr$_2$N)$_2$POCH$_2$CH$_2$CN / tetrazole, NMI, DMF →

92 R$_2$ = H, R$_3$ = ODMT, R$_4$ = H, R$_5$ = OH
93 R$_2$ = ODMT, R$_3$ = H, R$_4$ = H, R$_5$ = OH
94 R$_2$ = H, R$_3$ = ODMT, R$_4$ = OH, R$_5$ = H
95 R$_2$ = ODMT, R$_3$ = H, R$_4$ = OH, R$_5$ = H

88
-continued

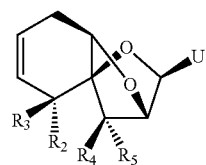

96 R$_2$ = H, R$_3$ = ODMT, R$_4$ = H, R$_5$ = OP(NiPr$_2$)OCH$_2$CH$_2$CN
97 R$_2$ = ODMT, R$_3$ = H, R$_4$ = H, R$_5$ = OP(NiPr$_2$)OCH$_2$CH$_2$CN
98 R$_2$ = H, R$_3$ = ODMT, R$_4$ = OP(NiPr$_2$)OCH$_2$CH$_2$CN, R$_5$ = H
99 R$_2$ = ODMT, R$_3$ = H, R$_4$ = OP(NiPr$_2$)OCH$_2$CH$_2$CN, R$_5$ = H

Compounds 72, 73, 82 and 83 are prepared as per the procedures illustrated in Examples 21 and 22, respectively. In the tritylation step, other hydroxyl protecting groups can be used in place of DMTCl (e.g. levulinic acid).

Example 24

Preparation of Compounds 116-119

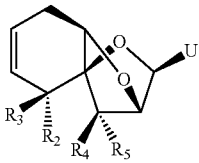   Pd/C, H$_2$ →

72 R$_2$ = H, R$_3$ = O-4-ClBn, R$_4$ = H, R$_5$ = OTBS
73 R$_2$ = O-4-ClBn, R$_3$ = H, R$_4$ = H, R$_5$ = OTBS
82 R$_2$ = H, R$_3$ = O-4-ClBn, R$_4$ = OTBS, R$_5$ = H
83 R$_2$ = O-4-ClBn, R$_3$ = H, R$_4$ = OTBS, R$_5$ = H

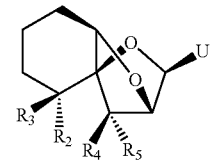   BCl$_3$ →

100 R$_2$ = H, R$_3$ = O-4-ClBn, R$_4$ = H, R$_5$ = OTBS
101 R$_2$ = O-4-ClBn, R$_3$ = H, R$_4$ = H, R$_5$ = OTBS
102 R$_2$ = H, R$_3$ = O-4-ClBn, R$_4$ = OTBS, R$_5$ = H
103 R$_2$ = O-4-ClBn, R$_3$ = H, R$_4$ = OTBS, R$_5$ = H

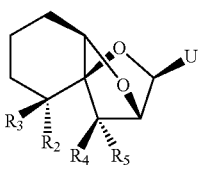   DMTCl →

104 R$_2$ = H, R$_3$ = OH, R$_4$ = H, R$_5$ = OTBS
105 R$_2$ = OH, R$_3$ = H, R$_4$ = H, R$_5$ = OTBS
106 R$_2$ = H, R$_3$ = OH, R$_4$ = OTBS, R$_5$ = H
107 R$_2$ = OH, R$_3$ = H, R$_4$ = OTBS, R$_5$ = H

89
-continued

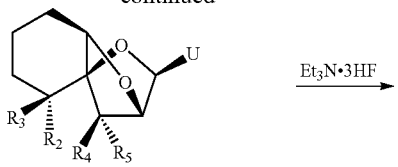

108 R₂ = H, R₃ = ODMT, R₄ = H, R₅ = OTBS
109 R₂ = ODMT, R₃ = H, R₄ = H, R₅ = OTBS
110 R₂ = H, R₃ = ODMT, R₄ = OTBS, R₅ = H
111 R₂ = ODMT, R₃ = H, R₄ = OTBS, R₅ = H

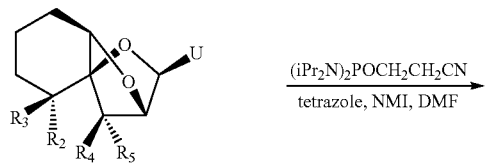

112 R₂ = H, R₃ = ODMT, R₄ = H, R₅ = OH
113 R₂ = ODMT, R₃ = H, R₄ = H, R₅ = OH
114 R₂ = H, R₃ = ODMT, R₄ = OH, R₅ = H
115 R₂ = ODMT, R₃ = H, R₄ = OH, R₅ = H

90
-continued

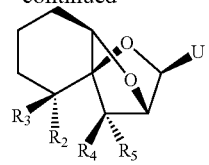

116 R₂ = H, R₃ = ODMT, R₄ = H, R₅ = OP(NiPr₂)OCH₂CH₂CN
117 R₂ = ODMT, R₃ = H, R₄ = H, R₅ = OP(NiPr₂)OCH₂CH₂CN
118 R₂ = H, R₃ = ODMT, R₄ = OP(NiPr₂)OCH₂CH₂CN, R₅ = H
119 R₂ = ODMT, R₃ = H, R₄ = OP(NiPr₂)OCH₂CH₂CN, R₅ = H

Compounds 72, 73, 82 and 83 are prepared as per the procedures illustrated in Examples 21 and 22, respectively. In the tritylation step, other hydroxyl protecting groups can be used in place of DMTCl (e.g. levulinic acid).

Example 25

Preparation of Compounds 122, 123 and 128-131

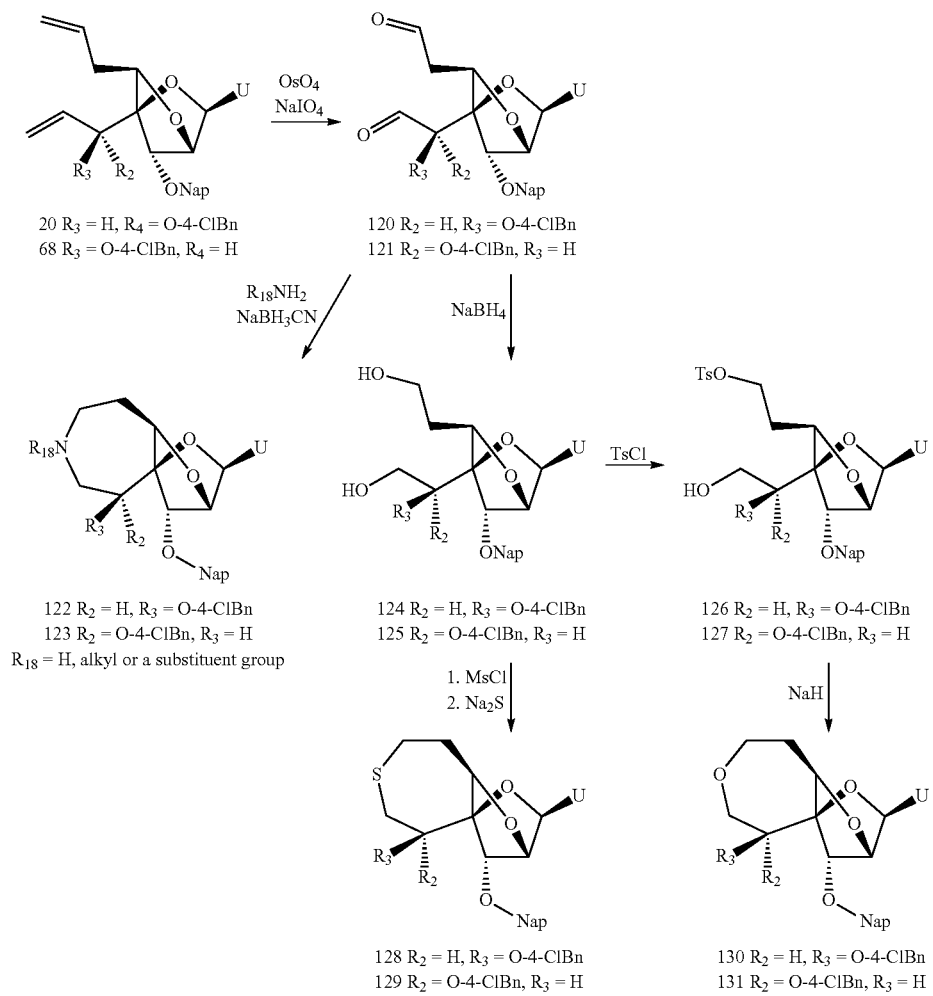

Compounds 20 and 68 are prepared as per the procedures illustrated in Examples 14 and 20, respectively.

Example 26
Preparation of Compounds 134, 135 and 140-143
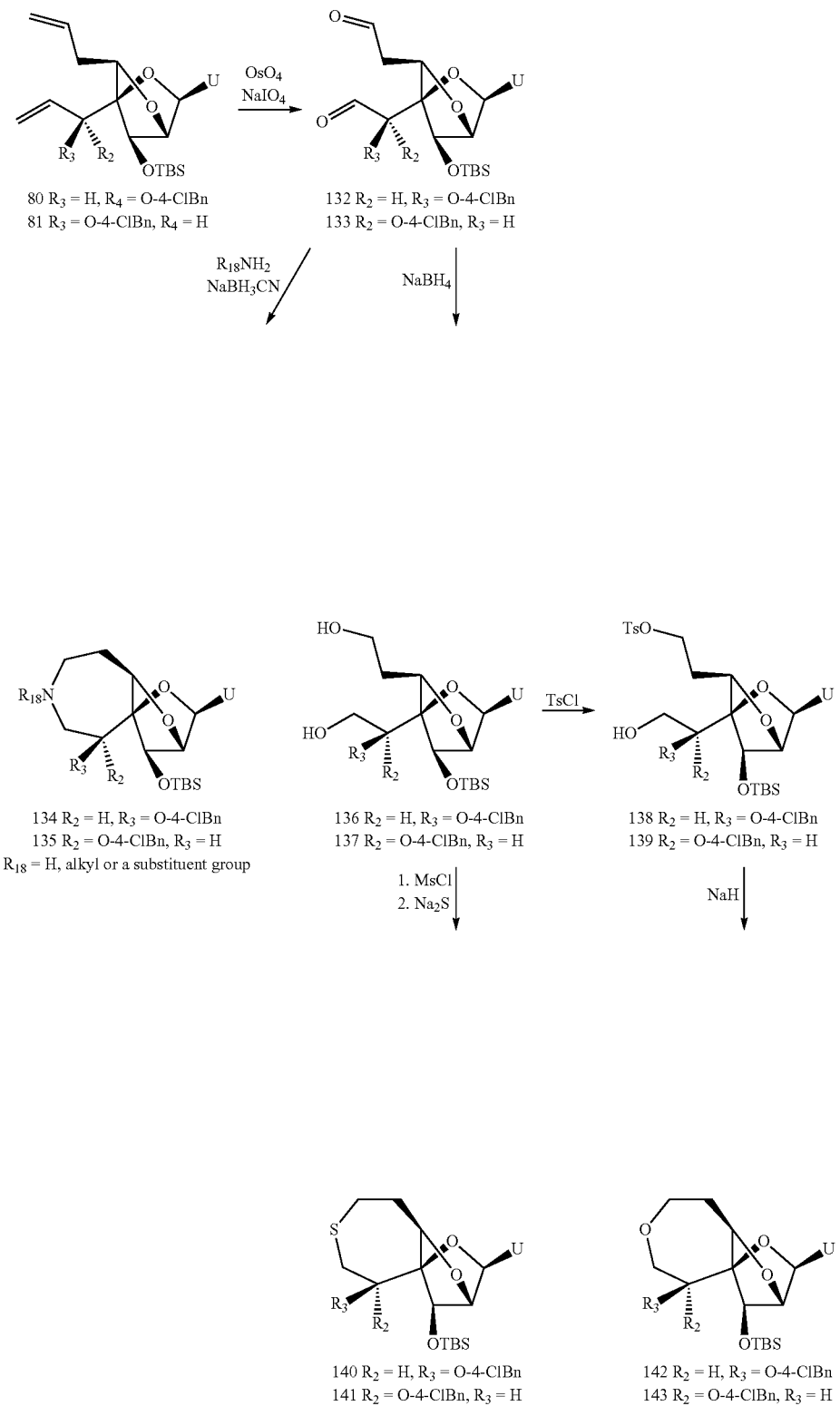

Compounds 80 and 81 are prepared as per the procedures illustrated in Example 22.

Compounds 122, 123, 128-131 are prepared as per the procedures illustrated in Example 25.

Example 27

Preparation of Compounds 150-155

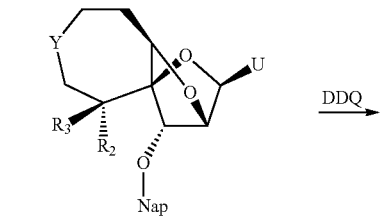

122 Y = NR$_{18}$, R$_2$ = H, R$_3$ = O-4-ClBn
123 Y = NR$_{18}$, R$_2$ = O-4-ClBn, R$_3$ = H
128 Y = S, R$_2$ = H, R$_3$ = O-4-ClBn
129 Y = S, R$_2$ = O-4-ClBn, R$_3$ = H
130 Y = O, R$_2$ = H, R$_3$ = O-4-ClBn
131 Y = O, R$_2$ = O-4-ClBn, R$_3$ = H

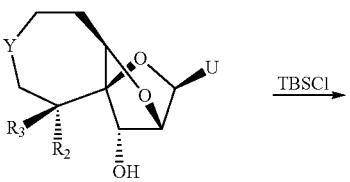

144 Y = NR$_{18}$, R$_2$ = H, R$_3$ = O-4-ClBn
145 Y = NR$_{18}$, R$_2$ = O-4-ClBn, R$_3$ = H
146 Y = S, R$_2$ = H, R$_3$ = O-4-ClBn
147 Y = S, R$_2$ = O-4-ClBn, R$_3$ = H
148 Y = O, R$_2$ = H, R$_3$ = O-4-ClBn
149 Y = O, R$_2$ = O-4-ClBn, R$_3$ = H

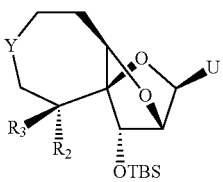

150 Y = NR$_{18}$, R$_2$ = H, R$_3$ = O-4-ClBn
151 Y = NR$_{18}$, R$_2$ = O-4-ClBn, R$_3$ = H
152 Y = S, R$_2$ = H, R$_3$ = O-4-ClBn
153 Y = S, R$_2$ = O-4-ClBn, R$_3$ = H
154 Y = O, R$_2$ = H, R$_3$ = O-4-ClBn
155 Y = O, R$_2$ = O-4-ClBn, R$_3$ = H

R$_{18}$ is H, alkyl or a substituent group.

Example 28

Preparation of Compounds 192-203

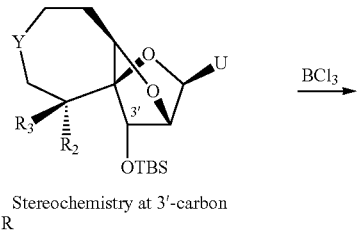

Stereochemistry at 3'-carbon
S   R
134  150 Y = NR$_{18}$, R$_2$ = H, R$_3$ = O-4-ClBn
135  151 Y = NR$_{18}$, R$_2$ = O-4-ClBn, R$_3$ = H
140  152 Y = S, R$_2$ = H, R$_3$ = O-4-ClBn
141  153 Y = S, R$_2$ = O-4-ClBn, R$_3$ = H
142  154 Y = O, R$_2$ = H, R$_3$ = O-4-ClBn
143  155 Y = O, R$_2$ = O-4-ClBn, R$_3$ = H

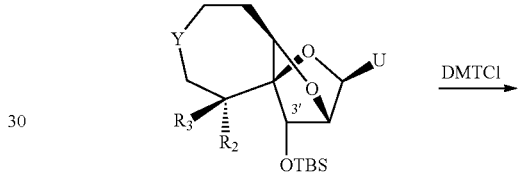

S   R
156  157 Y = NR$_{18}$, R$_2$ = H, R$_3$ = OH
158  159 Y = NR$_{18}$, R$_2$ = OH, R$_3$ = H
160  161 Y = S, R$_2$ = H, R$_3$ = OH
162  163 Y = S, R$_2$ = OH, R$_3$ = H
164  165 Y = O, R$_2$ = H, R$_3$ = OH
166  167 Y = O, R$_2$ = OH, R$_3$ = H

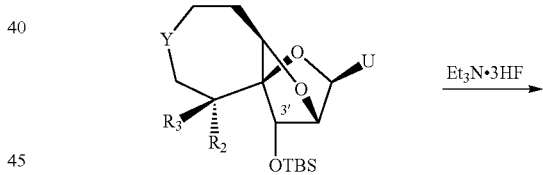

S   R
168  169 Y = NR$_{18}$, R$_2$ = H, R$_3$ = ODMT
170  171 Y = NR$_{18}$, R$_2$ = ODMT, R$_3$ = H
172  173 Y = S, R$_2$ = H, R$_3$ = ODMT
174  175 Y = S, R$_2$ = ODMT, R$_3$ = H
176  177 Y = O, R$_2$ = H, R$_3$ = ODMT
178  179 Y = O, R$_2$ = ODMT, R$_3$ = H

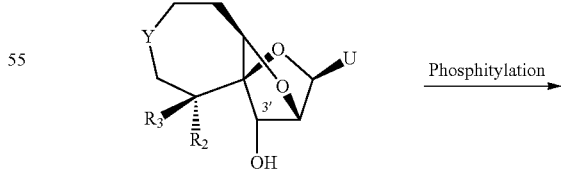

S   R
180  181 Y = NR$_{18}$, R$_2$ = H, R$_3$ = ODMT
182  183 Y = NR$_{18}$, R$_2$ = ODMT, R$_3$ = H
184  185 Y = S, R$_2$ = H, R$_3$ = ODMT
186  187 Y = S, R$_2$ = ODMT, R$_3$ = H
188  189 Y = O, R$_2$ = H, R$_3$ = ODMT
190  191 Y = O, R$_2$ = ODMT, R$_3$ = H

-continued

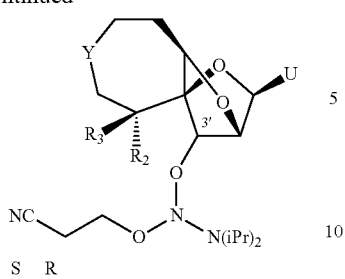

| S | R | |
|---|---|---|
| 192 | 193 | Y = NR$_{18}$, R$_2$ = H, R$_3$ = ODMT |
| 194 | 195 | Y = NR$_{18}$, R$_2$ = ODMT, R$_3$ = H |
| 196 | 197 | Y = S, R$_2$ = H, R$_3$ = ODMT |
| 198 | 199 | Y = S, R$_2$ = ODMT, R$_3$ = H |
| 200 | 201 | Y = O, R$_2$ = H, R$_3$ = ODMT |
| 202 | 203 | Y = O, R$_2$ = ODMT, R$_3$ = H |

Compounds 134, 135, 140-143, and 150-155 are prepared as per the procedures illustrated in Examples 26 and 27, respectively. In the tritylation step, other hydroxyl protecting groups can be used in place of DMTCl (e.g. levulinic acid). Each of the 3'-(S) and (R) isomers is prepared using either 3'S or R starting material as indicated.

Example 29

Preparation of Compound 211

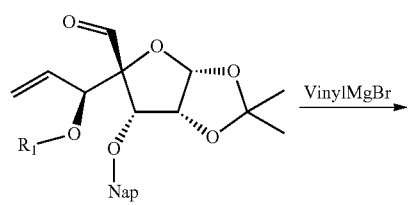

12

$\xrightarrow{\text{VinylMgBr}}$

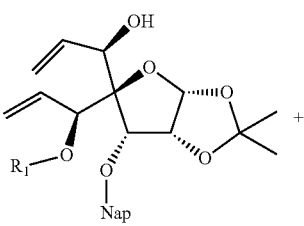

204

+

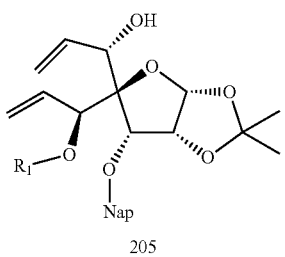

205

Compound 205 $\xrightarrow[\text{pyridine}]{\text{Ac}_2\text{O}}$

-continued

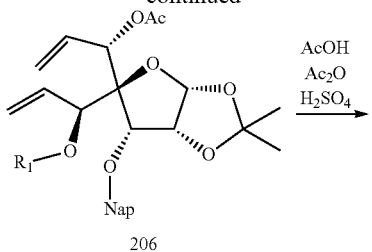

206

$\xrightarrow[\text{H}_2\text{SO}_4]{\text{AcOH, Ac}_2\text{O}}$

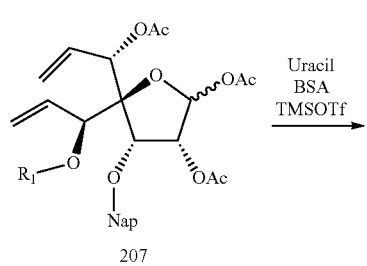

207

$\xrightarrow[\text{TMSOTf}]{\text{Uracil, BSA}}$

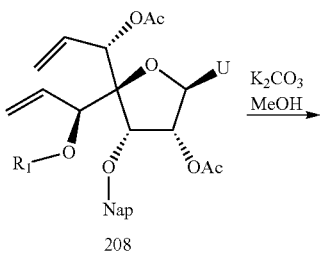

208

$\xrightarrow[\text{MeOH}]{\text{K}_2\text{CO}_3}$

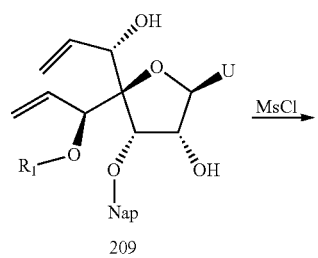

209

$\xrightarrow{\text{MsCl}}$

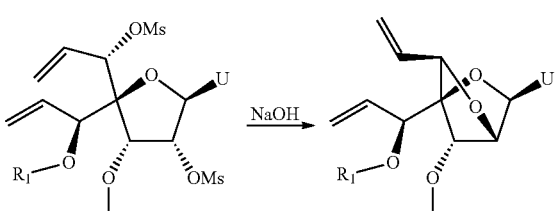

210     211

R$_1$ = 4-Cl-benzyl

Compound 12 is prepared as per the procedure illustrated in Example 14.
Example 30
Preparation of Compound 219
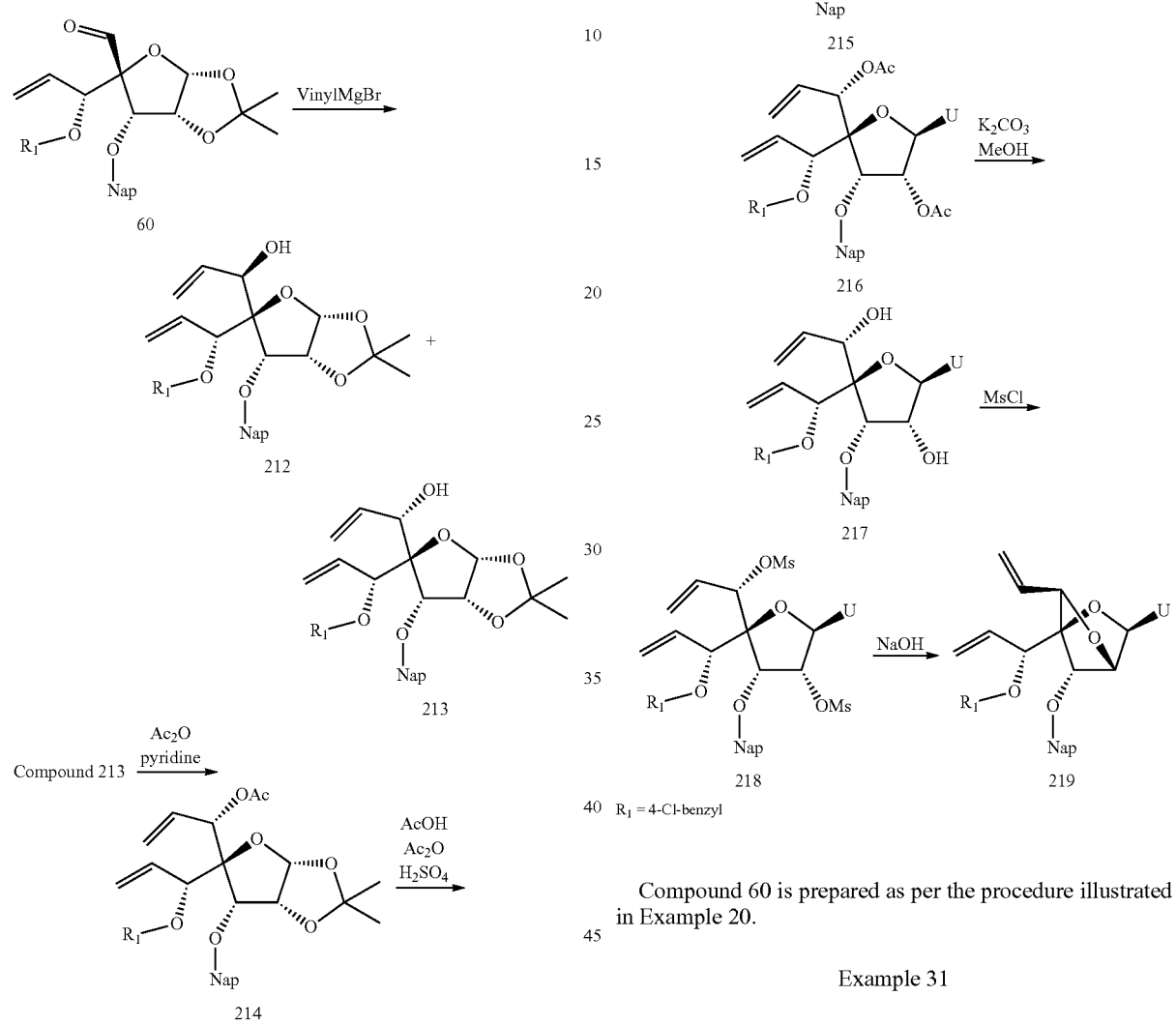
$R_1$ = 4-Cl-benzyl
Compound 60 is prepared as per the procedure illustrated in Example 20.
Example 31
Preparation of Compounds 222, 223 and 228-231
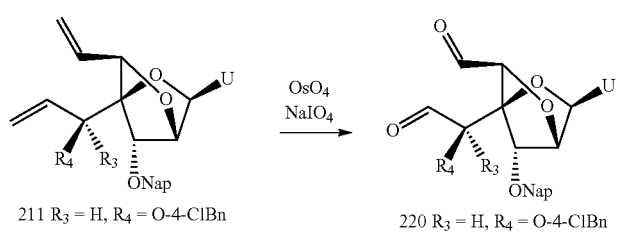

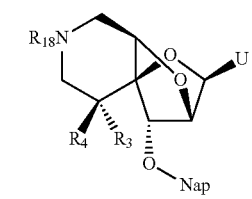
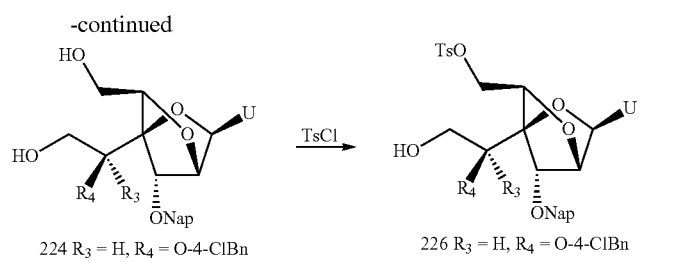
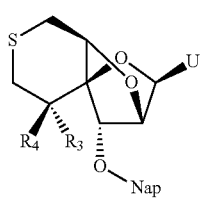
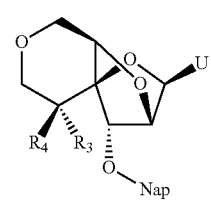
Compounds 211 and 219 are prepared as per the procedure illustrated in Examples 29 and 30, respectively.
Example 32
Preparation of Compounds 242, 243 and 248-251
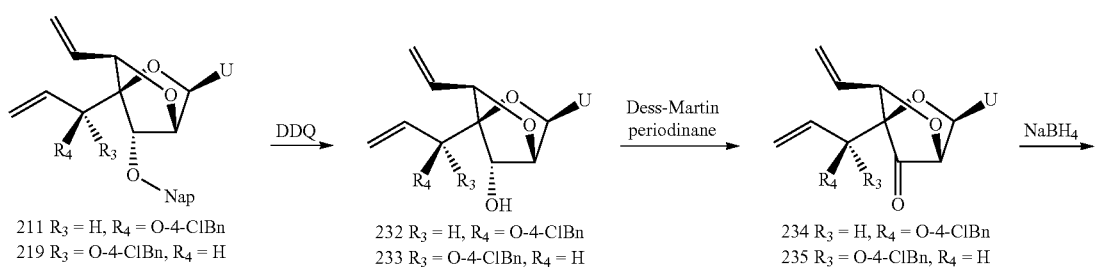
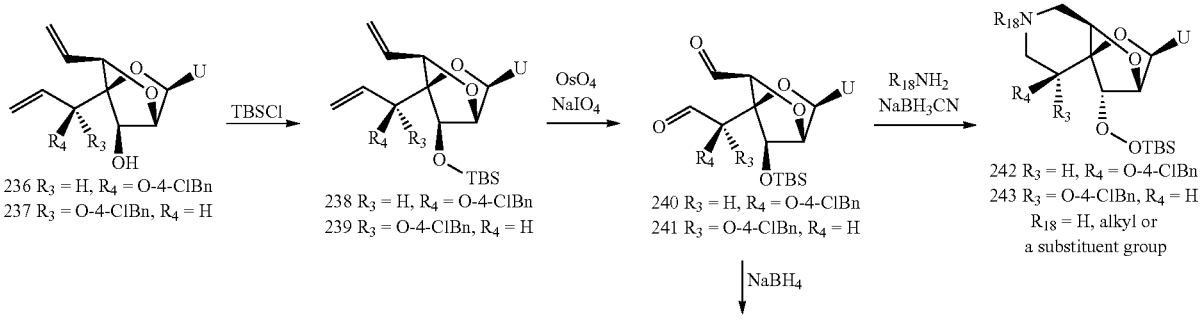

-continued

246 R$_3$ = H, R$_4$ = O-4-ClBn
247 R$_3$ = O-4-ClBn, R$_4$ = H

244 R$_3$ = H, R$_4$ = O-4-ClBn
245 R$_3$ = O-4-ClBn, R$_4$ = H

TsCl

NaH ↓

1. MsCl
2. Na$_2$S ↓

250 R$_3$ = H, R$_4$ = O-4-ClBn
251 R$_3$ = O-4-ClBn, R$_4$ = H

248 R$_3$ = H, R$_4$ = O-4-ClBn
249 R$_3$ = O-4-ClBn, R$_4$ = H

Compounds 211 and 219 are prepared as per the procedure illustrated in Examples 29 and 30, respectively.

Compounds 222, 223, and 228-231 are prepared as per the procedure illustrated in Example 31.

Example 33

Preparation of Compounds 252-257

Example 34

Preparation of Compounds 294-305

222 Y = NR$_{18}$, R$_3$ = H, R$_4$ = O-4-ClBn
223 Y = NR$_{18}$, R$_3$ = O-4-ClBn, R$_4$ = H
228 Y = S, R$_3$ = H, R$_4$ = O-4-ClBn
229 Y = S, R$_3$ = O-4-ClBn, R$_4$ = H
230 Y = O, R$_3$ = H, R$_4$ = O-4-ClBn
231 Y = O, R$_3$ = O-4-ClBn, R$_4$ = H

1. DDQ
2. TBSCl

Stereochemistry at 3'-carbon

S   R
242 252 Y = NR$_{18}$, R$_3$ = H, R$_4$ = O-4-ClBn
243 253 Y = NR$_{18}$, R$_3$ = O-4-ClBn, R$_4$ = H
244 254 Y = S, R$_3$ = H, R$_4$ = O-4-ClBn
249 255 Y = S, R$_3$ = O-4-ClBn, R$_4$ = H
250 256 Y = O, R$_3$ = H, R$_4$ = O-4-ClBn
251 257 Y = O, R$_3$ = O-4-ClBn, R$_4$ = H

BCl$_3$

252 Y = NR$_{18}$, R$_3$ = H, R$_4$ = O-4-ClBn
253 Y = NR$_{18}$, R$_3$ = O-4-ClBn, R$_4$ = H
254 Y = S, R$_3$ = H, R$_4$ = O-4-ClBn
255 Y = S, R$_3$ = O-4-ClBn, R$_4$ = H
256 Y = O, R$_3$ = H, R$_4$ = O-4-ClBn
257 Y = O, R$_3$ = O-4-ClBn, R$_4$ = H

DMTCl

S   R
258 259 Y = NR$_{18}$, R$_3$ = H, R$_4$ = OH
260 261 Y = NR$_{18}$, R$_3$ = OH, R$_4$ = H
262 263 Y = S, R$_3$ = H, R$_4$ = OH
264 265 Y = S, R$_3$ = OH, R$_4$ = H
266 267 Y = O, R$_3$ = H, R$_4$ = OH
268 269 Y = O, R$_3$ = OH, R$_4$ = H

R$_{18}$ is H, alkyl or a substituent group.

103
-continued

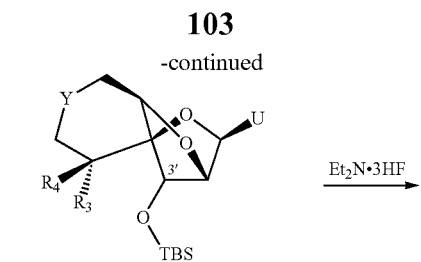

 Et$_2$N·3HF →

| S | R |
|---|---|
| 270 | 271 Y = NR$_{18}$, R$_3$ = H, R$_4$ = ODMT |
| 272 | 273 Y = NR$_{18}$, R$_3$ = ODMT, R$_4$ = H |
| 274 | 275 Y = S, R$_3$ = H, R$_4$ = ODMT |
| 276 | 277 Y = S, R$_3$ = ODMT, R$_4$ = H |
| 278 | 279 Y = O, R$_3$ = H, R$_4$ = ODMT |
| 280 | 281 Y = O, R$_3$ = ODMT, R$_4$ = H |

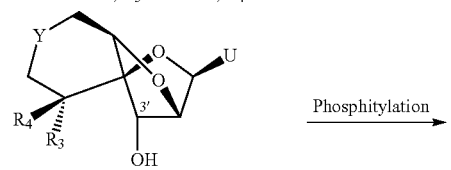

 Phosphitylation →

| S | R |
|---|---|
| 282 | 283 Y = NR$_{18}$, R$_3$ = H, R$_4$ = ODMT |
| 284 | 285 Y = NR$_{18}$, R$_3$ = ODMT, R$_4$ = H |
| 286 | 287 Y = S, R$_3$ = H, R$_4$ = ODMT |
| 288 | 289 Y = S, R$_3$ = ODMT, R$_4$ = H |
| 290 | 291 Y = O, R$_3$ = H, R$_4$ = ODMT |
| 292 | 293 Y = O, R$_3$ = ODMT, R$_4$ = H |

104
-continued

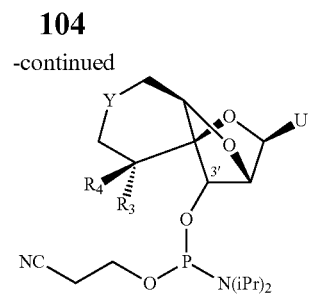

| S | R |
|---|---|
| 294 | 295 Y = NR$_{18}$, R$_3$ = H, R$_4$ = ODMT |
| 296 | 297 Y = NR$_{18}$, R$_3$ = ODMT, R$_4$ = H |
| 298 | 299 Y = S, R$_3$ = H, R$_4$ = ODMT |
| 300 | 301 Y = S, R$_3$ = ODMT, R$_4$ = H |
| 302 | 302 Y = O, R$_3$ = H, R$_4$ = ODMT |
| 303 | 304 Y = O, R$_3$ = ODMT, R$_4$ = H |

$R_{18}$ is H, alkyl or a substituent group.

Compounds 242, 243, 248-251 and 252-257 are prepared as per the procedure illustrated in Examples 32 and 33. In the tritylation step, other hydroxyl protecting groups can be used in place of DMTC1 (e.g. levulinic acid). Each of the 3'-(S) and (R) isomers is prepared using either 3'-(S) or (R) starting material as indicated.

Example 35

Preparation of Compound 322

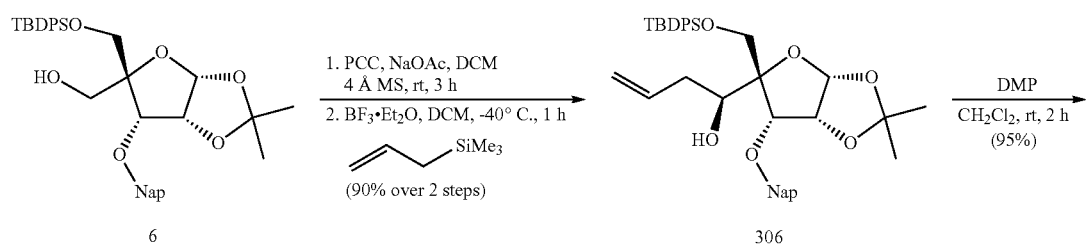

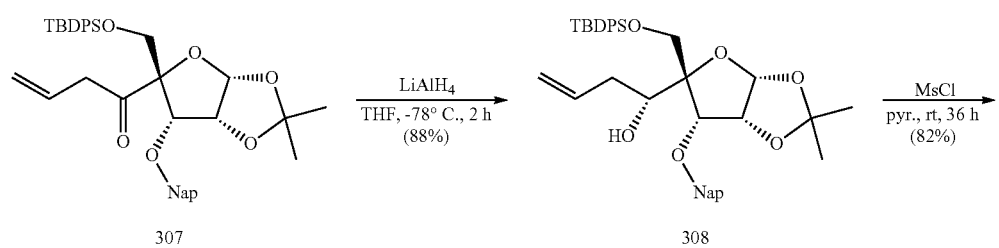

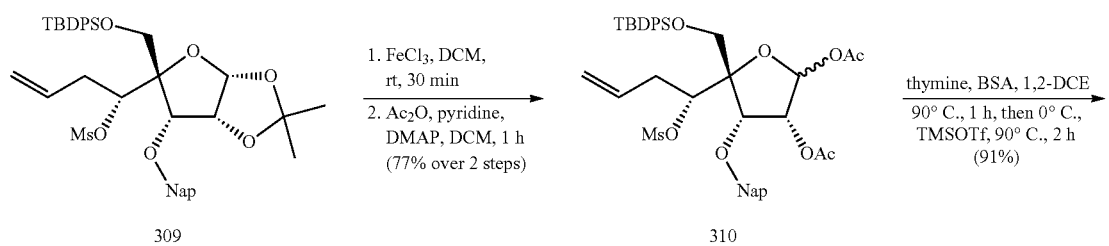

-continued
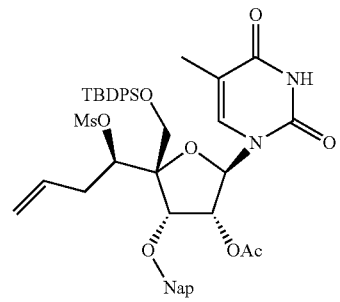
311
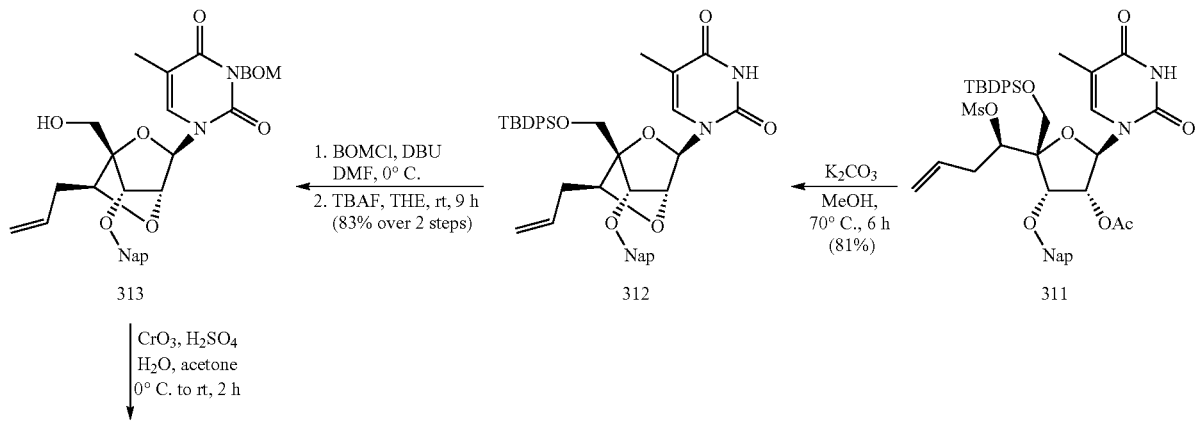
313 → 312 → 311
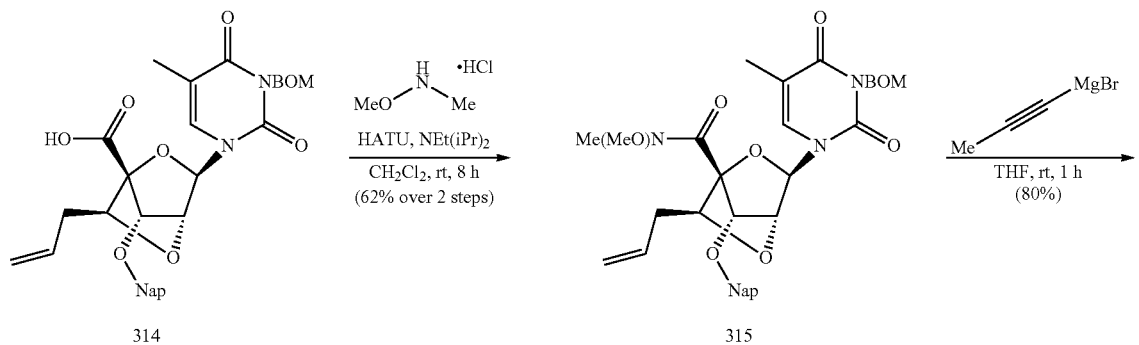
314 → 315
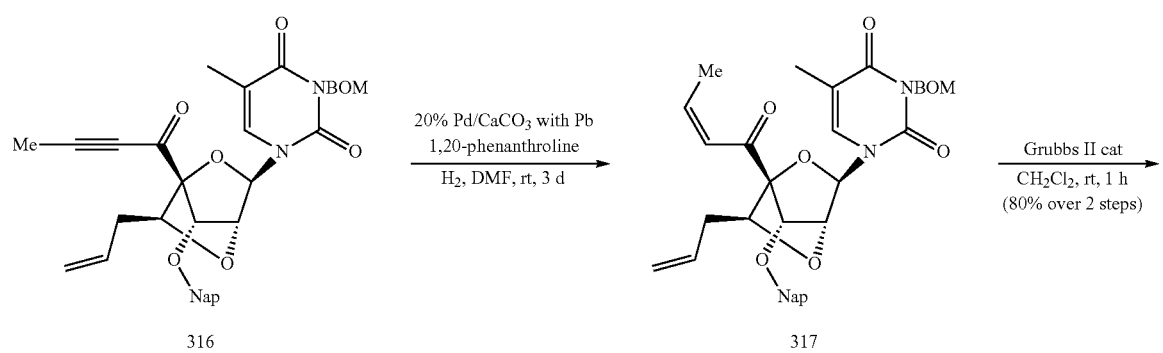
316 → 317

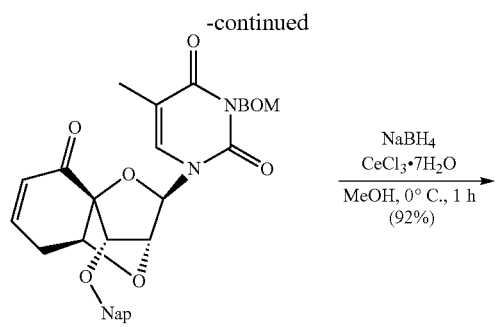
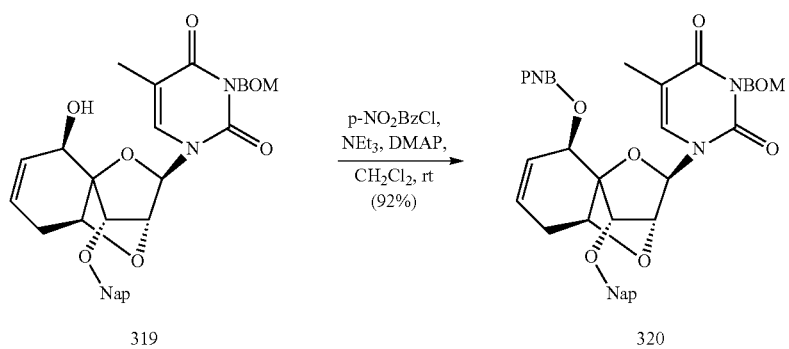
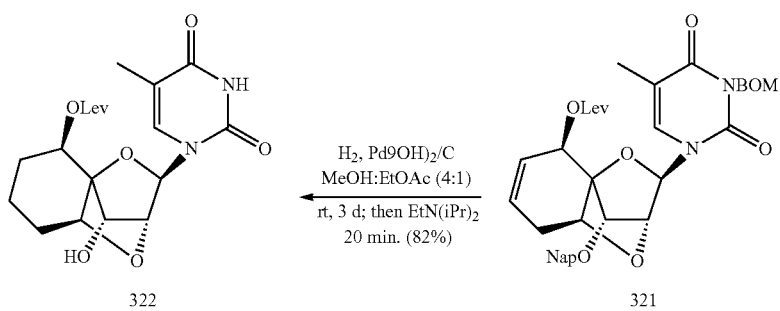
Compound 6 was prepared as per the procedure illustrated in Example 13. Compound 320 was crystallized in EtOAc/petroleum ether and the stereochemistry was confirmed by X-ray crystallography.

Example 36
Preparation of Compounds 323 and 324
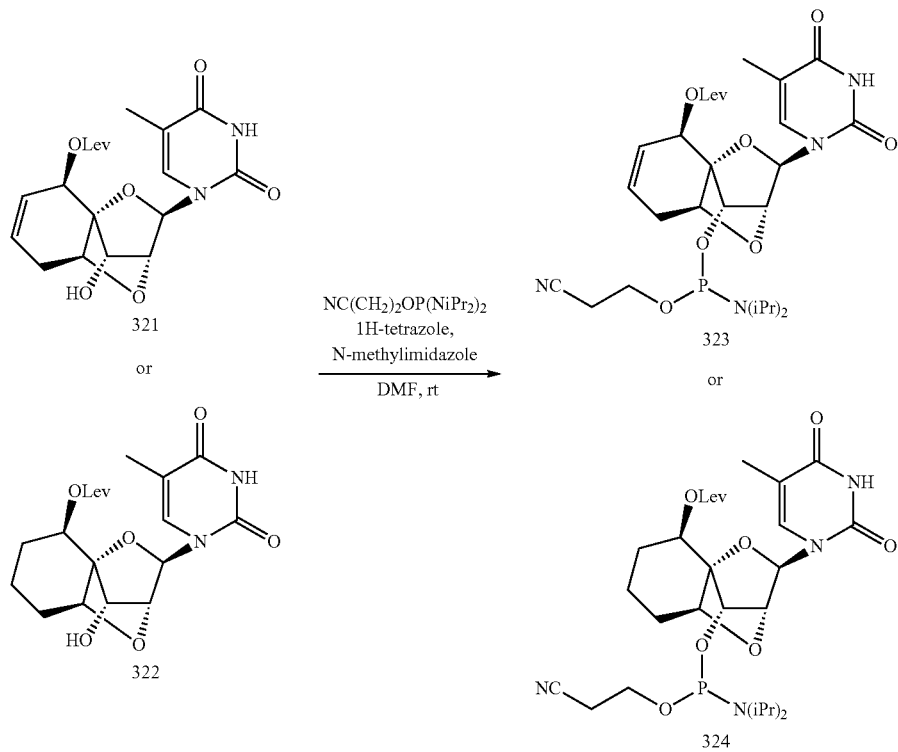
Compounds 321 and 322 are prepared as per the procedure illustrated in Example 35.
Example 37
Preparation of Compounds 334 and 335
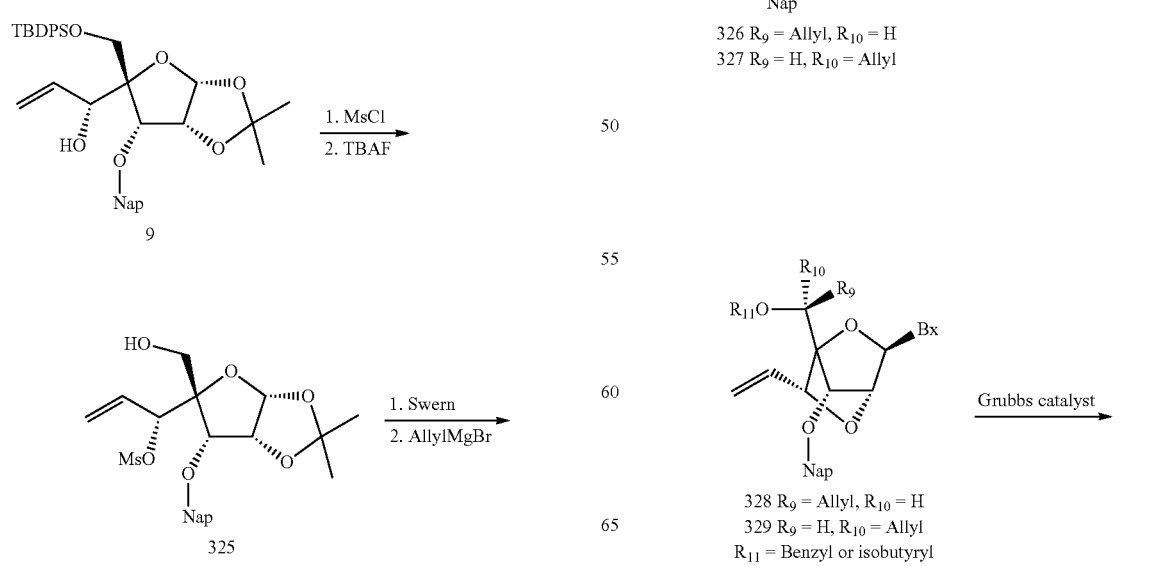

-continued

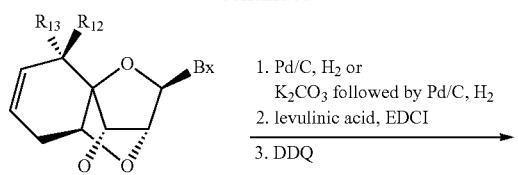

330 $R_{12} = OR_{11}$, $R_{13} = H$
331 $R_{12} = H$, $R_{13} = OR_{11}$

1. Pd/C, $H_2$ or $K_2CO_3$ followed by Pd/C, $H_2$
2. levulinic acid, EDCI
3. DDQ

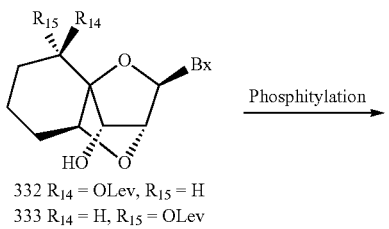

332 $R_{14} = OLev$, $R_{15} = H$
333 $R_{14} = H$, $R_{15} = OLev$

Phosphitylation

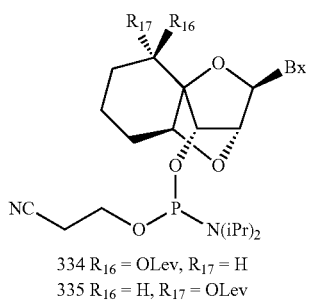

334 $R_{16} = OLev$, $R_{17} = H$
335 $R_{16} = H$, $R_{17} = OLev$

Compound 9 is prepared as per the procedure illustrated in Example 14.

Example 38

Preparation of Compounds 338 and 339

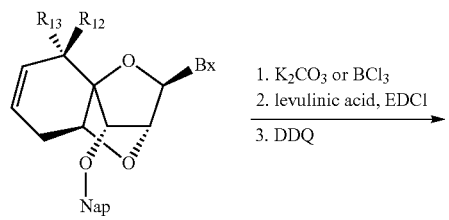

330 $R_{12} = OR_{11}$, $R_{13} = H$
331 $R_{12} = H$, $R_{13} = OR_{11}$
$R_{11}$ = Benzyl or isobutyryl 1. $K_2CO_3$ or $BCl_3$
2. levulinic acid, EDCl
3. DDQ

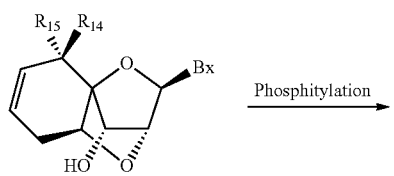

336 $R_{14} = OLev$, $R_{15} = H$
337 $R_{14} = H$, $R_{15} = OLev$

Phosphitylation

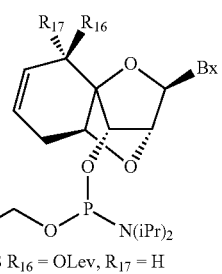

338 $R_{16} = OLev$, $R_{17} = H$
339 $R_{16} = H$, $R_{17} = OLev$

Compounds 330 and 331 are prepared as per the procedure illustrated in Example 37.

Example 39

Preparation of Compound 348

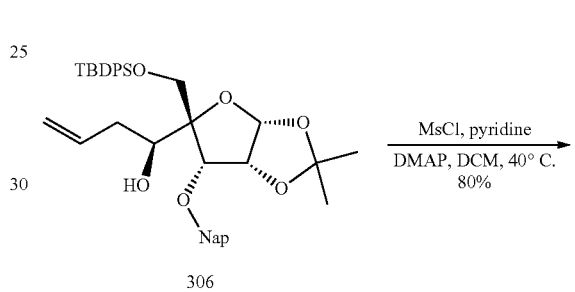

306

MsCl, pyridine
DMAP, DCM, 40° C.
80%

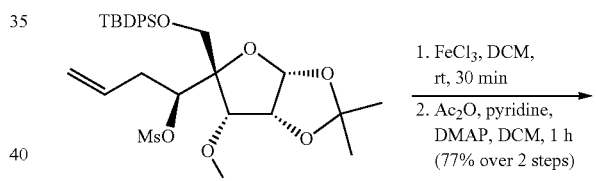

340

1. $FeCl_3$, DCM, rt, 30 min
2. $Ac_2O$, pyridine, DMAP, DCM, 1 h
(77% over 2 steps)

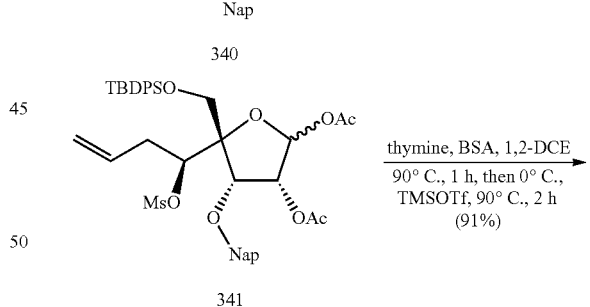

341 thymine, BSA, 1,2-DCE
90° C., 1 h, then 0° C., TMSOTf, 90° C., 2 h
(91%)

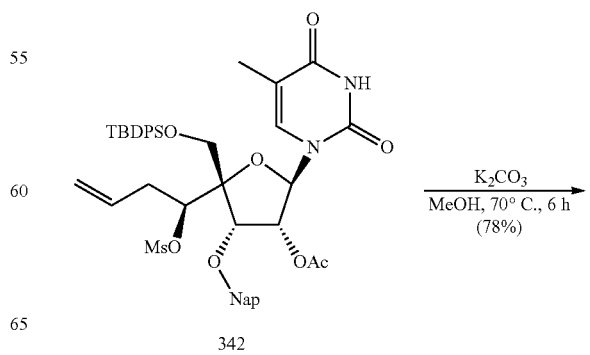

342

$K_2CO_3$
MeOH, 70° C., 6 h
(78%)

-continued
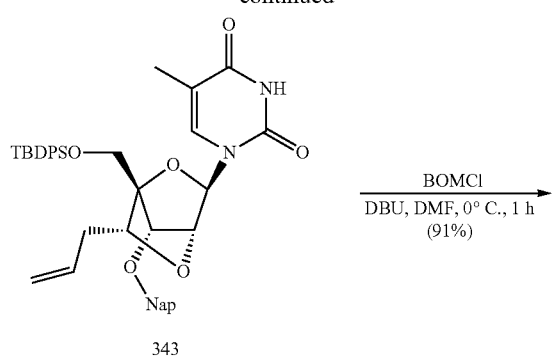
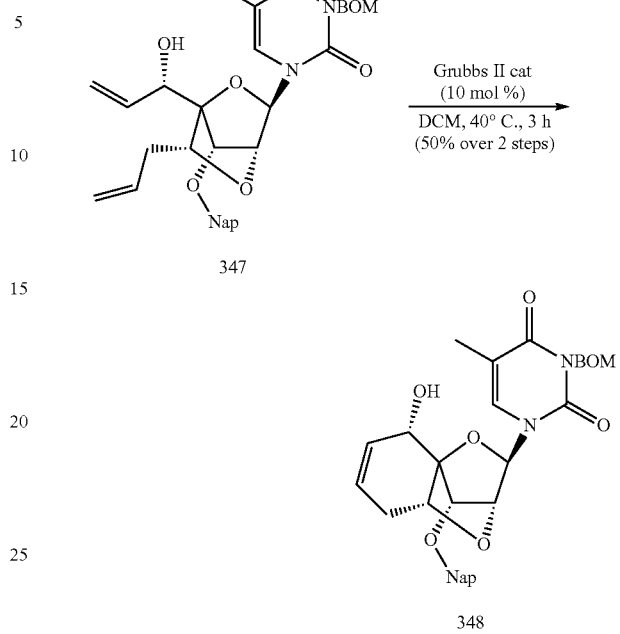
Compound 306 was prepared as per the procedure illustrated in Example 35.
Example 40
Preparation of Compounds 348 (Alternative Method I) and 350
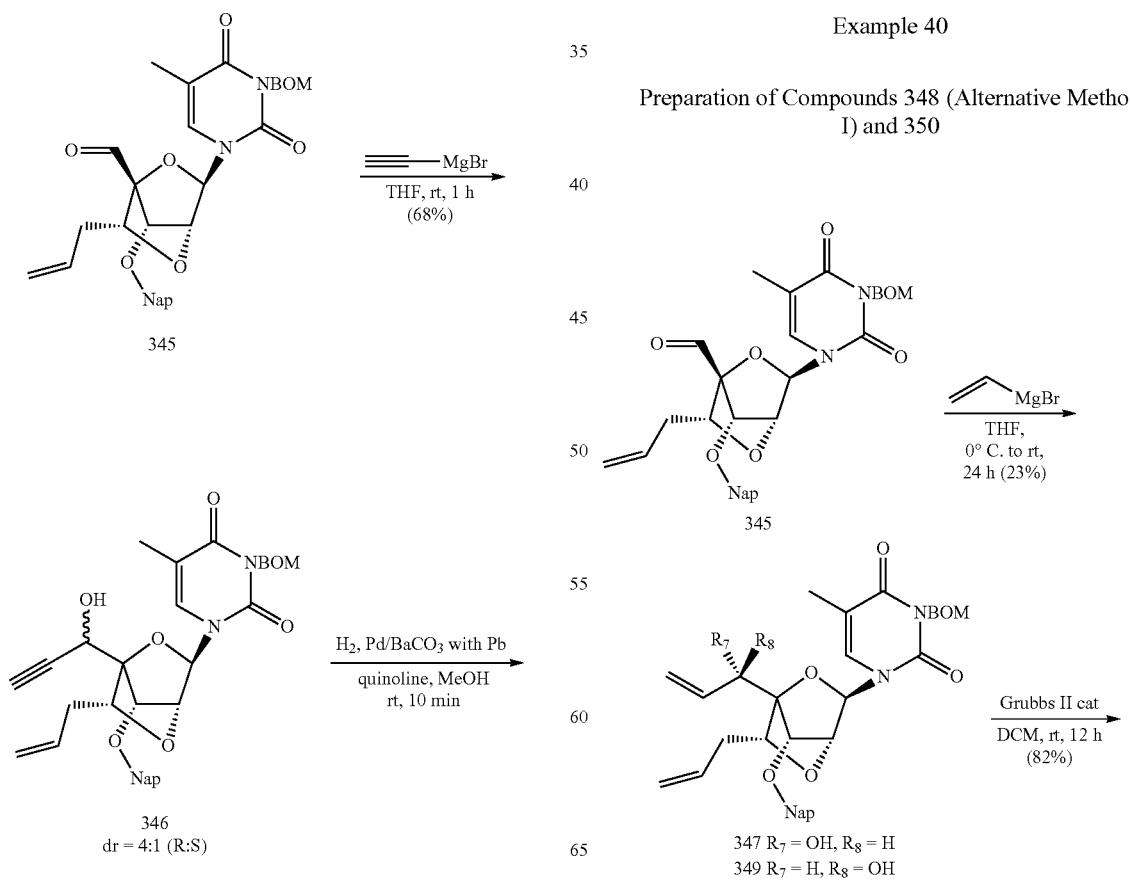

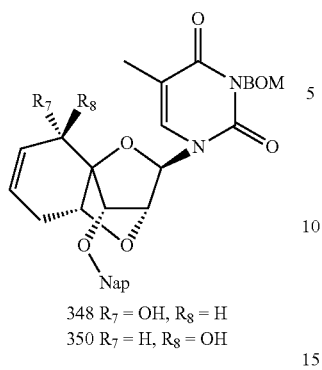

348 R₇ = OH, R₈ = H
350 R₇ = H, R₈ = OH

Compound 345 was prepared as per the procedure illustrated in Example 39.

Example 41

Alternative Method (II) for the Preparation of Compound 348

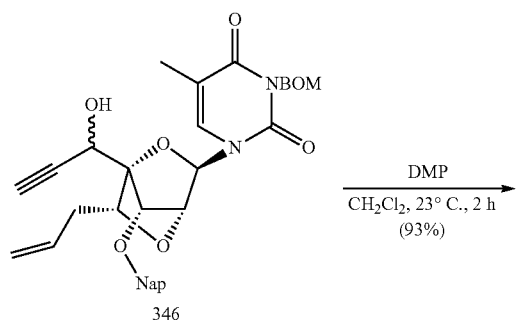

346

DMP
CH₂Cl₂, 23° C., 2 h
(93%)

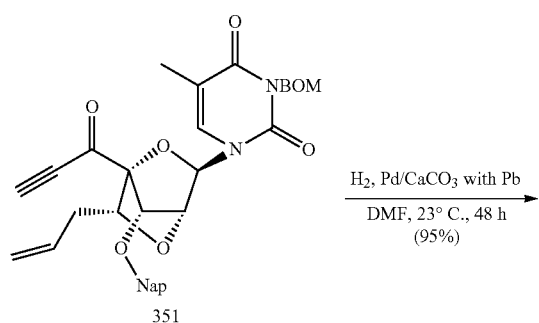

351

H₂, Pd/CaCO₃ with Pb
DMF, 23° C., 48 h
(95%)

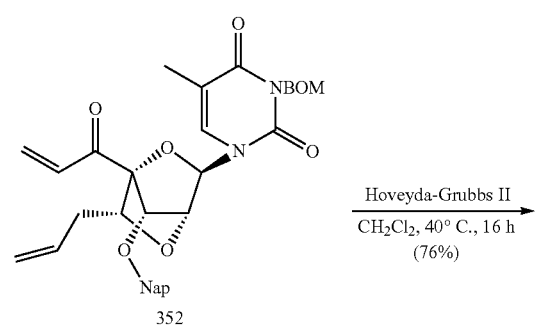

352

Hoveyda-Grubbs II
CH₂Cl₂, 40° C., 16 h
(76%)

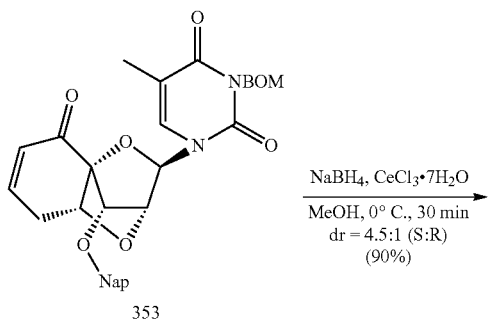

353

NaBH₄, CeCl₃·7H₂O
MeOH, 0° C., 30 min
dr = 4.5:1 (S:R)
(90%)

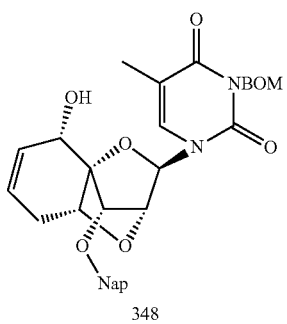

348

Hoveyda-Grubbs II =

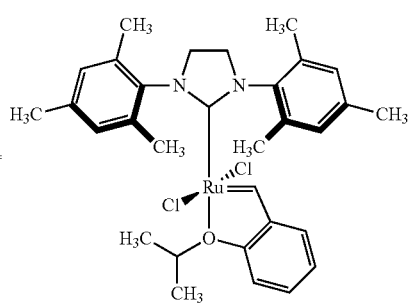

Compound 346 was prepared as per the procedure illustrated in Example 39.

Example 42

Preparation of Compounds 358 and 359

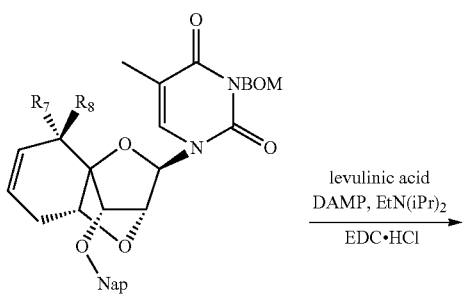

348 R₇ = OH, R₈ = H
350 R₇ = H, R₈ = OH levulinic acid
DAMP, EtN(iPr)₂
———————————→
EDC·HCl -continued

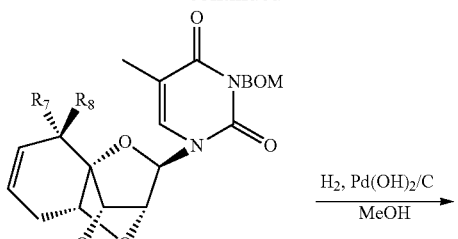

354 R7 = OLev, R8 = H
355 R7 = H, R8 = OLev $\xrightarrow{\text{H}_2, \text{Pd(OH)}_2/\text{C}}{\text{MeOH}}$

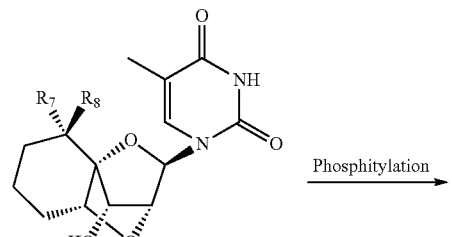

356 R7 = OLev, R8 = H
357 R7 = H, R8 = OLev

Phosphitylation →

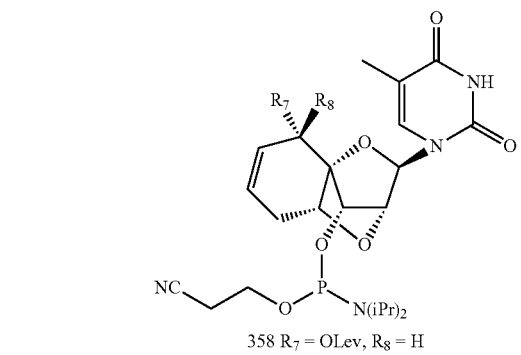

358 R7 = OLev, R8 = H
359 R7 = H, R8 = OLev

Compounds 348 and 350 are prepared as per the procedure illustrated in Examples 39, 40 or 41.

Example 43

Preparation of Compounds 362 and 363

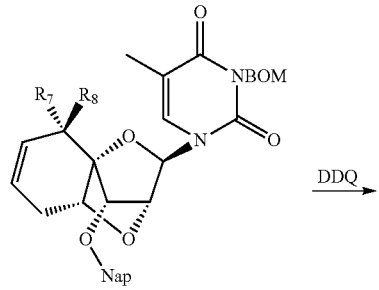

354 R7 = OLev, R8 = H
355 R7 = H, R8 = OLev $\xrightarrow{\text{DDQ}}$

-continued

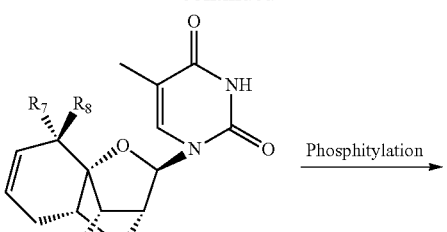

360 R7 = OLev, R8 = H
361 R7 = H, R8 = OLev

Phosphitylation →

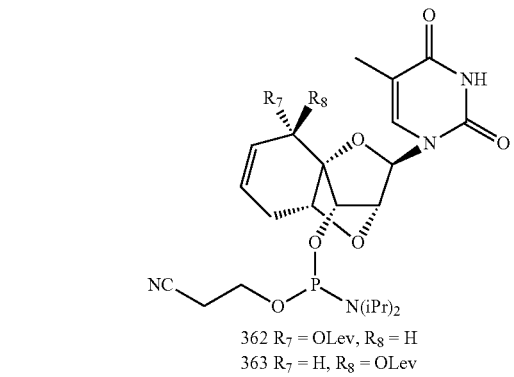

362 R7 = OLev, R8 = H
363 R7 = H, R8 = OLev

Compounds 354 and 355 are prepared as per the procedure illustrated in Example 42.

Example 44

Preparation of Compounds 374-377

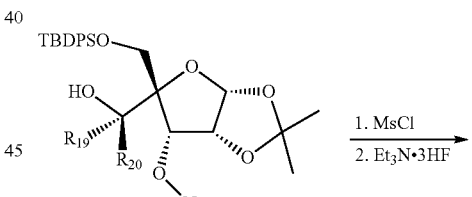

8 R19 = Vinyl, R20 = H
9 R19 = H, R20 = Vinyl $\xrightarrow{\text{1. MsCl} \atop \text{2. Et}_3\text{N·3HF}}$

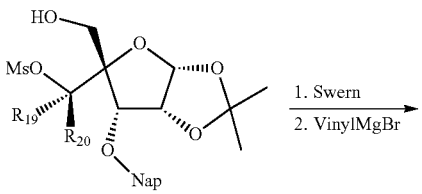

36 4R19 = Vinyl, R20 = H
36 5R19 = H, R20 = Vinyl $\xrightarrow{\text{1. Swern} \atop \text{2. VinylMgBr}}$ 119
-continued

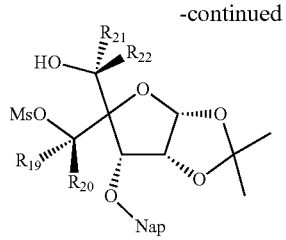

1. NaH, BnBr or isobutyryl chloride, Et₃N
2. AcOH, Ac₂O H₂SO₄

366 R₁₉, R₂₁ = Vinyl, R₂₀, R₂₂ = H
367 R₁₉, R₂₂ = Vinyl, R₂₀, R₂₁ = H
368 R₁₉, R₂₂ = H, R₂₀, R₂₁ = Vinyl
369 R₁₉, R₂₁ = H, R₂₀, R₂₂ = Vinyl

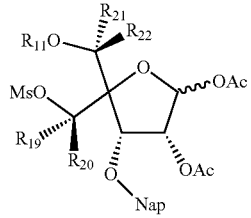

1. Nucleobase BSA, TMSOTf
2. K₂CO₃

370 R₁₉, R₂₁ = Vinyl, R₂₀, R₂₂ = H
371 R₁₉, R₂₂ = Vinyl, R₂₀, R₂₁ = H
372 R₁₉, R₂₂ = H, R₂₀, R₂₁ = Vinyl
373 R₁₉, R₂₁ = H, R₂₀, R₂₂ = Vinyl

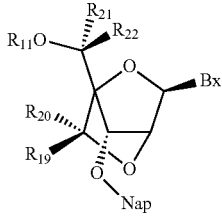

374 R₁₉, R₂₁ = Vinyl, R₂₀, R₂₂ = H
375 R₁₉, R₂₂ = Vinyl, R₂₀, R₂₁ = H
376 R₁₉, R₂₂ = H, R₂₀, R₂₁ = Vinyl
377 R₁₉, R₂₁ = H, R₂₀, R₂₂ = Vinyl R₁₁ = benzyl or isobutyryl
Bx = nucleobase Compounds 8 and 9 are prepared as per the procedure illustrated in Example 14. Isomers, Compounds 366 and 367 or 368 and 369 can be separated by column chromatography.

Example 45

Preparation of Compounds 386-389

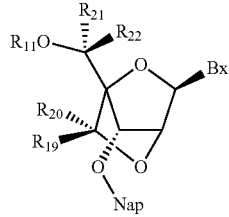

374 R₁₉, R₂₁ = Vinyl, R₂₀, R₂₂ = H
375 R₁₉, R₂₂ = Vinyl, R₂₀, R₂₁ = H
376 R₁₉, R₂₂ = H, R₂₀, R₂₁ = Vinyl
377 R₁₉, R₂₁ = H, R₂₀, R₂₂ = Vinyl 1. OsO₄ NMO, NaIO₄
2. Ammonium biborate
3. NaBH₃CN 120
-continued

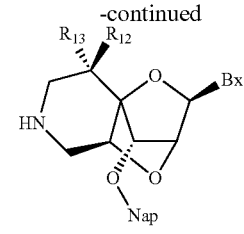

378 R₁₂ = OR₁₁, R₁₃ = H
379 R₁₂ = H, R₁₃ = OR₁₁

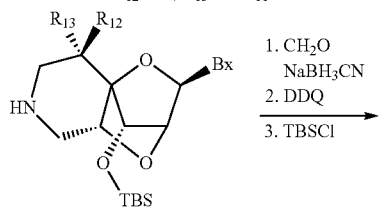

1. CH₂O NaBH₃CN
2. DDQ
3. TBSCl

380 R₁₂ = OR₁₁, R₁₃ = H
381 R₁₂ = H, R₁₃ = OR₁₁

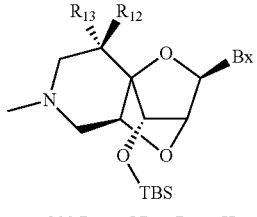

382 R₁₂ = OR₁₁, R₁₃ = H
383 R₁₂ = H, R₁₃ = OR₁₁

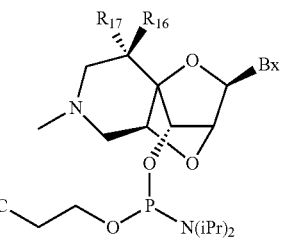

1. Pd/C, H₂ or K₂CO₃, MeOH
2. DMTCl
3. Et₃N·3HF
4. Phosphitylation

384 R₁₂ = OR₁₁, R₁₃ = H
385 R₁₂ = H, R₁₃ = OR₁₁

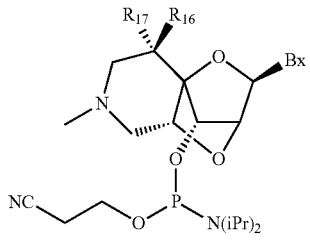

386 R₁₆ = ODMT, R₁₇ = H
387 R₁₆ = H, R₁₇ = ODMT

388 R₁₆ = ODMT, R₁₇ = H
389 R₁₆ = H, R₁₇ = ODMT

R₁₁ = Benzyl or isobutyryl
Bx = nucleobase

Compounds 374-377 are prepared as per the procedure illustrated in Example 44. In the tritylation step, other hydroxyl protecting groups can be used in place of DMTC1 (e.g. levulinic acid).

Example 46

Preparation of Compounds 386-389

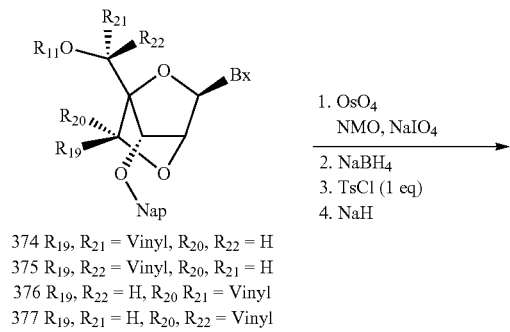

374 $R_{19}$, $R_{21}$ = Vinyl, $R_{20}$, $R_{22}$ = H
375 $R_{19}$, $R_{22}$ = Vinyl, $R_{20}$, $R_{21}$ = H
376 $R_{19}$, $R_{22}$ = H, $R_{20}$ $R_{21}$ = Vinyl
377 $R_{19}$, $R_{21}$ = H, $R_{20}$, $R_{22}$ = Vinyl 1. OsO$_4$ NMO, NaIO$_4$
2. NaBH$_4$
3. TsCl (1 eq)
4. NaH

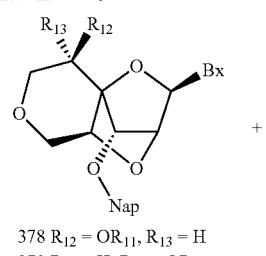

378 $R_{12}$ = OR$_{11}$, $R_{13}$ = H
379 $R_{12}$ = H, $R_{13}$ = OR$_{11}$

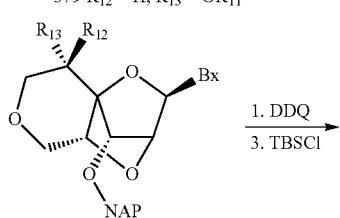

1. DDQ
3. TBSCl

380 $R_{12}$ = OR$_{11}$, $R_{13}$ = H
381 $R_{12}$ = H, $R_{13}$ = OR$_{11}$

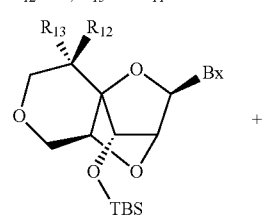

382 $R_{12}$ = OR$_{11}$, $R_{13}$ = H
383 $R_{12}$ = H, $R_{13}$ = OR$_{11}$

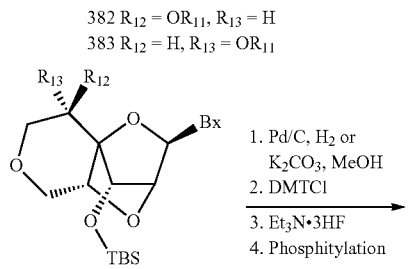

1. Pd/C, H$_2$ or K$_2$CO$_3$, MeOH
2. DMTCl
3. Et$_3$N·3HF
4. Phosphitylation

384 $R_{12}$ = OR$_{11}$, $R_{13}$ = H
385 $R_{12}$ = H, $R_{13}$ = OR$_{11}$

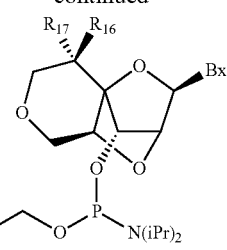

386 $R_{16}$ = ODMT, $R_{17}$ = H
387 $R_{16}$ = H, $R_{17}$ = ODMT

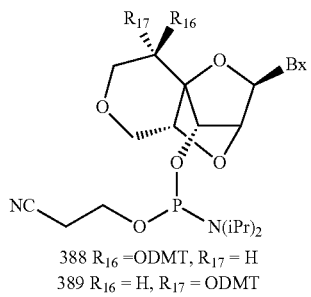

388 $R_{16}$ = ODMT, $R_{17}$ = H
389 $R_{16}$ = H, $R_{17}$ = ODMT $R_{11}$ = benzyl or isobutyryl
Bx = nucleobase Compounds 374-377 are prepared as per the procedure illustrated in Example 44. In the tritylation step, other hydroxyl protecting groups can be used in place of DMTC1 (e.g. levulinic acid).

Example 47

Preparation of Compounds 398-401

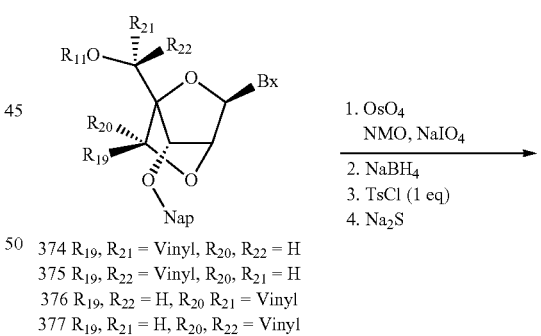

374 $R_{19}$, $R_{21}$ = Vinyl, $R_{20}$, $R_{22}$ = H
375 $R_{19}$, $R_{22}$ = Vinyl, $R_{20}$, $R_{21}$ = H
376 $R_{19}$, $R_{22}$ = H, $R_{20}$ $R_{21}$ = Vinyl
377 $R_{19}$, $R_{21}$ = H, $R_{20}$, $R_{22}$ = Vinyl 1. OsO$_4$ NMO, NaIO$_4$
2. NaBH$_4$
3. TsCl (1 eq)
4. Na$_2$S

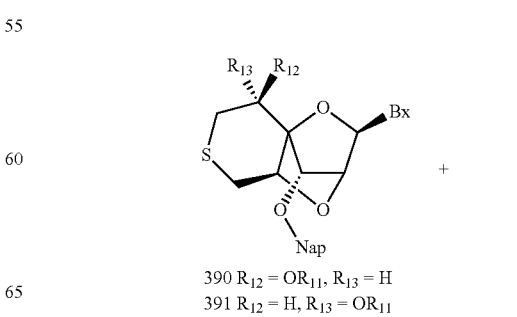

390 $R_{12}$ = OR$_{11}$, $R_{13}$ = H
391 $R_{12}$ = H, $R_{13}$ = OR$_{11}$

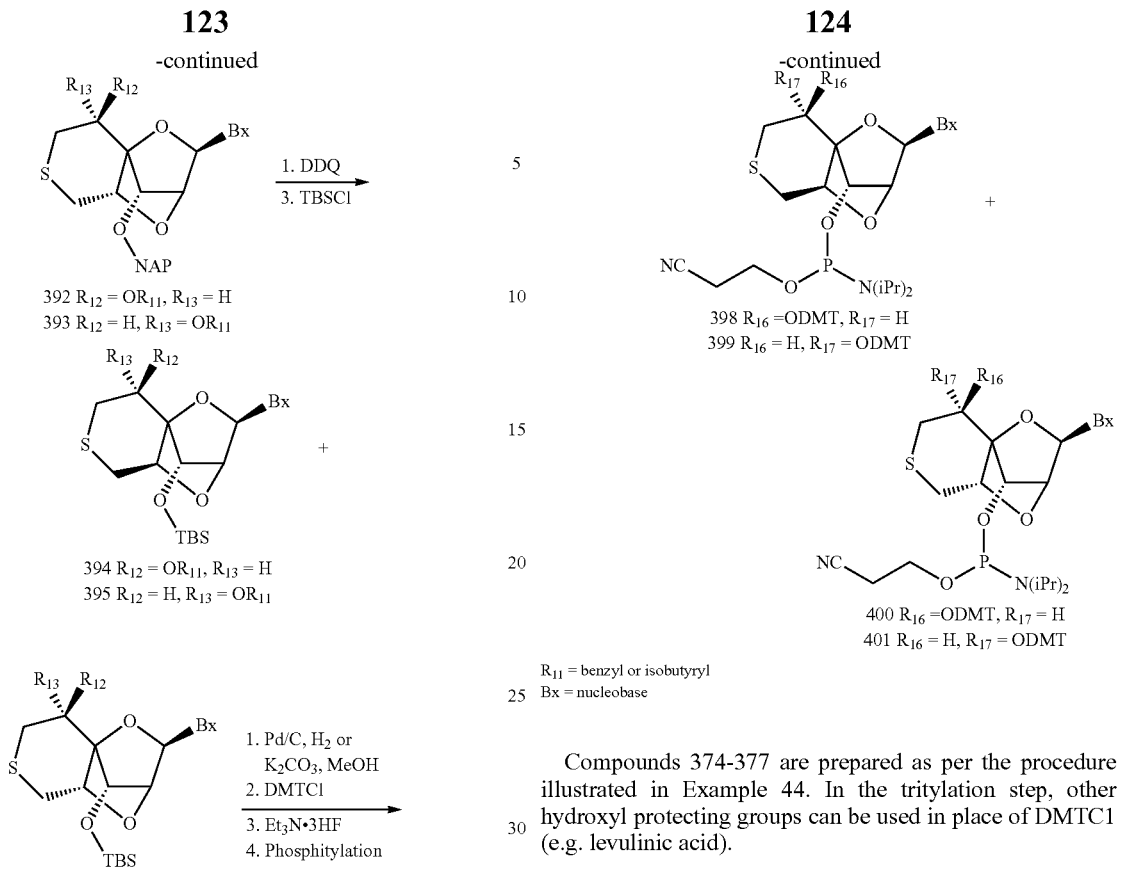
$R_{11}$ = benzyl or isobutyryl
Bx = nucleobase
Compounds 374-377 are prepared as per the procedure illustrated in Example 44. In the tritylation step, other hydroxyl protecting groups can be used in place of DMTCl (e.g. levulinic acid).
Example 48
Preparation of Dimeric Phosphoramidite, Compound 404
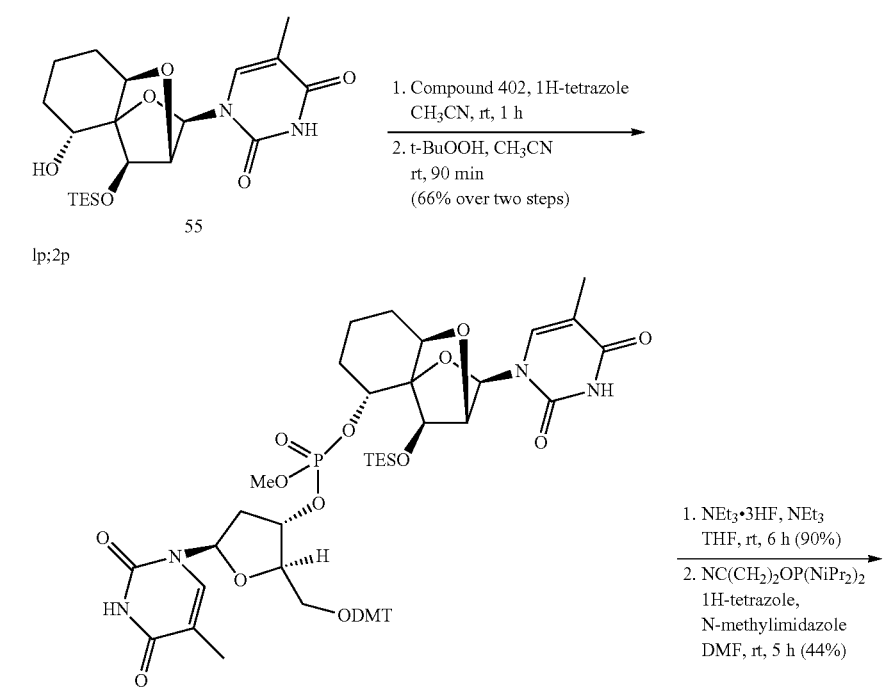

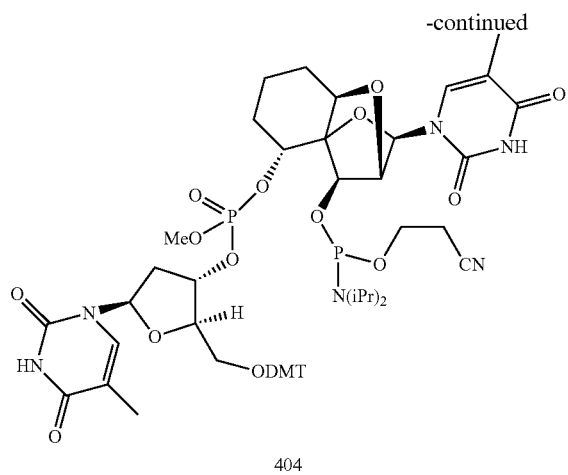

404

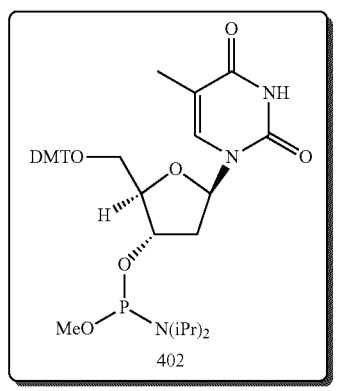

402 a) Preparation of Compound 403

Compound 55 was prepared as per the procedure illustrated in Example 18. Compound 402 is commercially available or can be prepared using similar procedures as published in the literature (see Quaedflieg et al., *J. Org. Chem.*, 1990, 55(1), 122-127). To a solution of Compound 55 (0.11 g, 0.26 mmol) and phosphoramidite Compound 402 (0.55 g, 0.78 mmol) in dry acetonitrile (4.3 mL) was added 1H-tetrazole (0.19 g, 2.6 mmol). After stirring at ambient temperature for 30 min, a solution of t-BuOOH (0.71 mL, 2.2 M) in acetonitrile was added and the stirring was continued for an additional 90 min. The reaction mixture was then diluted with ethyl acetate and the organic layer was washed with water and brine. The organic layer was collected, dried over sodium sulfate, and concentrated under reduced pressure. The residue was purified by reverse phase column chromatography on a Biotage KP-C18-HS 12M column with a gradient of 40-60% acetonitrile in water to afford the purified dimer. Fractions containing the purified dimer were then pooled and concentrated under reduced pressure to remove acetonitrile. The resulting white suspension was diluted with ethyl acetate, washed with water and brine, then concentrated under reduced pressure to provide the desired dimer Compound 403 (0.18 g, 66% over two steps) as a mixture of diastereomers at the phosphorous atom.

Compound 403: $^{31}$P NMR (121 MHz, CDCl$_3$): δ −1.14, −1.52. HRMS (QTOF) calc'd for $C_{52}H_{64}N_4O_{15}PSi$ [M−H]− m/z 1043.3875. found 1043.3971.

b) Preparation of Compound 404

To a solution of Compound 403 (0.175 g, 0.17 mmol) and triethylamine (0.03 mL, 0.2 mmol) in tetrahydrofuran (1.0 mL) was added triethylamine trihydrofluoride (0.08 mL, 0.5 mmol). After stirring at ambient temperature for 6 h, the volatiles were removed under reduced pressure and the residue was purified by flash column chromatography on silica gel with a solvent system of 5-10% methanol in dichloromethane to afford the dimer (0.13 g, 90%) as a mixture of diastereomers at the phosphorous atom.

Dimer: $^{31}$P NMR (121 MHz, CDCl$_3$): δ −2.26, −3.50. HRMS (QTOF) calc'd for $C_{46}H_{50}N_4O_{15}P$ [M−H]− m/z 929.3010. found 929.3099.

2-Cyanoethyl N,N,N',N'-tetraisopropylphosphorodiamidite (0.08 mL) was added to a solution of dimer from above (0.125 g, 0.134 mmol), N-methylimidazole (5 mL, 0.067 mmol) and 1H-tetrazole (8.7 mg, 0.12 mmol) in DMF (0.7 mL). After stirring at ambient temperature for 5 h, the reaction mixture was diluted with ethyl acetate and the organic layer was washed with brine. The organic layer was collected, dried over sodium sulfate, and concentrated under reduced pressure. The residue was purified by flash column chromatography on silica gel with a solvent system of 20-60% acetone in dichloromethane to afford the dimeric phosphoramidite Compound 404 (0.066 g, 44%) as a mixture of diastereomers at the phosphorous atom.

Compound 404: $^{31}$P NMR (121 MHz, CDCl$_3$): δ 150.08, 149.98, 149.69, 149.38, −1.32, −1.41, −1.62, −1.78. FIRMS (QTOF) calc'd for $C_{55}H_{69}N_6O_{16}P_2$ [M−H]− m/z 1129.4089. found 1129.4159.

Example 49

General Method for the Preparation of Oligomeric Compounds Comprising Locked Nucleic Acid (LNA), α-L-LNA or α-L-tricyclic nucleic acid (α-L-TriNA) modification The synthesis of oligomeric compounds presented in Table 1 was performed either on a 1 or 2 mmol scale using the UnyLinker™ polystyrene support on an ABI 394 DNA/RNA synthesizer. Standard conditions were used to incorporate phosphoramidite building blocks of the unmodified nucleosides which include for example T, G and C residues. Solvents and reagents used during synthesis were prepared according to the indications of the manufacturer. A 0.45 M solution of tetrazole in acetonitrile was used as an activator and dichloroacetic acid (3%) in dichloromethane was used as a detritylating reagent. A 0.1 M solution of unmodified phosphoramidite in acetonitrile was used with the coupling time of 2×4 min. For capping, a solution of acetic acid in THF (Cap A) and 1-methylimidazole (10%) in tetrahydrofuran/pyridine (Cap B) were used. For oxidation, a 0.02 M solution of iodine in tetrahydrofuran/pyridine/water was used.

For the incorporation of LNA or α-L-LNA phosphoramidite building block, similar protocol as described above was carried out except the coupling time was extended to 2×6 min.

For the incorporation of α-L-TriNA phosphoramidite building block, identical conditions as those described above was used and the synthesis was performed on a 1 mmol scale. The incorporation of the dimeric phosphoramidite was carried out by dissolving the dimer in dichloromethane to a 0.05 M solution (0.4 mL) and mixed with 0.45 M solution of tetrazole in acetonitrile (0.6 mL) prior to contact with the solid support. The coupling time was extended to 30 min with the coupling efficiency of approximately 50%. After the synthesis of the oligonucleotide was completed, the final DMT was cleaved and the cyanoethyl protecting groups were removed using triethylamine:acetonitrile (1:1, v/v). The remaining protecting groups were removed using concentrated aqueous ammonia at 55° C. for 8 h. The crude samples were purified by IE-HPLC using a linear gradient of buffer A (50 mM NaHCO$_3$ in acetonitrile:water 3:7) and B (1.5 M NaBr, 50 mM NaHCO$_3$ in acetonitrile:water 3:7). The purified oligomeric compounds were desalted using C$_{18}$ reverse phase cartridges. The integrity of the oligomeric compounds in Table 1 was confirmed and analyzed by ESI-mass spectrometry. ISIS 438705 was purchased from commercial sources and used as supplied without further purification.

The compositions of the oligonucleotides are described in Table 1. The internucleoside linkages throughout each oligomeric compound are phosphodiester linkages (P=O). Nucleosides without a subscript are β-D-2'-deoxyribonucleosides. Nucleosides followed by a subscript "1", "a" or "b" are defined below.

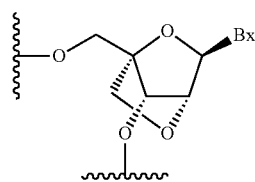

subscript 1

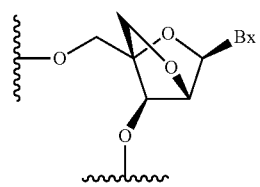

subscript a

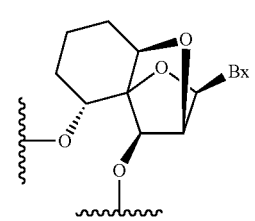

subscript b

TABLE 1

Modified oligomeric compounds prepared for thermal stability (T$_m$) study

| Oligo No. | Composition (5' to 3') | Modification | SEQ ID No. |
|---|---|---|---|
| ISIS 438705 | GCGTTTTTTGCT | DNA | 5 |
| ISIS 438707 | GCGTTT$_1$TTTGCT | LNA | 5 |
| ISIS 560180 | GCGTTT$_a$TTTGCT | α-L-LNA | 5 |
| A01 | GCGTTT$_b$TTTGCT | α-L-TriNA | 5 |

Example 50

Thermal Stability (T$_m$) Measurements

The oligomeric compounds in Table 1 were evaluated for thermal stability (T$_m$) using the method described herein. The T$_m$ of the modified 12mer oligomeric compounds were compared to an unmodified 12mer DNA oligonucleotide when duplexed to either the matched or mismatched RNA complement.

Tm's were determined using a Cary 100 Bio spectrophotometer with the Cary Win UV thermal program was used to measure absorbance vs. temperature. For the T$_m$ experiments, the oligomeric compounds were prepared at a concentration of 1.2 μM in 10 mM sodium phosphate buffer (pH 7.2) containing 100 mM NaCl and 0.1 mM EDTA. The concentrations, determined at 85° C. was 1.2 μM after mixing of equal volumes of selected oligomeric compound and complementary matched or mismatched RNA. The oligomeric compounds were hybridized with a complimentary matched or mismatched RNA by heating the duplex to 90° C. for 5 minutes and then cooling to room temperature. T$_m$ measurements were taken using a spectrophotometer while the duplex solution was heated in a cuvette at a rate of 0.5° C./min starting at 15° C. until the temperature was 85° C. T$_m$ values were determined using Vant Hoff calculations (A$_{260}$ vs temperature curve) using non self-complementary sequences where the minimum absorbance related to the duplex and the maximum absorbance related to the non-duplex single strand are manually integrated into the program. Mismatched thermal stability was also measured and calculated by subtracting values of T$_m$ measured vs the mismatched RNA complement from values of T$_m$ vs the matched RNA complement for each modification. The results are presented in Table 2.

The sequence for matched DNA complement is designated herein as SEQ ID No.: 6, 5'-d(AGCAAAXAACGC)-3', wherein X=A. The sequence for matched RNA complement is designated herein as SEQ ID No.: 6, 5'-r(AGCAAAYAACGC)-3', wherein Y=A. The mismatched RNA complement sequence is designated herein as SEQ ID No.: 7, 5'-r(AGCAAAZAACGC)-3', wherein Z=G, C or U.

TABLE 2

T$_m$ measurements of modified oligonucleotides vs DNA or RNA complement

| | | ΔT$_m$/mod vs DNA (° C.) | ΔT$_m$/mod vs RNA (° C.) | | | |
|---|---|---|---|---|---|---|
| | | Matched | Matched | Mismatched[1] | | |
| Oligo No. | Modification | X = A | Y = A | Z = G | Z = C | Z = U |
| ISIS 438705 | DNA | 0 (ref) | 0 (ref) | −4.1 | −13.0 | −13.2 |
| ISIS 438707 | LNA | +1.7 | +5.5 | −5.4 | −15.4 | −13.7 |
| ISIS 560180 | α-L-LNA | +1.4 | +5.7 | −4.7 | −14.8 | −13.5 |
| A01 | α-L-TriNA | +2.6 | +7.1 | −5.5 | −16.7 | −17.0 |

[1]Mismatched Discrimination [T$_m$(mismatched) − T$_m$(matched)]

---

What is claimed is:

1. A tricyclic nucleoside having Formula I:

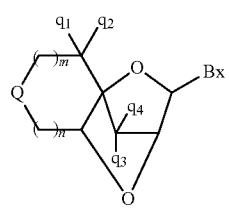

wherein:
Bx is a heterocyclic base moiety;
Q is $CH_2$—$CH_2$, CH=CH, O, S, or $NR_1$;
$R_1$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or a protecting group;
one of $q_1$ and $q_2$ is hydroxyl or a protected hydroxyl and the other of $q_1$ and $q_2$ is H;
one of $q_3$ and $q_4$ is hydroxyl, a protected hydroxyl or a reactive phosphorus group selected from a phosphoramidite, H-phosphonate and phosphate triester and the other of $q_3$ and $q_4$ is H;
wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)—$NJ_1J_2$, N(H)C(=S)$NJ_1J_2$ and a protecting group;
each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group;
n is 1 or 2; and
m is 0 when Q is $CH_2$—$CH_2$ or CH=CH and m is 1 when Q is O, S, or $NR_1$.

2. The compound of claim 1 wherein Bx is a pyrimidine, substituted pyrimidine, purine or substituted purine.

3. The tricyclic nucleoside of claim 1 wherein n is 1.

4. The tricyclic nucleoside of claim 1 wherein Q is CH=CH or $CH_2$—$CH_2$.

5. The tricyclic nucleoside of claim 1 wherein Q is O, S or $NR_1$ wherein $R_1$ is H, $C_1$-$C_3$ alkyl or substituted $C_1$-$C_3$ alkyl.

6. The tricyclic nucleoside of claim 5 wherein $R_1$ is methyl.

7. The tricyclic nucleoside of claim 1 having the configuration of one of formulas Ia or Ib:

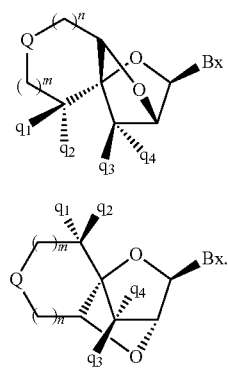

8. The tricyclic nucleoside of claim 7 wherein the tricyclic nucleoside has Formula Ia and $q_1$ and $q_4$ are each H or the tricyclic nucleoside has formula Ib and either $q_1$ and $q_3$ or $q_2$ and $q_3$ are each H.

9. The tricyclic nucleoside of claim 1 wherein one of $q_1$ and $q_2$ is a 4,4'-dimethoxytrityl protected hydroxyl group and one of $q_3$ and $q_4$ is diisopropylcyanoethoxy phosphoramidite.

10. An oligomeric compound comprising at least one tricyclic nucleoside having Formula II:

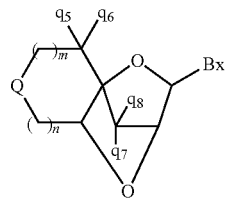

wherein independently for each tricyclic nucleoside having Formula II:
Bx is a heterocyclic base moiety;
Q is $CH_2$—$CH_2$, CH=CH, O, S, or $NR_1$;
$R_1$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or a protecting group;
wherein each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)—$NJ_1J_2$, N(H)C(=S)$NJ_1J_2$ and a protecting group;
each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group;
one of $q_5$ and $q_6$ is an internucleoside linking group linking the tricyclic nucleoside to the oligomeric compound, an optionally protected hydroxyl group or an oligomeric compound terminal group and the other of $q_5$ and $q_6$ is H;
one of $q_7$ and $q_8$ is an internucleoside linking group linking the tricyclic nucleoside to the oligomeric compound, an optionally protected hydroxyl group or an oligomeric compound terminal group and the other of $q_7$ and $q_8$ is H;
wherein at least one of $q_5$, $q_6$, $q_7$ and $q_8$ is an internucleoside linking group linking the tricyclic nucleoside to the oligomeric compound;
n is 1 or 2; and
m is 0 when Q is $CH_2$—$CH_2$ or CH=CH and m is 1 when Q is O, S, or $NR_1$.

11. The oligomeric compound of claim 10 wherein each Bx is, independently, uracil, thymine, cytosine, 5-methylcytosine, adenine or guanine for each tricyclic nucleoside having Formula II.

12. The oligomeric compound of claim 10 wherein n is 1 for each tricyclic nucleoside having Formula II.

13. The oligomeric compound of claim 10 wherein each Q is CH=CH.

14. The oligomeric compound of claim 10 wherein each Q is $CH_2$—$CH_2$.

15. The oligomeric compound of claim 10 wherein each Q is O, S or $NR_1$ wherein $R_1$ is H, $C_1$-$C_3$ alkyl or substituted $C_1$-$C_3$ alkyl.

16. The tricyclic nucleoside of claim 10 wherein each $R_1$ is methyl.

17. The oligomeric compound of claim 10 wherein each tricyclic nucleoside has the configuration of one of formulas IIa or IIb:

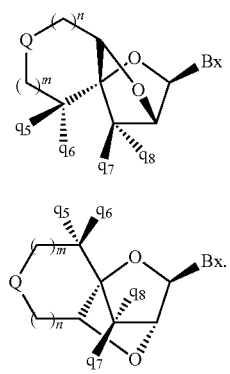

18. The oligomeric compound of claim 17 wherein each tricyclic nucleoside has formula IIa and each $q_5$ and $q_8$ is H or each tricyclic nucleoside has Formula IIb and either each $q_5$ and $q_7$ or each $q_6$ and $q_7$ is H.

19. The oligomeric compound of claim 10 wherein each internucleoside linking group between adjacent monomeric subunits is, independently, a phosphodiester internucleoside linking group or a phosphorothioate internucleoside linking group.

20. The oligomeric compound of claim 10 wherein essentially each internucleoside linking group between adjacent monomeric subunits is a phosphorothioate internucleoside linking group.

21. The oligomeric compound of claim 10 comprising at least two contiguous tricyclic nucleosides having Formula II.

* * * * *

SEQUENCE LISTING

<160> NUMBER OF SEQ ID NOS: 7

<210> SEQ ID NO 1
<211> LENGTH: 3160
<212> TYPE: DNA
<213> ORGANISM: Homo sapiens

<400> SEQUENCE: 1

```
cctcccctcg cccggcgcgg tcccgtccgc ctctcgctcg cctcccgcct ccccctcggtc    60
ttccgaggcg cccgggctcc cggcgcgcg gcggaggggg cgggcaggcc ggcgggcggt    120
gatgtggcag gactctttat gcgctgcggc aggatacgcg ctcggcgctg ggacgcgact    180
gcgctcagtt ctctcctctc ggaagctgca gccatgatga aagtttgaga gttgagccgc    240
tgtgaggcga ggccgggctc aggcgaggga gatgagagac ggcggcggcc gcggcccgga    300
gcccctctca gcgcctgtga gcagccgcgg gggcagcgcc ctcggggagc cggccggcct    360
gcggcggcgg cagcggcggc gtttctcgcc tcctcttcgt cttttctaac cgtgcagcct    420
cttcctcggc ttctcctgaa agggaaggtg gaagccgtgg gctcgggcgg gagccggctg    480
aggcgcggcg gcggcggcgg cggcacctcc cgctcctgga gcggggggga gaagcggcgg    540
cggcggcggc cgcggcggct gcagctccag ggaggggggtc tgagtcgcct gtcaccattt    600
ccagggctgg gaacgccgga gagttggtct ctccccttct actgcctcca acacggcggc    660
ggcggcggcg gcacatccag ggacccgggc cggtttaaa cctcccgtcc gccgccgccg    720
cacccccgt ggcccgggct ccggaggccg ccggcggagg cagccgttcg gaggattatt    780
cgtcttctcc ccattccgct gccgccgctg ccaggcctct ggctgctgag gagaagcagg    840
cccagtcgct gcaaccatcc agcagccgcc gcagcagcca ttacccggct gcggtccaga    900
gccaagcggc ggcagagcga ggggcatcag ctaccgccaa gtccagagcc atttccatcc    960
tgcagaagaa gccccgccac cagcagcttc tgccatctct ctcctccttt tcttcagcc    1020
acaggctccc agacatgaca gccatcatca aagagatcgt tagcagaaac aaaaggagat    1080
atcaagagga tggattcgac ttagacttga cctatattta tccaaacatt attgctatgg    1140
gatttcctgc agaaagactt gaaggcgtat acaggaacaa tattgatgat gtagtaaggt    1200
ttttggattc aaagcataaa aaccattaca agatatacaa tctttgtgct gaaagacatt    1260
atgacaccgc caaatttaat tgcagagttg cacaatatcc ttttgaagac cataacccac    1320
cacagctaga acttatcaaa ccctttgtg aagatcttga ccaatggcta agtgaagatg    1380
acaatcatgt tgcagcaatt cactgtaaag ctggaaaggg acgaactggt gtaatgatat    1440
gtgcatattt attacatcgg ggcaaatttt taaaggcaca agaggcccta gatttctatg    1500
```

```
gggaagtaag gaccagagac aaaaagggag taactattcc cagtcagagg cgctatgtgt    1560
attattatag ctacctgtta aagaatcatc tggattatag accagtggca ctgttgtttc    1620
acaagatgat gtttgaaact attccaatgt tcagtggcgg aacttgcaat cctcagtttg    1680
tggtctgcca gctaaaggtg aagatatatt cctccaattc aggacccaca cgacgggaag    1740
acaagttcat gtactttgag ttccctcagc cgttacctgt gtgtggtgat atcaaagtag    1800
agttcttcca caaacagaac aagatgctaa aaaaggacaa aatgtttcac ttttgggtaa    1860
atacattctt cataccagga ccagaggaaa cctcagaaaa agtagaaaat ggaagtctat    1920
gtgatcaaga aatcgatagc atttgcagta tagagcgtgc agataatgac aaggaatatc    1980
tagtacttac tttaacaaaa aatgatcttg acaaagcaaa taaagacaaa gccaaccgat    2040
acttttctcc aaattttaag gtgaagctgt acttcacaaa aacagtagag gagccgtcaa    2100
atccagaggc tagcagttca acttctgtaa caccagatgt tagtgacaat gaacctgatc    2160
attatagata ttctgacacc actgactctg atccagagaa tgaacctttt gatgaagatc    2220
agcatacaca aattacaaaa gtctgaattt tttttttatca agagggataa acaccatga    2280 aaataaactt gaataaactg aaaatggacc tttttttttt taatggcaat aggacattgt    2340
gtcagattac cagttatagg aacaattctc ttttcctgac caatcttgtt ttaccctata    2400
catccacagg gttttgacac ttgttgtcca gttgaaaaaa ggttgtgtag ctgtgtcatg    2460 tatataccctt tttgtgtcaa aaggacattt aaaattcaat taggattaat aaagatggca    2520
ctttcccgtt ttattccagt tttataaaaa gtggagacag actgatgtgt atacgtagga    2580 atttttttcct tttgtgttct gtcaccaact gaagtggcta aagagctttg tgatatactg    2640
gttcacatcc tacccctttg cacttgtggc aacagataag tttgcagttg gctaagagag    2700
gtttccgaaa ggttttgcta ccattctaat gcatgtattc gggttagggc aatggagggg    2760
aatgctcaga aaggaaataa ttttatgctg gactctggac catataccat ctccagctat    2820
ttacacacac ctttctttag catgctacag ttattaatct ggacattcga ggaattggcc    2880
gctgtcactg cttgttgttt gcgcattttt ttttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga aacacagcaa caatgactta    3060
accatataaa tgtggaggct atcaacaaag aatgggcttg aaacattata aaaattgaca    3120
atgatttatt aaatatgttt tctcaattgt aaaaaaaaaa                          3160

<210> SEQ ID NO 2
<211> LENGTH: 26
<212> TYPE: DNA
<213> ORGANISM: Artificial sequence
<220> FEATURE:
<223> OTHER INFORMATION: Primer

<400> SEQUENCE: 2
aatggctaag tgaagatgac aatcat                                           26

<210> SEQ ID NO 3
<211> LENGTH: 25
<212> TYPE: DNA
<213> ORGANISM: Artificial sequence
<220> FEATURE:
<223> OTHER INFORMATION: Primer

<400> SEQUENCE: 3
tgcacatatc attacaccag ttcgt                                            25
```

```
<210> SEQ ID NO 4
<211> LENGTH: 30
<212> TYPE: DNA
<213> ORGANISM: Artificial sequence
<220> FEATURE:
<223> OTHER INFORMATION: Probe

<400> SEQUENCE: 4
ttgcagcaat tcactgtaaa gctggaaagg                                    30

<210> SEQ ID NO 5
<211> LENGTH: 12
<212> TYPE: DNA
<213> ORGANISM: Artificial sequence
<220> FEATURE:
<223> OTHER INFORMATION: Synthetic Oligonucleotide

<400> SEQUENCE: 5 gcgtttttg ct                                                        12

<210> SEQ ID NO 6
<211> LENGTH: 12
<212> TYPE: RNA
<213> ORGANISM: Artificial sequence
<220> FEATURE:
<223> OTHER INFORMATION: Synthetic Oligonucleotide

<400> SEQUENCE: 6
agcaaaaaac gc                                                       12

<210> SEQ ID NO 7
<211> LENGTH: 12
<212> TYPE: RNA
<213> ORGANISM: Artificial sequence
<220> FEATURE:
<223> OTHER INFORMATION: Synthetic Oligonucleotide
<220> FEATURE:
<221> NAME/KEY: misc_feature
<223> OTHER INFORMATION: B = g, c, or u

<400> SEQUENCE: 7
agcaaabaac gc                                                       12
```